(12) United States Patent
Huang et al.

(10) Patent No.: US 8,324,241 B2
(45) Date of Patent: Dec. 4, 2012

(54) TRIAZOLO COMPOUNDS USEFUL AS DGAT1 INHIBITORS

(75) Inventors: Yanting Huang, Pennington, NJ (US); Chongqing Sun, East Windsor, NJ (US); R. Michael Lawrence, Yardley, PA (US); William R. Ewing, Yardley, PA (US); Huji Turdi, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 136 days.

(21) Appl. No.: 12/936,969

(22) PCT Filed: Apr. 7, 2009

(86) PCT No.: PCT/US2009/039770
§ 371 (c)(1),
(2), (4) Date: Oct. 8, 2010

(87) PCT Pub. No.: WO2009/126624
PCT Pub. Date: Oct. 15, 2009

(65) Prior Publication Data
US 2011/0034468 A1 Feb. 10, 2011

Related U.S. Application Data

(60) Provisional application No. 61/044,145, filed on Apr. 11, 2008.

(51) Int. Cl.
*C07D 277/42* (2006.01)
*C07D 487/04* (2006.01)
*C07D 471/22* (2006.01)
*C07D 471/14* (2006.01)
*A61K 31/427* (2006.01)
*A61K 31/437* (2006.01)
*A61K 31/5025* (2006.01)
*A61P 3/04* (2006.01)
*A61P 3/10* (2006.01)
*A61P 9/10* (2006.01)

(52) U.S. Cl. ........ 514/303; 514/249; 514/248; 544/350; 544/236

(58) Field of Classification Search .................. 546/120; 514/303
See application file for complete search history.

(56) References Cited

U.S. PATENT DOCUMENTS

| 7,091,228 | B2 | 8/2006 | Smith et al. |
| 7,179,802 | B2 | 2/2007 | Olson et al. |
| 7,300,932 | B2 | 11/2007 | Fox et al. |
| 2006/0281750 | A1 | 12/2006 | Li et al. |
| 2006/0287324 | A1 | 12/2006 | Sun et al. |
| 2008/0064717 | A1 | 3/2008 | Iyengar et al. |
| 2010/0266509 | A1* | 10/2010 | Ihle et al. .......................... 424/43 |
| 2011/0034506 | A1* | 2/2011 | Sun ................ 514/303 |

FOREIGN PATENT DOCUMENTS

| EP | 0 404 190 | 10/1995 |
| EP | 1 785 424 | 5/2007 |
| WO | WO 98/08847 | 3/1998 |
| WO | WO 01/83481 | 11/2001 |
| WO | WO 02/12236 | 2/2002 |
| WO | WO 2004/017950 | 3/2004 |
| WO | WO 2004/026859 | 4/2004 |
| WO | WO 2004/047755 | 6/2004 |
| WO | WO 2004/107863 | 12/2004 |
| WO | WO 2005/072740 | 8/2005 |
| WO | WO 2005/077953 | 8/2005 |
| WO | WO 2006/018727 | 2/2006 |
| WO | WO 2006/019020 | 2/2006 |
| WO | WO 2007/113226 | 10/2007 |
| WO | WO 2007/138472 | 12/2007 |
| WO | WO 2008/006540 | 1/2008 |

OTHER PUBLICATIONS

U.S. Appl. No. 12/936,997, filed Oct. 8, 2010, Sun.
Arampatzis, S. et al., "Comparative enzymology of 11β-hydroxysteroid dehydrogenase type 1 from six species", Journal of Molecular Endocrinology, vol. 35, pp. 89-101 (2005).
El-Mobayed, M. et al., "Reactions with 6-Acetyl-3,5-diarylcyclohexen-1-ones and 2-Hydroxy-4,6-diaryl nicotinonitrile Synthesized by Michael Reactions from 3-Nitrobenzal-p-isopropyl Acetophenones and Some Studies with the Products", Egypt. J. Pharm. Sci., vol. 30, No. 1-4, pp. 329-337 (1989).

* cited by examiner

*Primary Examiner* — Susanna Moore
*Assistant Examiner* — Cecilia M Jaisle
(74) *Attorney, Agent, or Firm* — Burton Rodney

(57) ABSTRACT

Disclosed are triazolopyridine compounds of Formula (I), including pharmaceutically acceptable salts thereof. Also, disclosed are methods of using the compound in the treatment of obesity, dyslipidemia, diabetes and atherosclerosis, and to pharmaceutical compositions comprising at least one compound of Formula (I) or a stereoisomer or pharmaceutically acceptable salt thereof.

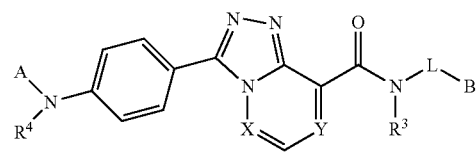

8 Claims, No Drawings

TRIAZOLO COMPOUNDS USEFUL AS DGAT1 INHIBITORS

This application is a filing under 37 CFR 371 based on PCT/US00/39770, filed on Apr. 7, 2009, which claims the benefit of Ser. No. 61/044,145, filed Apr. 11, 2008, now abandoned.

BACKGROUND

In mammals, there are two biochemical pathways for the synthesis of triacylglycerol: the monoacylglycerol pathway, which occurs exclusively in the small intestine (Lehner, R. et al., *Prog. Lipid Res.*, 35:169-201 (1996)), and the glycerol-3-phosphate pathway, which takes place ubiquitously but most notably in the liver and in adipose tissue (Bell, R. M. et al., *Annu. Rev. Biochem.*, 49:459-487 (1980)). The monoacylglycerol pathway initiates from acyl coenzyme A:monoacylglycerol acyltransferase (MGAT) (EC 2.3.1.22). Within minutes of its appearance from the digestion of dietary fat in the lumen of the small intestine, 2-monoacylglycerol is acylated by MGAT to form diacylglycerol. Diacylglycerol is further acylated by acyl coenzyme A:diacylglycerol acyltransferase (DGAT) (EC 2.3.1.20) to re-synthesize triacylglycerol, which is packaged into chylomicron lipoprotein particles that eventually are secreted into the lymph. In the glycerol-3-phosphate pathway, two fatty acyl coenzyme A molecules are added to glycerol-3-phosphate to form phosphatidate. These reactions are followed by the removal of the phosphate group by phosphatidate phosphohydrolase to generate diacylglycerol. Diacylglycerol is then further acylated by DGAT to form triacylglycerol. Collectively, DGAT lies at the final step of both triacylglycerol synthesis pathways.

Two DGAT enzymes have been identified and have been designated as DGAT1 and DGAT2 (Cases, S. et al., *Proc. Natl. Acad. Sci. USA*, 95:13018-13023 (1998)) (Oelkers, P. et al., *J. Biol. Chem.*, 273:26765-26771 (1998)) (Cases, S. et al., *J. Biol. Chem.*, 276:38870-38876 (2001)). Although they carry out identical enzymatic reactions, DGAT 1 and DGAT2 are encoded by two different genes that bear little sequence homology. Functionally, these two enzymes might have different physiological importance in vivo. DGAT1 knockout mice exhibit resistance towards becoming obese when challenged with a high fat (Smith, S. J. et al., *Nat. Genet.*, 25:87-90 (2000)). They are physically more active, possess a higher metabolic rate (Chen, H. C. et al., *Trends Cardiovasc. Med.*, 10: 188-192 (2000)) and appear to have greater insulin sensitivity (Chen, H. C. et al., *J. Clin. Invest.*, 109:1049-1055 (2002)). In contrast, DGAT2 knockout mice exhibit phenotypes such as lipopenia and skin barrier abnormalities, resulting in death soon after birth (Stone, S. J. et al., *J. Biol. Chem.*, 279:11767-11776 (2004)).

U.S. Pat. No. 7,300,932 B2 discloses fused bicyclic nitrogen-containing heterocyclic compounds that are useful for treating or preventing conditions and disorders associated with DGAT. As may be appreciated, there still remains a need for new compounds that are inhibitors of DGAT and are useful for the treatment of DGAT related conditions and disorders.

Applicants have found triazolopyridine compounds that have activity as inhibitors of DGAT, in particular DGAT1, and are thereby useful in therapy.

SUMMARY OF THE INVENTION

The present invention is directed to compounds according to Formula (I):

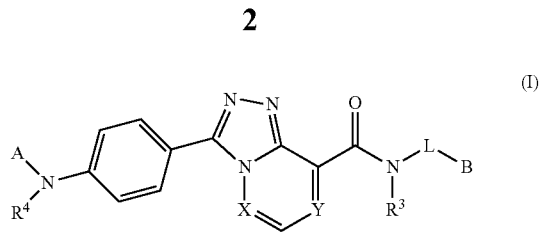

including stereoisomers and pharmaceutically acceptable salts thereof, wherein:

A is hydrogen, alkyl, cycloalkyl, aryl, heterocyclyl, —C(O)R$^6$, —C(O)OR$^6$, or —C(O)NR$^6$R$^7$;

L is —(CR$^1$R$^2$)$_n$—;

n is 1, 2, or 3;

B is —OR$^5$, —C(O)OR$^5$, —OC(O)R$^5$, or —OC(O)OR$^5$;

one of X and Y is CH or N, and the other of X and Y is CH;

R$^1$ and R$^2$ are, independently at each occurrence, hydrogen, alkyl, cycloalkyl, aryl, and/or heterocyclyl, or one R$^1$ and one R$^2$ form a C$_3$-C$_7$cycloalkyl or 4- to 7-membered heterocyclyl ring having one or two heteroatoms;

R$^3$ is hydrogen or alkyl, or R$^3$ and R$^1$ form a 4- to 7-membered heterocyclyl ring having one or two heteroatoms;

R$^4$ is hydrogen or alkyl;

R$^5$ is hydrogen or alkyl;

R$^6$ is alkyl, cycloalkyl, aryl, or heterocyclyl; and

R$^7$ is hydrogen or alkyl, or R$^7$ and R$^6$ together with the nitrogen atom to which they are attached form a 4- to 7-membered heterocyclyl ring having one or two heteroatoms;

wherein:

each of said alkyl is substituted with 0-3 R$^a$;

each of said cycloalkyl is substituted with 0-3 R$^a$;

each of said aryl is substituted with 0-4 R$^b$;

each of said heterocyclyl is substituted with 0-4 R$^b$;

R$^a$ is, independently at each occurrence, F, Cl, Br, —CF$_3$, —OH, —OCH$_3$, —OCF$_3$, —CN, —NR$^c$R$^d$, phenyl, imidazolyl, and/or C$_1$-C$_3$alkoxy;

R$^b$ is, independently at each occurrence, C$_1$-C$_4$alkyl, F, Cl, Br, —CF$_3$, —OH, —OCH$_3$, —OCF$_3$, —CN, —NR$^c$R$^d$, and/or C$_1$-C$_3$alkoxy; and R$^c$ and R$^d$ are, independently at each occurrence, H and/or C$_1$-C$_4$alkyl, or R$^c$ and R$^d$ together with the nitrogen atom to which they are attached, form a 4- to 7-membered heterocyclyl ring with one or two heteroatoms.

Also described is a pharmaceutical composition comprising a compound of Formula (I) and a pharmaceutically acceptable carrier or diluent.

Further described is method for treating a condition or disorder comprising administering to a patient in need thereof at least one compound of Formula (I); wherein said condition or disorder is obesity, dyslipidemia, diabetes, or atherosclerosis.

DETAILED DESCRIPTION

Listed below are definitions of various terms used to describe the present invention. These definitions apply to the terms as they are used throughout the specification (unless they are otherwise limited in specific instances) either individually or as part of a larger group.

The term "alkyl" and "alk" refer to a straight or branched chain alkane (hydrocarbon) radical containing from 1 to 12 carbon atoms, preferably from 1 to 6 carbon atoms, and more preferably from 1 to 4 carbon atoms. Exemplary "alkyl" and/or "alk" groups include, but are not limited to, for example, methyl, ethyl, propyl, butyl, pentyl, hexyl, isohexyl, heptyl, octyl, nonyl, decyl, and dodecyl.

The term "lower alkyl" refers to an "alkyl" and/or "alk" group containing from 1 to 4 carbon atoms and preferably from 1 to 2 carbon atoms. When a subscript is used with reference to an alkyl or other group, the subscript refers to the number of carbon atoms the group may contain. For example, the term "$C_0$-$C_4$alkyl" includes a bond and an alkyl group containing 1 to 4 carbon atoms, and the term "$C_1$-$C_4$alkyl" refers to alkyl groups containing 1 to 4 carbon atoms. Exemplary lower alkyl groups include, but are not limited to, for example, methyl, ethyl, propyl including n-propyl and iso-propyl, and butyl including n-butyl, isobutyl, and t-butyl.

The "alkyl" and/or "alk" group can be optionally substituted with one or more substituents, preferably 1 to 3 substituents, at any available and substitutable position. Exemplary substituents include halogen (e.g., a single halo substituent or multiple halo substituents form, in the latter case, groups such as, for example, a perfluoroalkyl group or an alkyl group bearing —$CCl_3$ or —$CF_3$), hydroxyl, —$NH_2$, —NH(alkyl), —$CF_3$, —N(alkyl)$_2$, cyano, $C_1$-$C_3$alkoxy group, phenyl, imidazolyl, and halogenated alkoxy group such as —$OCF_3$.

The term "cycloalkyl" refers to a fully saturated hydrocarbon group containing from 1 to 4 rings and 3 to 8 carbon atoms per ring. Exemplary cycloalkyl groups include, but are not limited to, for example, cyclopropyl, cyclobutyl, cyclopentyl, cyclohexyl, and cycloheptyl. The cycloalkyl group can be optionally substituted with one or more substituents, preferably 1 to 3 substituents, at any available and substitutable point of attachment. Exemplary substituents include those groups recited for substituted alkyl.

The term "aryl" refers to cyclic aromatic hydrocarbon groups having from 1 to 2 aromatic rings, such as, for example, phenyl, biphenyl, or naphthyl. When the aryl group contains two aromatic rings (e.g., bicyclic, etc.), the aromatic rings may be joined at a single point (e.g., biphenyl) or fused (e.g., naphthyl and phenanthrenyl). The aryl group can be optionally substituted with one or more substituents, preferably 1 to 4 substituents, at any available and substitutable ring position, or where valence allows on any rings fused or attached thereto. Exemplary substituents include alkyl and those groups recited for substituted alkyl.

The term "heterocyclo", "heterocycle", "heterocyclyl" or "heterocyclic ring", as used herein, represents 3-, 4-, 5-, 6-, or 7-membered monocyclic or polycyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3, or 4 heteroatoms independently selected from the group consisting of N, O, and S; and including any polycyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in the creation of a stable structure. The heterocycle, heterocyclic, or heterocyclo group can be substituted at any available point of attachment with at least one substituent, preferably 1 to 4 substituents, selected from alkyl and those recited for substituted alkyl. When the term "heterocycle" is used, it is intended to include heteroaryl. The heterocyclo, heterocycle, heterocyclic, or heterocyclo group can be substituted at any available point of attachment with at least one substituent, preferably 1 to 4 substituents, selected from alkyl and those recited for substituted alkyl.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benzthiazolyl, benztetrazolyl, benzisoxazolyl, benzisothiazolyl, benzimidazalonyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, (uranyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "aromatic heterocyclic group" or "heteroaryl" is intended to mean fully unsaturated heterocyclyl rings, including monocyclic and polycyclic aromatic hydrocarbons having at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl indazolyl, indolinyl, 1,2,4-thiadiazolyl, isothiazolyl, purinyl, carbazolyl, benzimidazolyl, benzodioxolanyl, and benzodioxane. Heteroaryl groups are unsubstituted or substituted. Heteroaryl groups can be substituted at any available point of attachment with at least one substituent, preferably 1 to 4 substituents, selected from alkyl and those recited for substituted alkyl.

The term "alkoxy" as employed herein alone or as part of another group includes an alkyl as defined above linked through an oxygen atom.

The term "halogen" or "halo" as used herein alone or as part of another group refers to fluorine, chlorine, bromine, and iodine, with fluorine, chlorine, and bromine being preferred.

The term "cyano," as used herein, refers to a —CN group.

The term "methylene," as used herein, refers to a —CH$_2$— group.

The compounds of the present invention can be present as salts, which are also within the scope of this invention. Pharmaceutically acceptable (i.e., non-toxic, physiologically acceptable) salts are preferred. If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula (I) having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di-, or tri-lower alkylamine, for example ethyl, text-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of Formula (I) with an open valence for further substitution wherein such substitution can, upon biotransformation, generate a compound of Formula (I). Examples of such functional groups of bioactive metabolites include, but are not limited to, —OH, —NH$_2$, or functional groups wherein the hydrogen can be replaced with a functional group such as —PO$_3$H$_2$ for example, which, upon biotransformation generates an —OH or —NH$_2$ functional group of a compound of Formula (I).

The term "prodrug" as employed herein includes functionalization of bioactive amine- or hydroxyl-containing compounds of Formula (I) to form alkyl-, acyl-, sulfonyl-, phosphoryl-, or carbohydrate-substituted derivatives. Such derivatives are formed by reacting compounds of Formula (I) with alkylating-, acylating-, sulfonylating-, or phosphorylating reagents employing procedures known to those skilled in the art. Alkylation of amines of Formula (I) may result in, but is not limited to, derivatives that include spacer units to other prodrug moieties such as substituted alkoxymethyl-, acyloxymethyl-, phosphoryloxymethyl-, or sulfonyloxymethyl-groups. Alkylation of amines of Formula (I) may result in the generation of quarternary amine salts that act in vivo to provide the bioactive agent (i.e., the compound of Formula (I)).

Preferred prodrugs consist of a compound of Formula (I) where a pendant hydroxyl is phosphorylated to generate a phosphate derivative. Such a prodrug may also include a spacer group between the compound of Formula (I) and the phosphate group, such as a methyleneoxy-group. Methods to generate such a prodrug from a compound of Formula (I) are known to those skilled in the art, and are listed in the references below.

Preferred prodrugs also consist of a compound of Formula (I) where a pendant amine, such as a pyridine group, is alkylated with a group, such as methyl, to form a quarternary ammonium ion salt. Methods to generate such a prodrug from a compound of Formula (I) are known to those skilled in the art, and are listed in the references below.

Any compound that can be converted in vivo to provide the bioactive agent (i.e., the compound of Formula (I)) is a prodrug within the scope and spirit of the invention.

Various forms of prodrugs are well known in the art. A comprehensive description of prodrugs and prodrug derivatives are described in a) *The Practice of Medicinal Chemistry*, Camille G. Wermuth et al., Ch. 31 (Academic Press, 1996);
b) *Design of Prodrugs*, edited by H. Bundgaard (Elsevier, 1985);
c) *A Textbook of Drug Design and Development*, P. Krogsgaard-Larson and H. Bundgaard, eds., Ch. 5, pp. 113-191 (Harwood Academic Publishers, 1991);
d) *Hydrolysis in Drug and Prodrug Metabolism*, B. Testa and J. M. Mayer (Verlag Helvetica Chimica Acta AG, Zurich, Switzerland; Wiley-VCH, Weinheim, Federal Republic of Germany, 2003);
e) Ettmayer, P. et al., "Lessons Learned from Marketed and Investigational Prodrugs", *J. Med. Chem.*, 47(10):2393-2404 (2004); and
f) Davidsen, S. K. et al., "N-(Acyloxyalkyl)pyridinium Salts as Soluble Prodrugs of a Potent Platelet Activating Factor Antagonist", *J. Med. Chem.*, 37(26):4423-4429 (1994).

The term "patient" as used herein encompasses all mammalian species including humans, cows, horses, dogs, and cats; and preferably, humans.

The term "therapeutically effective" is intended to qualify the amount of each agent, which will treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of the present invention can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

In one embodiment, compounds of Formula (I) are provided where X is CH and Y is CH. The compounds of this embodiment have structures represented by Formula (Ia):

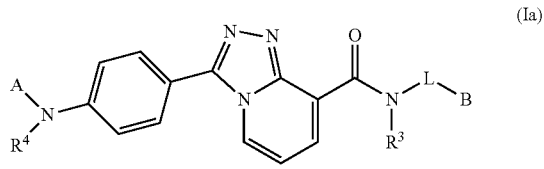

(Ia)

and stereoisomers or salts thereof, wherein: A, L, B, $R^3$, and $R^4$ are as defined hereinabove. The compounds of Formula (Ia) are triazolopyridine derivatives.

In one embodiment, compounds of Formula (I) are provided where X is N and Y is CH. The compounds of this embodiment have structures represented by Formula (Ib):

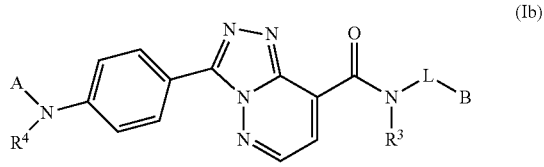

(Ib)

including stereoisomers or salts thereof, wherein: A, L, B, $R^3$, and $R^4$ are as defined hereinabove. The compounds of Formula (Ib) are triazolopyridazine derivatives.

In one embodiment, compounds of Formula (I) are provided where X is CH and Y is N. The compounds of this embodiment have structures represented by Formula (Ic):

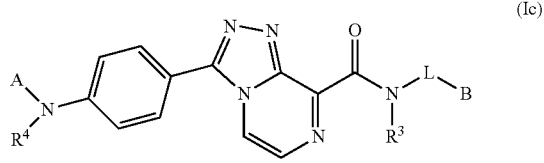

(Ic)

Including stereoisomers or salts thereof, wherein: A, L, B, $R^3$, and $R^4$ are as defined hereinabove. The compounds of Formula (Ic) are triazolopyrazine derivatives.

In one embodiment, compounds of Formula (I) are provided wherein L is $-(CR^1R^2)_n-$, n is 1 or 2, and $R^1$ and $R^2$ are as defined hereinabove. Examples of suitable L groups include, but are not limited to, $-CR^1R^2-$ in which n is 1 and $-CHR^1-$ in which n is 1 and $R^2$ is hydrogen.

In one embodiment, compounds of Formula (I) are provided wherein $R^1$ and $R^2$ are, independently at each occurrence, hydrogen, $C_1$-$C_6$ alkyl, $C_3$-$C_7$ cycloalkyl, aryl, and/or 1- or 2-ring heterocyclyl; and each alkyl is substituted with 0-3 $R^a$, each cycloalkyl is substituted with 0-3 $R^a$, each aryl is substituted with 0-4 $R^b$, and each heteroaryl is substituted with 0-4 $R^b$; and $R^a$ and $R^b$ are as defined hereinabove. Preferably, $R^1$ is hydrogen, $C_1$-$C_6$alkyl, $C_3$-$C_7$cycloalkyl, or phenyl; and $R^2$ is hydrogen or methyl. More preferably, $R^1$ is hydrogen, $C_1$-$C_4$alkyl, $C_5$-$C_7$cycloakyl, or phenyl; and $R^2$ is hydrogen. For example, the present embodiment provides compounds of Formula (I) wherein $R^1$ is hydrogen, $C_1$-$C_4$alkyl, hydroxyethyl, cyclohexyl, phenyl, or methyl substituted with phenyl, hydroxyphenyl or imidazolyl; and $R^2$ is hydrogen.

In one embodiment, compounds of Formula (I) are provided wherein one $R^1$ and one $R^2$ form a $C_3$-$C_7$cycloalkyl or 4- to 7-membered heterocyclyl ring having one or two heteroatoms; wherein said cycloalkyl ring is substituted with 0-3 $R^a$ and said heterocyclyl ring is substituted with 0-4 $R^b$, and $R^a$ and $R^b$ are as defined hereinabove. Preferably, $R^1$ and $R^2$ form a $C_3$-$C_7$cycloalkyl, and more preferably, $R^1$ and $R^2$ form a $C_5$-$C_7$cycloalkyl. For example, this embodiment provides compounds of Formula (I) wherein $R^1$ and $R^2$ form a cyclohexyl group.

In one embodiment, compounds of Formula (I) are provided wherein n is 2 and L is $-CR^1R^2CR^1R^2-$, and $R^1$ attached to one carbon atom of L and $R^2$ attached to the other carbon atom of L, form a $C_3$-$C_7$cycloalkyl or 4- to 7-membered heterocyclyl ring having one or two heteroatoms; wherein said cycloalkyl ring is substituted with 0-3 $R^a$ and said heterocyclyl ring is substituted with 0-4 $R^b$, and $R^a$ and $R^b$ are as defined hereinabove. In this embodiment, preferably L is $-CHR^1CHR^2-$.

In one embodiment, compounds of Formula (I) are provided wherein $R^3$ is hydrogen or $C_1$-$C_6$alkyl, wherein each alkyl is substituted with 0-3 $R^a$ and $R^a$ is as defined hereinabove. Preferably, $R^3$ is hydrogen or $C_1$-$C_4$alkyl, and more preferably hydrogen and $C_1$-$C_2$alkyl. Examples of suitable $R^3$ groups include, but are not limited to, hydrogen and methyl. Still more preferably, $R^3$ is hydrogen.

In one embodiment, compounds of Formula (I) are provided wherein $R^3$ and $R^1$ form a 4- to 7-membered heterocyclyl ring having one or two heteroatoms, wherein the heterocyclyl ring is substituted with 0-4 $R^b$. Examples of suitable heteroatoms include nitrogen, oxygen, and sulfur. The heterocyclyl ring is saturated or partially unsaturated. Preferably, the heterocyclyl ring is saturated. Examples of suitable heterocyclyl rings include 5- to 7-membered heterocyclyl rings such as imidazolyl, pyrrolidinyl, and piperidinyl.

In one embodiment, compounds of Formula (I) are provided wherein $R^4$ is hydrogen or $C_1$-$C_6$alkyl, wherein each alkyl is substituted with 0-3 $R^a$ and $R^a$ is as defined hereinabove. Preferably, $R^4$ is hydrogen or $C_1$-$C_4$alkyl, and more preferably hydrogen and $C_1$-$C_2$alkyl. Examples of suitable $R^4$ groups include, but are not limited to, hydrogen and methyl. Still more preferably, $R^4$ is hydrogen.

In one embodiment, compounds of Formula (I) are provided wherein B is $-OR^5$, $-C(O)OR^5$, $-OC(O)R^5$, or $-OC(O)OR^5$; $R^5$ is hydrogen or $C_1$-$C_6$alkyl; and wherein said alkyl is substituted with 0-3 $R^a$; and $R^a$ is defined hereinabove. Preferably, B is $-OR^5$ or $-C(O)OR^5$; and more preferably, B is $-OH$, $-C(O)OH$, or $-C(O)OCH_2CH_3$. Preferably, $R^5$ is hydrogen or $C_1$-$C_4$alkyl. For example, this embodiment provides compounds of Formula (I) wherein B is —OH, —OCH$_3$, —C(O)OH, —C(O)OCH$_3$, and —C(O)OCH$_2$CH$_3$.

In one embodiment, compounds of Formula (I) are provided wherein R$^6$ is C$_1$-C$_6$alkyl, C$_3$-C$_7$cycloalkyl, aryl, or 1- or 2-ring heterocyclyl; and said alkyl is substituted with 0-3 R$^a$, said cycloalkyl is substituted with 0-4 R$^b$, said aryl is substituted with 0-4 R$^b$, and said heterocyclyl is substituted with 0-4 R$^b$; and R$^a$ and R$^b$ are as defined hereinabove.

In one embodiment, compounds of Formula (I) or are provided wherein A is hydrogen, C$_1$-C$_6$alkyl, C$_3$-C$_7$cycloalkyl, aryl, 1- or 2-ring heterocyclyl, —C(O)R$^6$, —C(O)OR$^6$, or —C(O)NR$^6$R$^7$; R$^6$ is alkyl, cycloalkyl, aryl, or heterocyclyl; and R$^7$ is hydrogen or alkyl, or R$^7$ and R$^6$ together with the nitrogen atom to which they are attached form a 4- to 7-membered heterocyclyl ring having one or two heteroatoms; and each of said alkyl is substituted with 0-3 R$^a$; each of said cycloalkyl is substituted with 0-3 R$^a$; each of said aryl is substituted with 0-4 R$^b$; and each of said heterocyclyl is substituted with 0-4 R$^b$; and R$^a$ and R$^b$ are as defined hereinabove. For example, the present embodiment provides compounds of Formula (I) in which A is a 1- or 2-ring heterocyclyl having 1 or 2 heteroatoms selected from nitrogen and sulfur.

In one embodiment, compounds of Formula (I) are provided wherein: A is hydrogen, C$_1$-C$_6$alkyl, C$_3$-C$_7$cycloalkyl, aryl, 1- or 2-ring heterocyclyl, —C(O)R$^6$, —C(O)OR$^6$, or —C(O)NR$^6$R$^7$; R$^1$ and R$^2$ are, independently at each occurrence, hydrogen, C$_1$-C$_6$alkyl, C$_3$-C$_7$cycloalkyl, aryl, and/or 1- or 2-ring heterocyclyl, or one R$^1$ and one R$^2$ form a C$_3$-C$_7$cycloalkyl or 4- to 7-membered heterocyclyl ring having one or two heteroatoms; R$^3$ is hydrogen or C$_1$-C$_6$alkyl, or R$^3$ and R$^1$ form a 4- to 7-membered heterocyclyl ring having one or two heteroatoms; R$^4$ is hydrogen or C$_1$-C$_6$alkyl; R$^5$ is hydrogen or C$_1$-C$_6$alkyl; R$^6$ is C$_1$-C$_6$alkyl, C$_3$-C$_7$cycloalkyl, aryl, or 1- or 2-ring heterocyclyl; R$^7$ is hydrogen or C$_1$-C$_6$alkyl, or R$^7$ and R$^6$ together with the nitrogen atom to which they are attached form a 4- to 7-membered heterocyclyl ring having one or two heteroatoms; wherein: each alkyl is substituted with 0-3 R$^a$; each cycloalkyl is substituted with 0-3 R$^a$; each aryl is substituted with 0-4 R$^b$; and each heterocyclyl is substituted with 0-4 R$^b$.

In one embodiment, compounds of Formula (I) are provided wherein: A is hydrogen, C$_1$-C$_4$alkyl, phenyl, 1- or 2-ring heterocyclyl having 1- or 2-heteroatoms selected from S and N, —C(O)R$^6$, —C(O)OR$^6$, or —C(O)NR$^6$R$^7$; R$^1$ is hydrogen, C$_1$-C$_6$alkyl, C$_3$-C$_7$cycloalkyl, or phenyl; R$^2$ is hydrogen or methyl; or R$^1$ and R$^2$ form a C$_5$-C$_7$cycloalkyl ring or 5- to 6-membered heterocyclyl ring having one or two heteroatoms; R$^3$ is hydrogen or C$_1$-C$_4$alkyl, or R$^3$ and R$^1$ form a 5- to 7-membered heterocyclyl ring having one or two heteroatoms; R$^4$ is hydrogen or C$_1$-C$_4$alkyl; R$^5$ is hydrogen or C$_1$-C$_4$alkyl; R$^6$ is C$_1$-C$_4$alkyl, or phenyl; and R$^7$ is hydrogen or methyl; wherein: each alkyl is substituted with 0-3 R$^a$; each cycloalkyl is substituted with 0-3 R$^a$; each phenyl is substituted with 0-3 R$^b$; and each heterocyclyl is substituted with 0-3 R$^b$.

In one embodiment, compounds of Formula (I) are provided wherein: A is hydrogen, —C(O)R$^6$, —C(O)OR$^6$, —C(O)NHR$^6$, thiazolyl, or benzothiazolyl; B is —OH or —C(O)OR$^5$; R$^1$ is hydrogen, C$_1$-C$_4$alkyl, C$_5$-C$_7$cycloalkyl, or phenyl; R$^2$ is hydrogen; or R$^1$ and R$^2$ form a C$_5$-C$_7$cycloalkyl; R$^3$ is hydrogen or C$_1$-C$_2$alkyl, or R$^3$ and R$^1$ form a 5- to 6-membered heterocyclyl ring having one heteroatom; R$^4$ is hydrogen or C$_1$-C$_2$alkyl; R$^5$ is hydrogen or C$_1$-C$_4$alkyl; and n is 1 or 2; and each alkyl is substituted with 0-2 R$^a$; each cycloalkyl is substituted with 0-2 R$^a$; each heterocyclyl is substituted with 0-2 R$^b$; each phenyl is substituted with 0-2 R$^b$; each thiazolyl is substituted with 0-2 R$^b$; and each benzothiazolyl is substituted with 0-2 R$^b$; R$^a$ is, independently at each occurrence, F, Cl, Br, —CF$_3$, —OH, —OCH$_3$, —OCF$_3$, phenyl, and/or imidazolyl; and R$^b$ is, independently at each occurrence, C$_1$-C$_4$alkyl, F, Cl, Br, —CF$_3$, —OH, —OCH$_3$, —OCF$_3$, and/or —CN.

In one embodiment, compounds of Formula (I) are provided wherein: A is hydrogen, —C(O)—CH$_2$CH$_3$, —C(O)-benzyl, —C(O)O—CH$_3$, —C(O)O-(butyl), —C(O)NH-(trifluoromethylphenyl), —C(O)NH-(trifluoromethoxyphenyl), thiazolyl, or chlorobenzothiazolyl; B is —OH, —C(O)OH, or —C(O)OCH$_2$CH$_3$; R$^1$ is hydrogen, C$_1$-C$_4$alkyl, hydroxyethyl, cyclohexyl, phenyl, or methyl substituted with phenyl, hydroxyphenyl, or imidazolyl; R$^2$ is hydrogen; or R$^1$ and R$^2$ form a cyclopentyl ring; R$^3$ is hydrogen, or R$^3$ and R$^1$ form a pyrrolidinyl ring; and R$^4$ is hydrogen.

In one embodiment, a compound of Formula (I) or a salt thereof is provided, wherein said compound is:

(2)

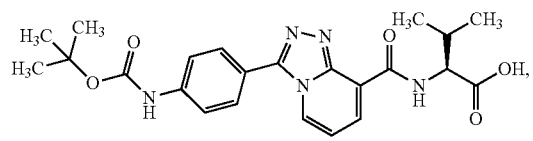

(2A)

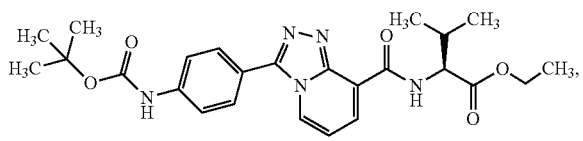

(3)

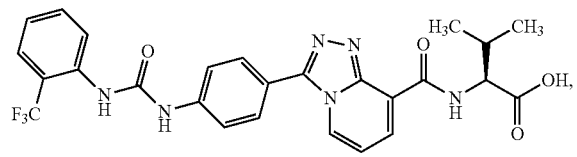

(3A)

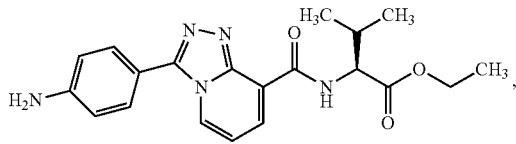

(3B)

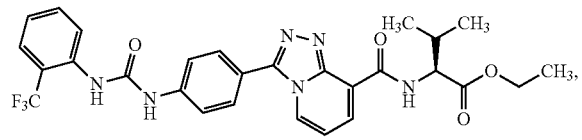

(4)

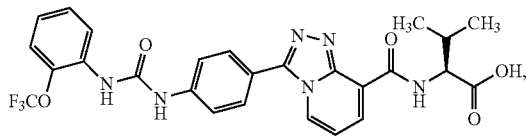

-continued
(5)
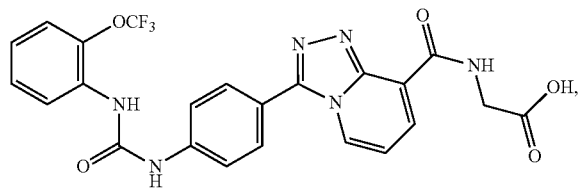
(6)
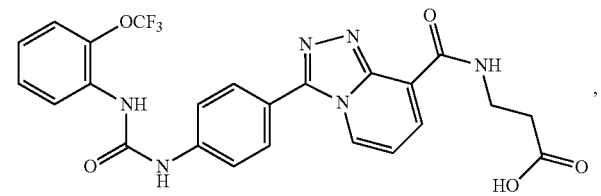
(7)
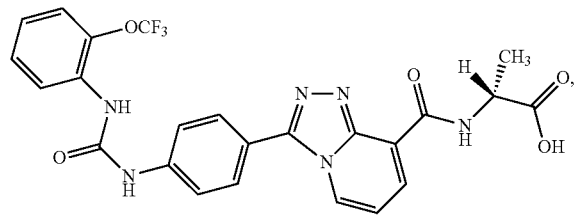
(8)
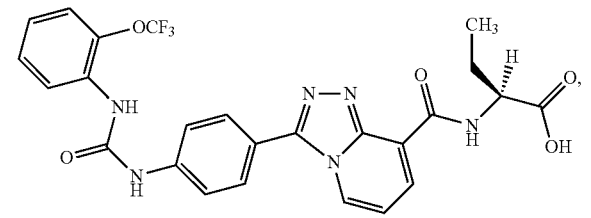
(9)
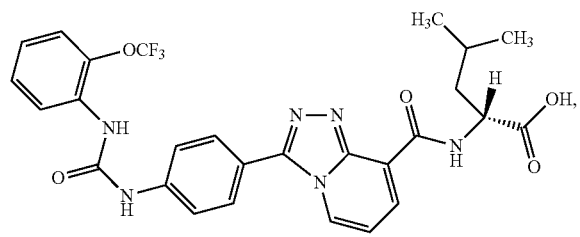
(10)
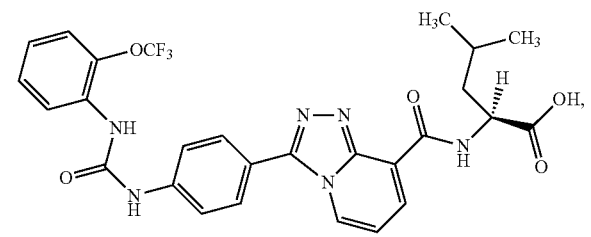
(11)
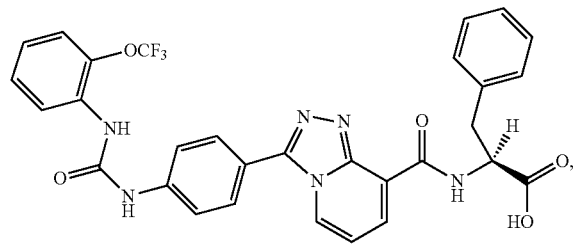
(12)
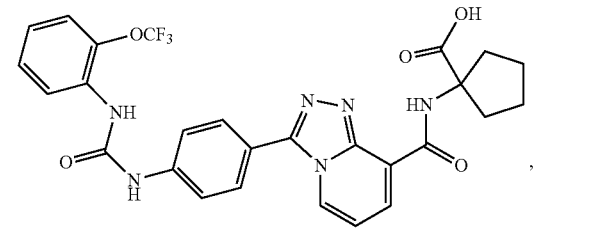
(13)
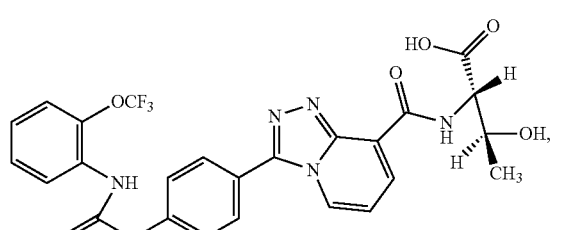
(14)
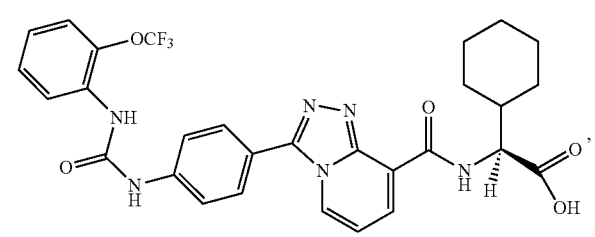
(15)
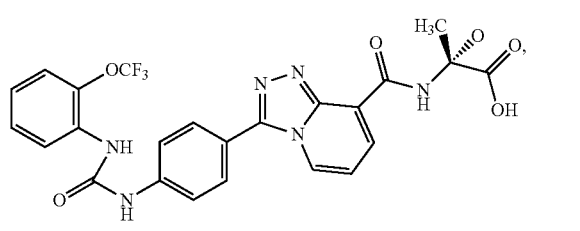
(16)
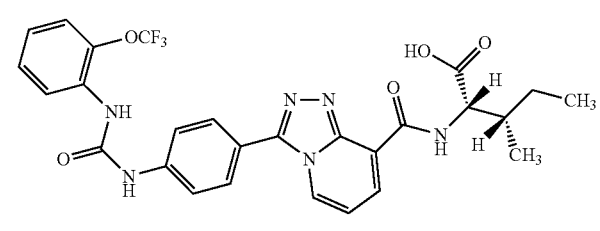

-continued
(17) (18)
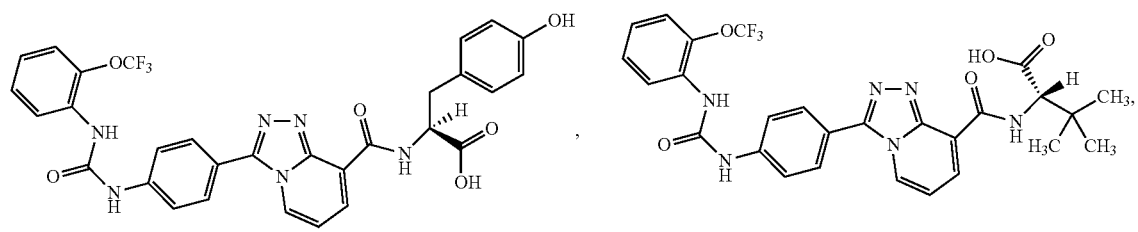
(19) (20)
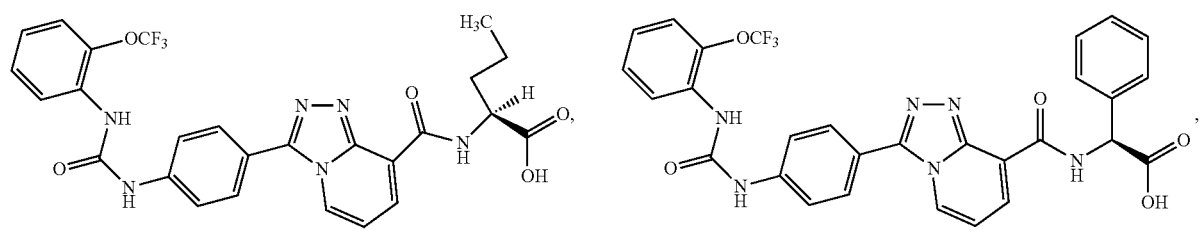
(21) (22)
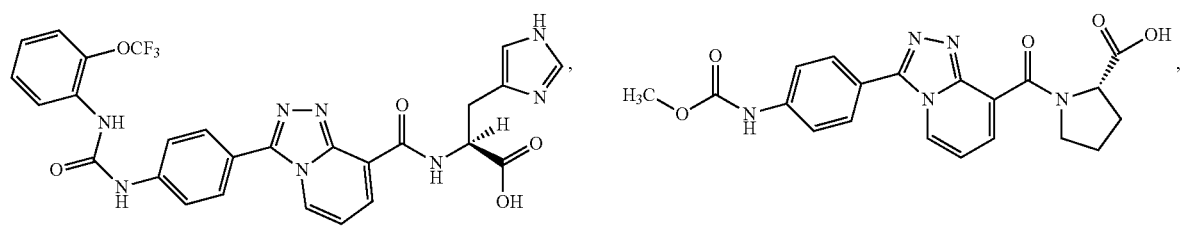
(23) (24)
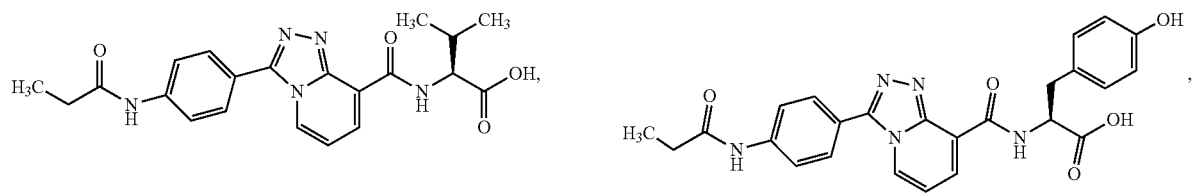
(25) (26)
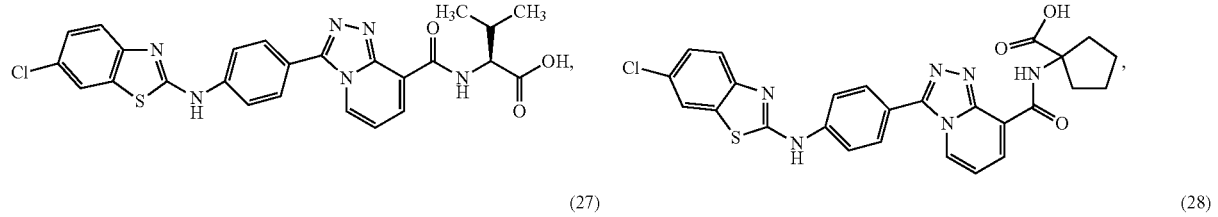
(27) (28)
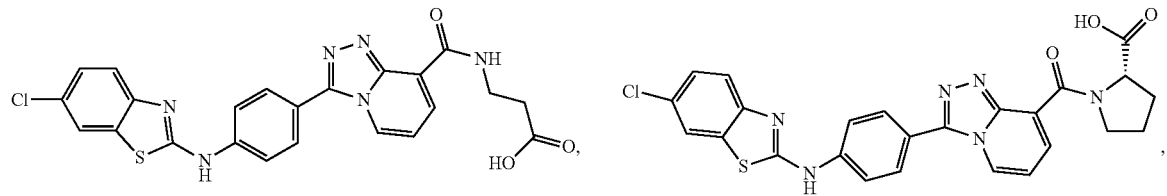
(29) (30)
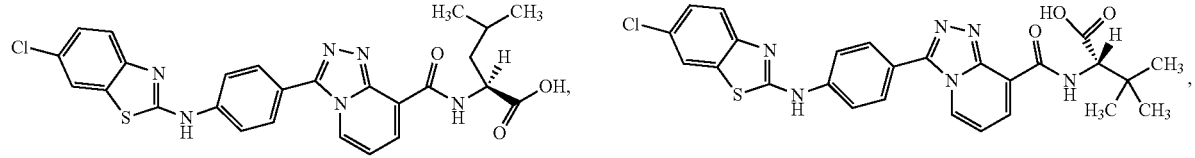

-continued
(31)
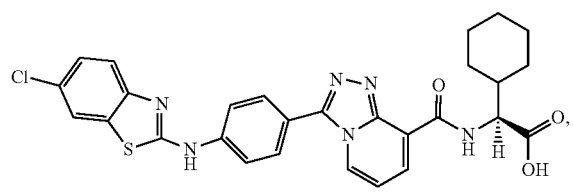
(32)
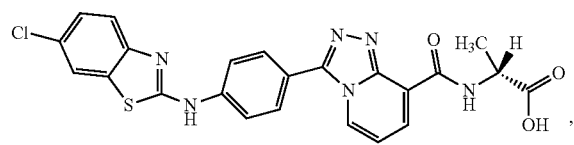
(33)
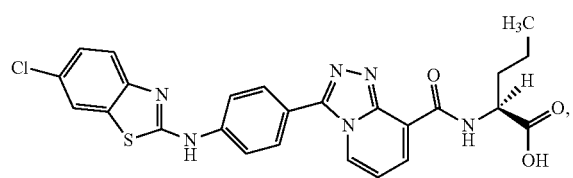
(34)
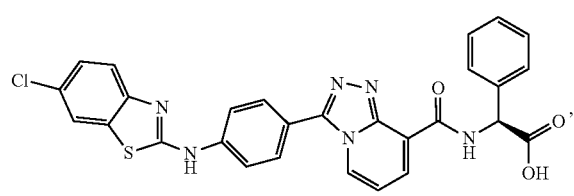
(35)
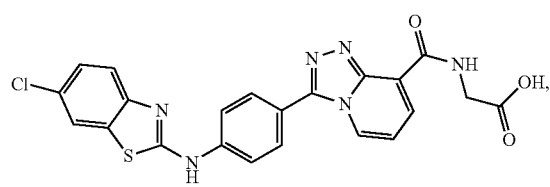
(36)
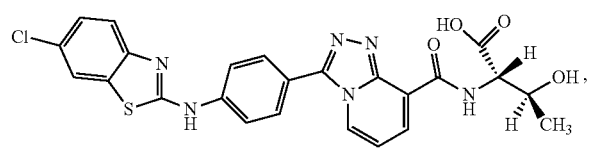
(37)
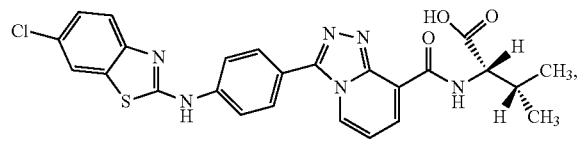
(38)
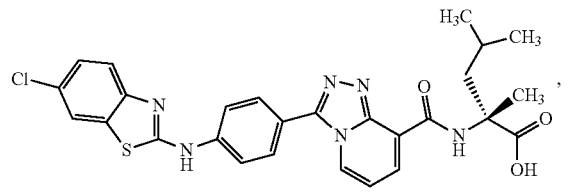
(39)
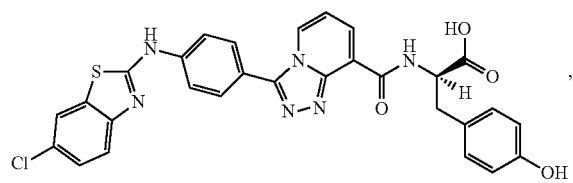
(40)
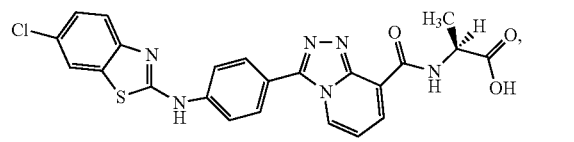
(41)
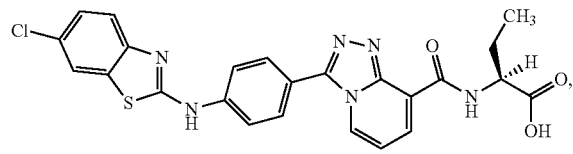
(42)
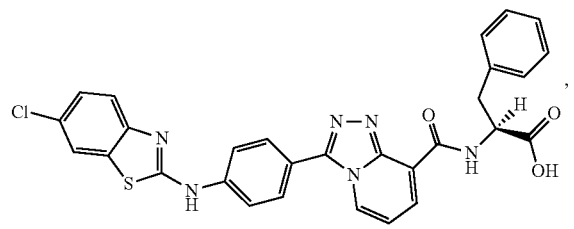
(43)
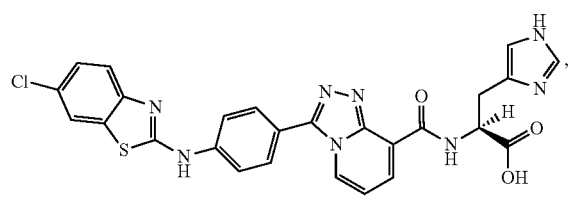
(44)
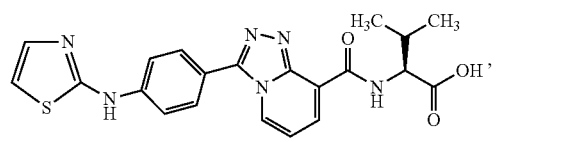

-continued
(45)
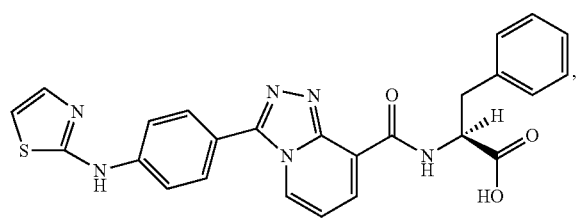
(46)
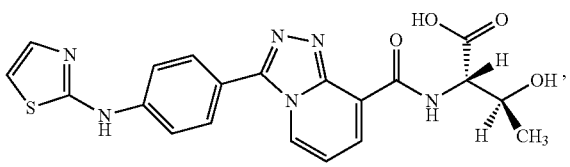
(47)
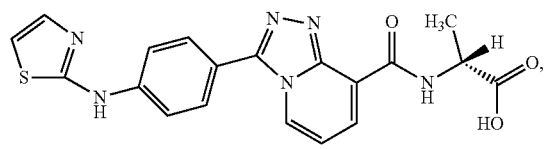
(48)
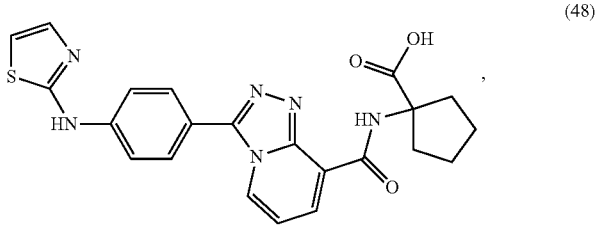
(49)
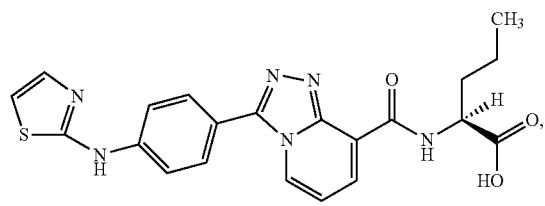
(50)
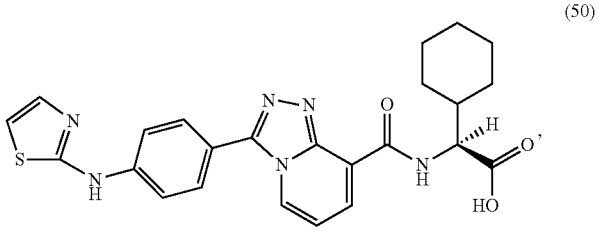
(51)
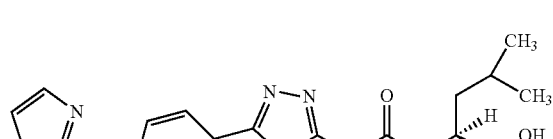
(52)
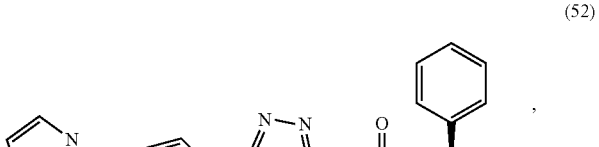
(53)
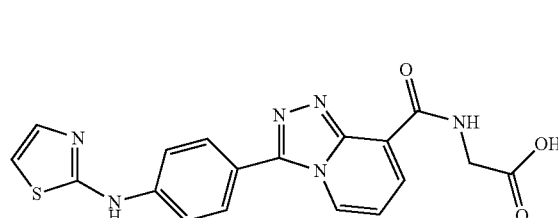
(54)
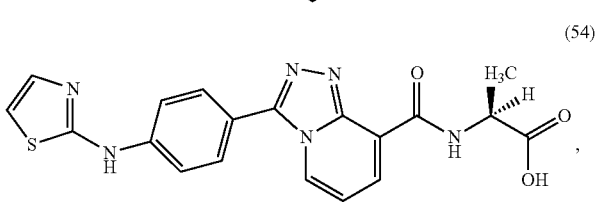
(55)
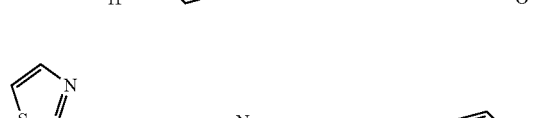
(56)
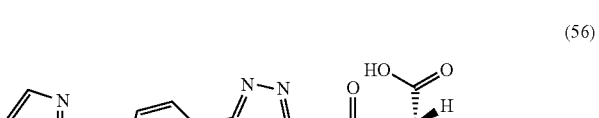
(57)
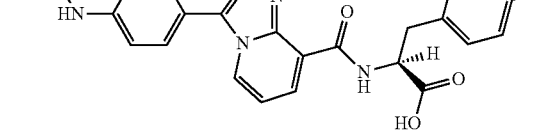
(58)
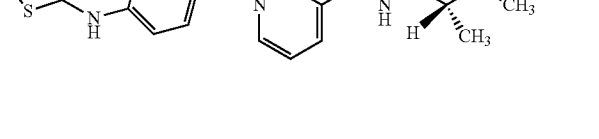

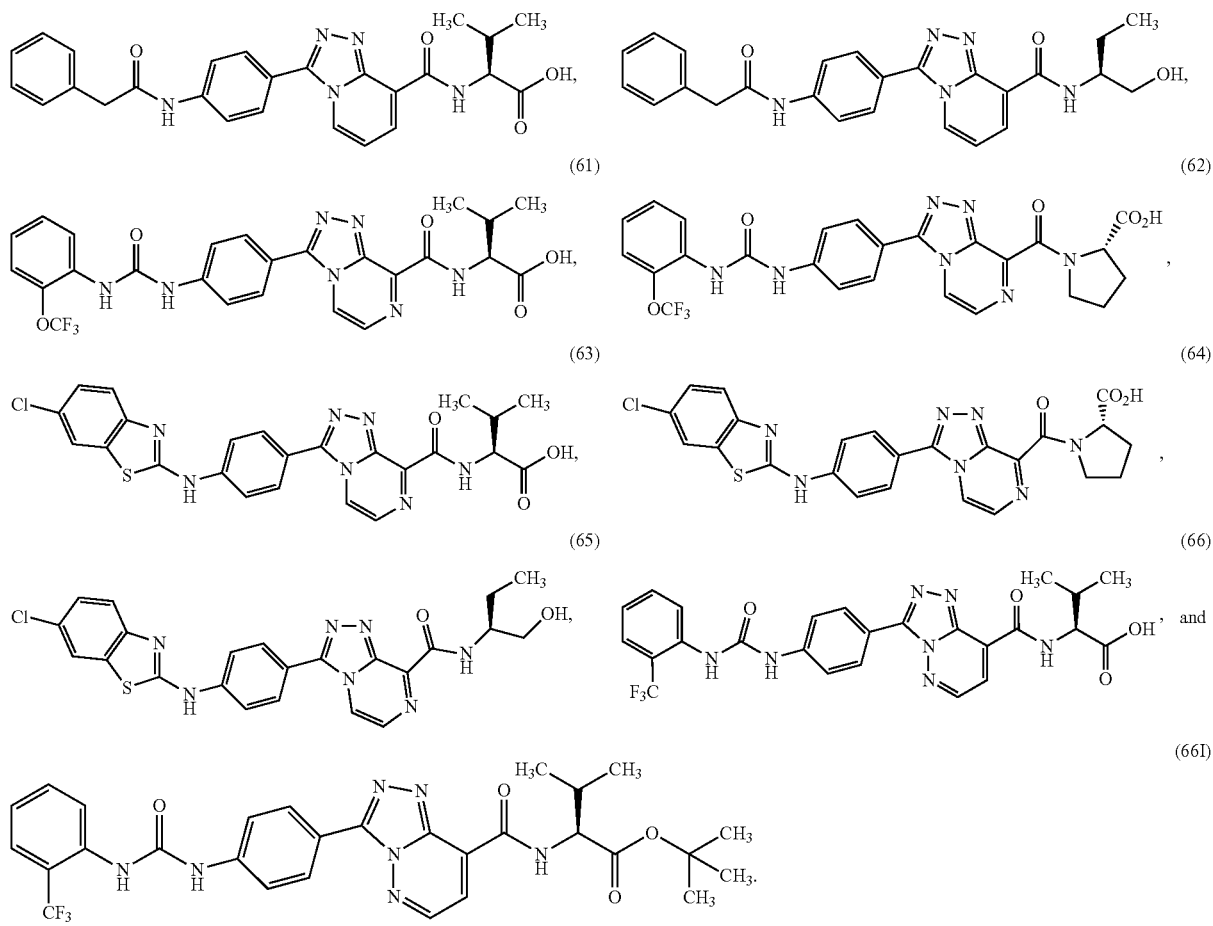

In mammals, there are two biochemical pathways for the synthesis of triacylglycerol: the monoacylglycerol pathway, which happens exclusively in the small intestine (Lehner, R. et al., *Prog. Lipid Res.*, 35:169-201 (1996)), and the glycerol-3-phosphate pathway, which takes place ubiquitously but most notably in the liver and in adipose tissue (Bell, R. M. et al., *Annu. Rev. Biochem.*, 49:459-487 (1980)). The monoacylglycerol pathway initiates from acyl coenzyme A: monoacylglycerol acyl transferase (MGAT) (EC 2.3.1.22). Within minutes of its appearance from the digestion of dietary fat in the lumen of the small intestine, 2-monoacylglycerol is acylated by MGAT to form diacylglycerol. Diacylglycerol is further acylated by acyl coenzyme A: diacylglycerol acyl transferase (DGAT) (EC 2.3.1.20) to re-synthesize triacylglycerol, which is packaged into chylomicron lipoprotein particles that eventually are secreted into the lymph. In the glycerol-3-phosphate pathway, two fatty acyl coenzyme A molecules are added to glycerol-3-phosphate to form phosphatidate. These reactions are followed by the removal of the phosphate group by phosphatidate phosphohydrolase to generate diacylglycerol. Diacylglycerol is then further acylated by DGAT to form triacylglycerol. Collectively, DGAT lies at the final step of both triacylglycerol synthesis pathways.

Two DGAT enzymes have been identified, which are designated as DGAT1 and DGAT2 (Cases, S. et al., *Proc. Natl. Acad. Sci. USA*, 95:13018-13023 (1998)) (Oelkers, P. et al., *J. Biol. Chem.*, 273:26765-26771 (1998)) (Cases, S. et al., *J. Biol. Chem.*, 276:38870-38876 (2001)). Although they carry out identical enzymatic reactions, DGAT1 and 2 are encoded by two different genes that bear little sequence homology. Functionally, these two enzymes might have different physiological importance in vivo. DGAT1 knockout mice exhibit resistance towards becoming obese when challenged with a high fat (Smith, S. J. et al., *Nat. Genet.*, 25:87-90 (2000)). They are physically more active, possess a higher metabolic rate (Chen, H. C. et al., *Trends Cardiovasc. Med.*, 10:188-192 (2000)) and appear to have greater insulin sensitivity (Chen, H. C. et al., *J. Clin. Invest.*, 109:1049-1055 (2002)). In contrast, DGAT2 knockout mice exhibit phenotypes such as lipopenia and skin barrier abnormalities, resulting in death soon after birth (Stone, S. J. et al., *J. Biol. Chem.*, 279:11767-11776 (2004)).

The compounds of the present invention are useful as DGAT modulators, and include compounds which are, for example, activators or inhibitors of DGAT enzyme. Accordingly, the compounds of the present invention may be useful for the treatment or prevention of diseases and disorders associated with DGAT enzyme activities. Preferably, compounds of the present invention possess activity as inhibitors of DGAT enzyme activities, and may be used in the treatment of diseases or disorders associated with the activity of the DGAT enzyme.

The compounds of the present invention or stereoisomers or pharmaceutically acceptable salts thereof can be administered to mammals, preferably humans, for the treatment of a variety of conditions and disorders, including, but not limited to metabolic as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

The compounds of the present invention can possess both DGAT and ACAT inhibitory activities. ACAT inhibition is a known mechanism to provide hypolipidemic effects (which also has anti-atherosclerosis activity) such as disclosed in, *Drugs of the Future,* 24:9-15 (1999) (Avasimibe); Nicolosi et al., "The ACAT inhibitor, Cl-1011 is effective in the prevention and regression of aortic fatty streak area in hamsters", *Atherosclerosis* (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.,* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways,* CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.,* 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.,* 8(6):359-362 (1995), or TS-962 (Taisho Pharmaceutical Co. Ltd.), as well as F-1394, CS-505, F-12511, HL-004, K-10085 and YIC-C8-434.

The present invention relates to the use of a DGAT inhibitor in the treatment of appetitive or motivational disorders that regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention further relates to the use of a DGAT inhibitor for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulimia, polycystic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

As modulators of the DGAT enzyme, the compounds of the present invention are further useful for the treatment and prevention of respiratory diseases and disorders. Respiratory diseases for which DGAT modulators are useful include, but are not limited to, chronic pulmonary obstructive disorder, emphysema, asthma, and bronchitis. In addition, DGAT modulators block the activation of lung epithelial cells by moieties such as allergic agents, inflammatory cytokines or smoke, thereby limiting release of mucin, cytokines, and chemokines, or selectively inhibiting lung epithelial cell activation.

DGAT is important in the regulation of TNF alpha of adipocytes. Compounds of the present invention are especially of value, for example, in treating obesity associated inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

In one embodiment, a method is provided for treatment of a condition or disorder comprising administering to a patient in need thereof at least one compound of Formula (I) wherein said condition or disorder is obesity, dyslipidemia, diabetes, or atherosclerosis. Preferred compounds useful in the method of the present embodiment include compounds of Formula (I) wherein:

A is hydrogen, $C_1$-$C_6$alkyl, $C_3$-$C_7$cycloalkyl, aryl, 1- or 2-ring heterocyclyl, —C(O)$R^6$, —C(O)O$R^6$, or —C(O)N$R^6R^7$; L is —(C$R^1R^2$)$_n$—; n is 1, 2, or 3; B is —O$R^5$, —C(O)O$R^5$, —OC(O)$R^5$, or —OC(O)O$R^5$; $R^1$ and $R^2$ are, independently at each occurrence, hydrogen, $C_1$-$C_6$alkyl, $C_3$-$C_7$cycloalkyl, aryl, and/or 1- or 2-ring heterocyclyl, or one $R^1$ and one $R^2$ form a $C_3$-$C_7$cycloalkyl or 4- to 7-membered heterocyclyl ring having one or two heteroatoms; $R^3$ is hydrogen or $C_1$-$C_6$alkyl, or $R^3$ and $R^1$ form a 4- to 7-membered heterocyclyl ring having one or two heteroatoms; $R^4$ is hydrogen or $C_1$-$C_6$alkyl; $R^5$ is hydrogen or $C_1$-$C_6$alkyl; $R^6$ is $C_1$-$C_6$alkyl, $C_3$-$C_7$cycloalkyl, aryl, or 1- or 2-ring heterocyclyl; $R^7$ is hydrogen or $C_1$-$C_6$alkyl, or $R^7$ and $R^6$ together with the nitrogen atom to which they are attached form a 4- to 7-membered heterocyclyl ring having one or two heteroatoms; wherein: each alkyl is substituted with 0-3 $R^a$; each cycloalkyl is substituted with 0-3 $R^a$; each aryl is substituted with 0-4 $R^b$; and each heterocyclyl is substituted with 0-4 $R^b$; $R^a$ is, independently at each occurrence, F, Cl, Br, —CF$_3$, —OH, —OCH$_3$, —OCF$_3$, —CN, —N$R^cR^d$, phenyl, imidazolyl, and/or $C_1$-$C_3$alkoxy; $R^a$ is, independently at each occurrence, $C_1$-$C_4$alkyl, F, Cl, Br, —CF$_3$, —OH, —OCH$_3$, —OCF$_3$, —CN, —N$R^cR^d$, and/or $C_1$-$C_3$alkoxy; and $R^c$ and $R^d$ are, independently at each occurrence, H and/or $C_1$-$C_4$alkyl. Preferably, the method of this embodiment is used to treat obesity. Preferably, the patient is a human. Preferably, a therapeutically effective amount of the compound of Formula (I) or stereoisomer or a pharmaceutically acceptable salt thereof is administered in the method of this embodiment.

In one embodiment, the use of a compound of Formula (I) in the manufacture of a medicament for the treatment of a condition or disorder is provided, wherein the condition or disorder is obesity, dyslipidemia, diabetes, or atherosclerosis. Preferably, the condition or disorder is obesity.

In one embodiment, the use of a compound of Formula (I) in the manufacture of a medicament for the treatment of a condition or disorder is provided, wherein the condition or disorder is treatable by modulation of the DGAT1 enzyme. The modulation can be activation or inhibition of the DGAT1 enzyme. Preferably, the condition or disorder is treatable by inhibition of the DGAT1 enzyme. Conditions or disorder treatable by the DGAT1 enzyme include, but are not limited to, obesity, dyslipidemia, diabetes, or atherosclerosis. Preferably, the condition or disorder treated by inhibition of the DGAT1 enzyme is obesity.

In one embodiment, a method is provided for treating a condition or disorder in a patient wherein the condition or disorder is dependent upon DGAT1 inhibition, comprising administering to the patient a compound of Formula (I). The method of this embodiment can be used to treat conditions or disorders including obesity, dyslipidemia, diabetes, or atherosclerosis. Preferably, the condition or disorder is obesity. Preferably, a therapeutically effective amount of the compound of Formula (I) is administered in the method of this embodiment.

In one embodiment, the present invention provides a compound of the present invention for use in therapy.

The present invention includes within its scope pharmaceutical compositions comprising, as an active ingredient, a therapeutically effective amount of at least one of the compounds of Formula (I) or a pharmaceutically acceptable salt thereof alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; agents used to treat eating disorders, cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents. Such other therapeutic agent(s) may be administered prior to, simultaneously with, or following the administration of the DGAT inhibitors in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, amylin receptor modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/ AXOKINE® (Regeneron), BDNF (brain-derived neurotrophic factor), leptin and leptin receptor modulators, or cannabinoid-1 (CB1) receptor antagonists, such as SR-141716 (Sanofi), MK-0364 (Merck), CP-945,598 (Pfizer) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DPP4) inhibitors, SGLT2 inhibitors, glucokinase inhibitors, AMP kinase modulators, glycogen phosphorylase inhibitors, and/or meglitinides, as well as insulin, and/or glucagon-like peptide-1 (GLP-1), GLP-1 agonist, and/or a PIP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W, et al., *J. Am. Chem. Soc.*, 109:5544 (1987) and cyclopropanes reported by Capson, T. L., PhD dissertation, June, 1987, Dept. Med. Chem. U of Utah, Abstract, Table of Contents, pp. 16, 17, 40-43, 48-51, Summary.

Other hypolipidemic agents suitable for use herein include, but are not limited to, fabric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAF-Sephadex (SEC-HOLEX®, policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/A11 antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

DGAT inhibitors could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, naproxen, CELEBREX®, VIOXX®), CTLA4-Ig agonists/antagonists, CD40 ligand antagonists, IMPDH inhibitors, such as mycophenolate (CELLCEPT®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (ENBREL®), rapamycin (sirolimus or RAPAMUNE®) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., ZELNORM® and Maxi-K openers such as those disclosed in U.S. Pat. No. 6,184,231 B1).

The above other therapeutic agents, when employed in combination with the compounds of the present invention, may be used, for example, in those amounts indicated in the Physicians' Desk Reference (PDR) or as otherwise determined by one of ordinary skill in the art.

Also embraced within this invention is a class of pharmaceutical compositions comprising the compound of Formula (I) or a stereoisomer or a pharmaceutically acceptable salt thereof in association having one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

The compounds of the present invention can be administered to various mammalian species known to be subject to such maladies, e.g., humans, in an effective amount up to 1 gram, preferably up to 200 mg, more preferably up to 100 mg in a regimen of single, two or four divided daily doses.

The compounds of the Formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of the present invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The compounds of the present invention can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed in the Schemes, Examples and elsewhere herein:
AcOH=acetic acid
DCM=dichloromethane
DIPEA=diisopropylethylamine
DMF=N,N-dimethylformamide
DMSO=dimethyl sulfoxide
Dppp=(R)-(+)-1,2-bis(diphenylphosphino)propane
EDC=N-(3-dimethylaminopropyl)-N'-ethylcarbodiimide
EtOAc=ethyl acetate
EtOH=ethanol
Et$_3$N=triethylamine
Et$_2$O=diethyl ether
HCl=hydrogen chloride
HOBt=1-hydroxybenzotriazole
HPLC or LC=high performance liquid chromatography
K$_3$PO$_4$=potassium phosphate tribasic
K$_2$CO$_3$=potassium carbonate
LiOH=lithium hydroxide
MeOH=methanol
MS or Mass Spec=mass spectrometry
NaCl=sodium chloride
NaHCO$_3$=sodium bicarbonate
Na$_2$CO$_3$=sodium carbonate
Na$_2$SO$_4$=sodium sulfate
NaOH=sodium hydroxide
Pd(OAc)$_2$=palladium(II) acetate
Ph$_3$PCl$_2$=triphenylphosphine dichloride
PG=protecting group
POCl$_3$=phosphorus oxychloride
Pd(dppf)Cl$_2$=[1,1'-bis(diphenylphosphino)-ferrocene]dichloropalladium(II)
TFA=trifluoroacetic acid
THF=tetrahydrofuran
min=minute(s)
h=hour(s)
L=liter
mL=milliliter
μL=microliter
g=gram(s)
mg=milligram(s)
mol=moles
mmol=millimole(s)
nM=nanomolar Compounds of the present invention may be prepared by procedures illustrated in the accompanying schemes.

Methods of Preparation

The compounds of the present invention can be prepared in a number of ways known to one skilled in the art of organic synthesis. The compounds of the present invention may be prepared by the methods described below, other with synthetic methods known in the art of synthetic organic chemistry, or by variations thereon as appreciated by those skilled in the art. The reactions are performed in a solvent or solvent mixture appropriate to the reagents and materials employed and suitable for the transformation being effected. It will be understood by those skilled in the art of organic synthesis that the functionality present on the molecule should be consistent with the transformation proposed. This will sometimes require a judgment to modify the order of the synthetic steps or to select one particular process scheme over another in order to obtain a desired compound of the invention.

The compounds of the present invention can be prepared according to the general methods shown in the schemes below. Solvents, temperatures, pressures, and other reaction conditions may readily be selected by one of ordinary skill in the art. Starting materials are commercially available or can be readily prepared by one of ordinary skill in the art using known methods. For the scheme and compounds described below, A, B, L, R$^3$, and R$^4$ are as described for a compound of Formula (I).

The following are the definitions of symbols used throughout Schemes 1, 2, 3 and 4:

PG is a suitable nitrogen protecting group, exemplified by benzyl, tert-butoxycarbonyl-[BOC], benzyloxycarbonyl-[CBZ], or 9-fluorenylmethoxycarbonyl-[FMOC].

LG is a leaving group exemplified by halogen (Cl, Br, I) and sulfonates (—OSO$_2$-aryl (e.g., —OSO$_2$Ph or —OSO$_2$PhCH$_3$), or —OSO$_2$-alkyl (e.g., —OSO$_2$CH$_3$ or —OSO$_2$CF$_3$)).

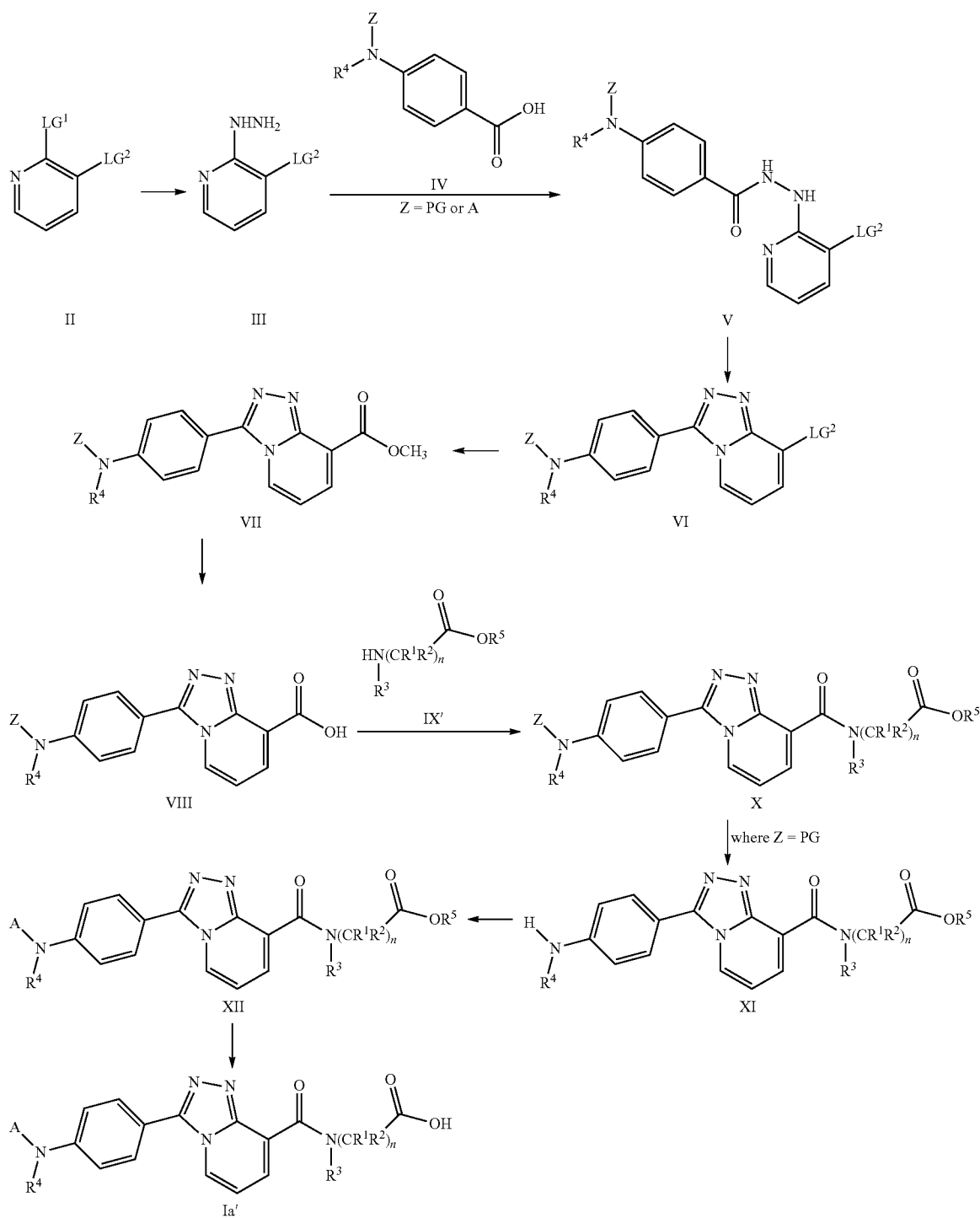

Scheme 1

Compounds of formula Ia' (with triazolopyridine core) can be prepared as described in Scheme 1.

Compounds of formula II are either commercially available or available by means known to one skilled in the art. Compounds of formula III can be prepared by reacting compounds of formula II with anhydrous hydrazine in a polar solvent, such as 1,4-dioxane or pyridine at elevated temperature. Compounds of formula V can be prepared by reacting compounds of formula III with a compound of formula IV in the presence of a coupling agent, such as N-[3-(dimethylaminopropyl)-N'-ethylcarbodiimide. Compounds of formula IV (where Z is an N-protecting group (PG) or a functional group (A) as defined in the claims) are either commercially available or available by means known to one skilled in the art. Compounds of formula VI can be prepared by reacting compounds of formula V with a dehydrating agent, such as a mixed solvent of ethanol and acetic acid at elevated temperature, or dichlorotriphenylphosphorane in the presence of a base, such as diisopropylethylamine. Compounds of formula VII can be prepared by reacting compounds of formula VI with carbon monoxide and methanol in a pressured vessel at elevated temperature in the presence of a palladium catalyst and a ligand, such as palladium acetate and (R)-(+)-1,2-bis(diphenylphosphino)propane. Compounds of formula VIII can be prepared by saponification of compounds of formula VII in aqueous THF in the presence of a base, such as lithium hydroxide. Compounds of formula X can be prepared by reaction of compounds of formula VIII with an amino acid ester IX' in the presence of a coupling agent, such as N-[3-(dimethylaminopropyl)-N'-ethylcarbodiimide. Compounds of formula X where Z is an N-protecting group (PG) can be converted to compounds of formula XI by the methods described in Greene, T. W. et al., *Protecting Groups in Organic Synthesis*, John Wiley & Sons, Inc, New York (1991). Compounds of formula XII where A is $R^6(CO)$— can be prepared by acylation of compounds of formula XI with an acyl chloride or anhydride in the presence of a base, such as triethylamine. Compounds of formula XII where A is $R^6O(CO)$— can be prepared by reaction of compounds of formula XI with a chloroformate in the presence of a base, such as triethylamine. Compounds of formula XII where A is $R^6N(CO)$— can be prepared by reaction of compounds of formula XI with an isocyanate in the presence of a base, such as triethylamine. Compounds of formula Ia' (where B is a carboxylic acid) can be prepared by saponification of compounds of formula XII in aqueous THF in the presence of a base, such as lithium hydroxide, followed by acidification.

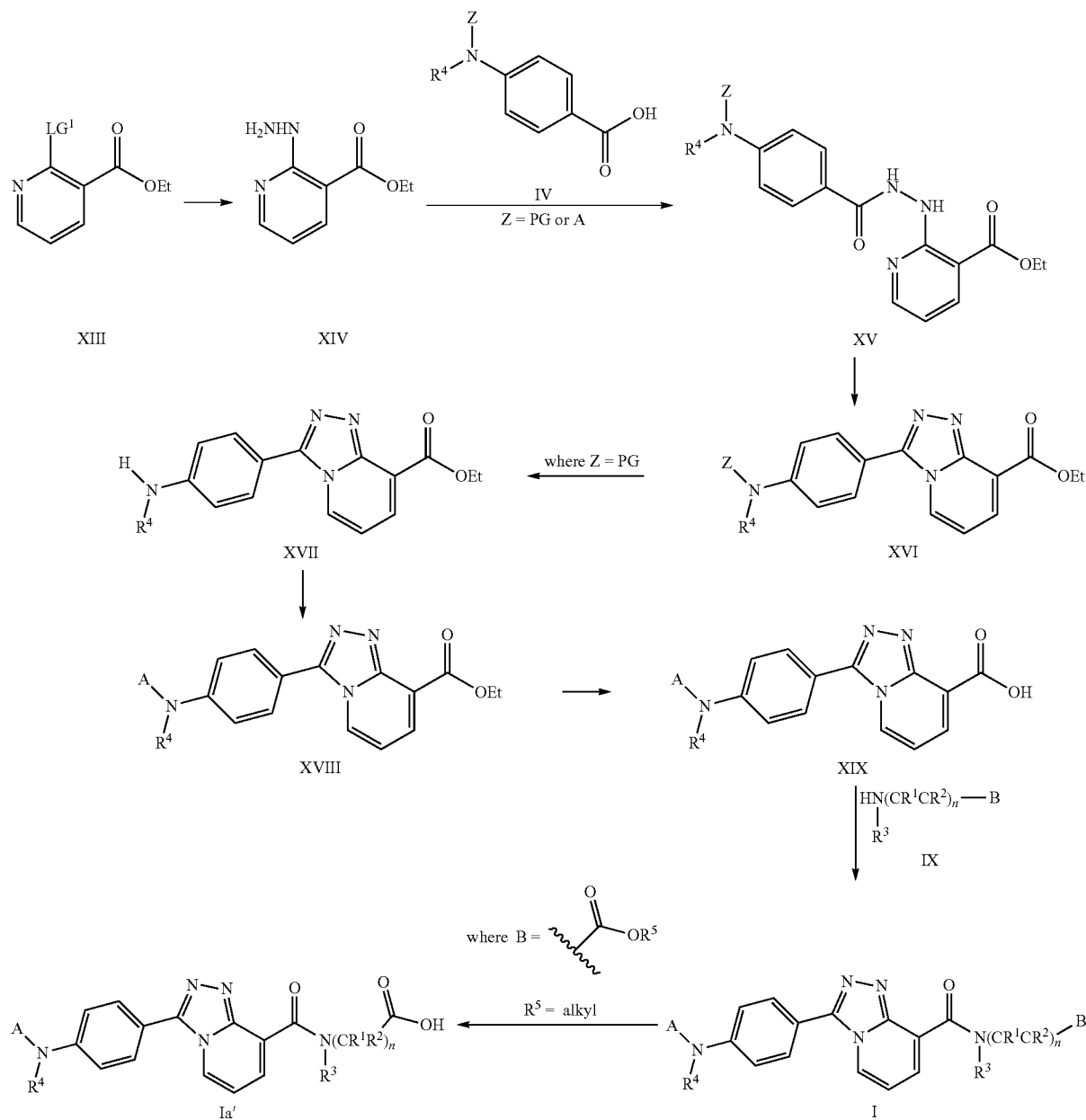

Alternatively, compounds of formula Ia and Ia' (with triazolopyridine core) can be prepared as described in Scheme 2 starting from compounds of formula XIII, which are either commercially available or available by means known to one skilled in the art.

Compounds of formula XIV can be prepared by reacting compounds of formula XIII with anhydrous hydrazine in a polar solvent, such as 1,4-dioxane or pyridine at elevated temperature. Compounds of formula XV can be prepared by reacting compounds of formula XIV with a compound of formula IV in the presence of a coupling agent, such as N-[3-(dimethylaminopropyl)-N'-ethylcarbodiimide. Compounds of formula XVI can be prepared by reaction of compounds of formula XV with a dehydrating agent, such phosphorus oxychloride at elevated temperature, or dichlorotriphenylphosphorane in the presence of a base, such as diisopropylethylamine. Compounds of formula XVI where Z is an N-protecting group (PG) can be converted to compounds of formula XVII by the methods described in Greene, T. W. et al., *Protecting Groups in Organic Synthesis*, John Wiley & Sons, Inc, New York (1991). Compounds of formula XVIII where A is $R^6(CO)-$ can be prepared by acylation of compounds of formula XVII with an acyl chloride or anhydride in the presence of a base, such as triethylamine. Compounds of formula XVIII where A is $R^6O(CO)-$ can be prepared by reaction of compounds of formula XVII with a chloroformate in the presence of a base, such as triethylamine. Compounds of formula XVIII where A is $R^6N(CO)-$ can be prepared by reaction of compounds of formula XVII with an isocyanate in the presence of a base, such as triethylamine. Compounds of formula XIX can be prepared by saponification of compounds of formula XVIII in aqueous THF in the presence of a base, such as lithium hydroxide, followed by acidification. Compounds of formula I can be prepared by reaction of compounds of formula XIX with an amino acid ester or an aminoalcohol IX in the presence of a coupling agent, such as N-[3-(dimethylaminopropyl)-N' ethylcarbodiimide. Compounds of formula Ia' (where B is a carboxylic acid) can be prepared by saponification of compounds of formula Ia (where B is $-CO_2R^5$ and $R^5$ is an alkyl group) in aqueous THF in the presence of a base, such as lithium hydroxide, followed by acidification.

Scheme 3

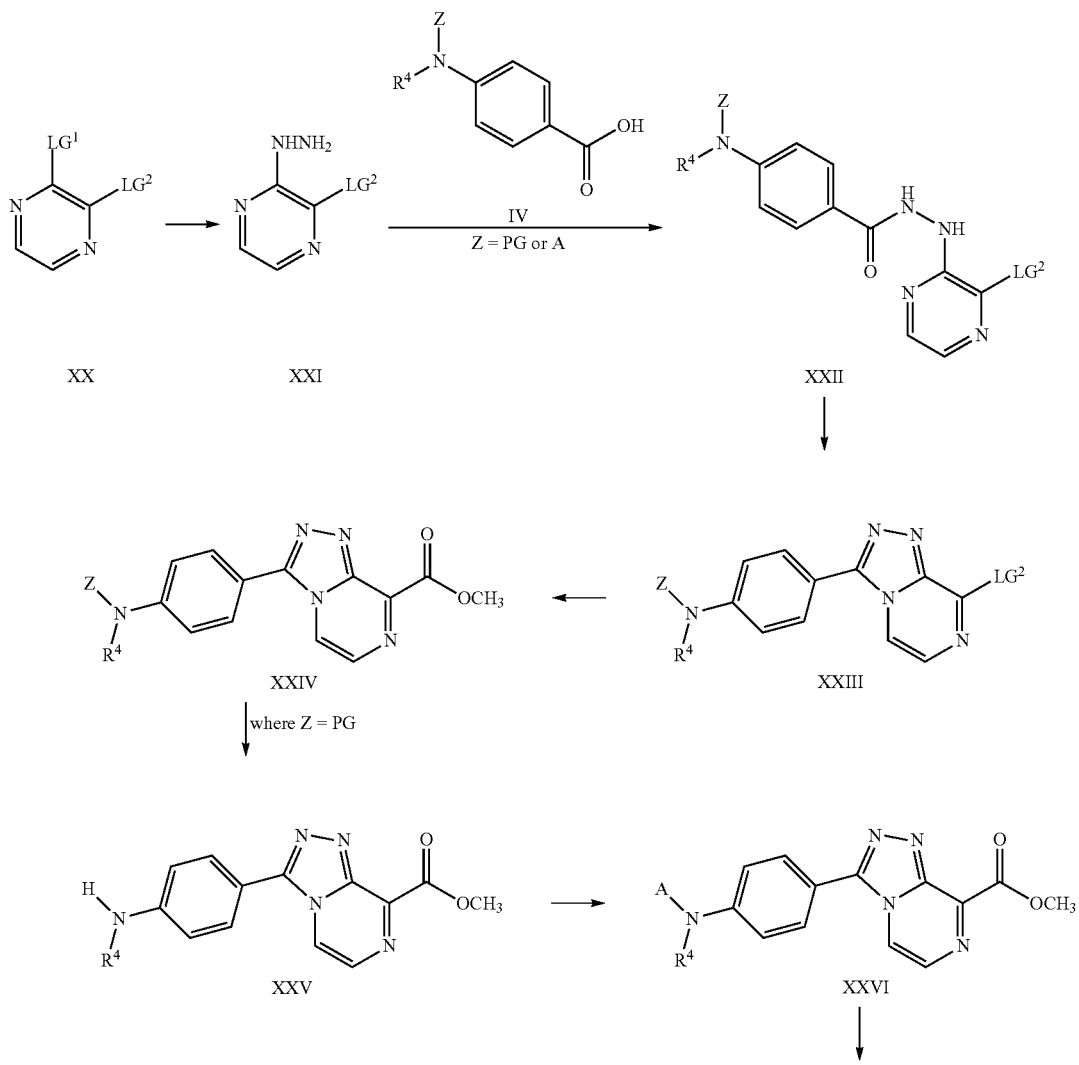

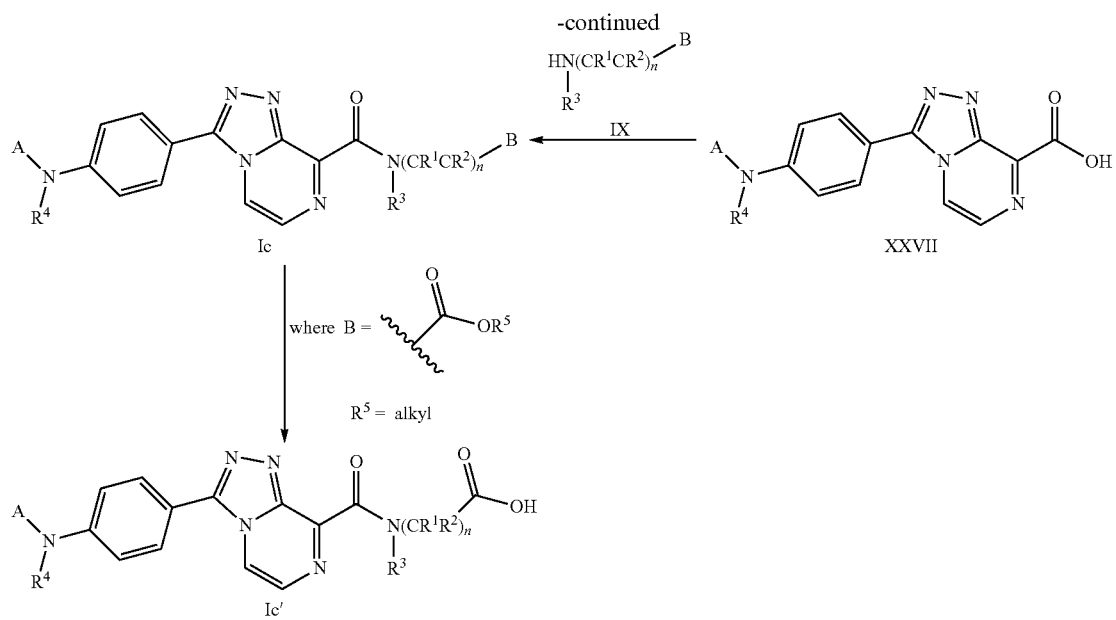

Compounds of formula Ic and Ic' (with triazolopyrazine core) can be prepared as described in Scheme 3.

Compounds of formula XX are either commercially available or available by means known to one skilled in the art. Compounds of formula XXI can be prepared by reacting compounds of formula XX with anhydrous hydrazine in a polar solvent, such as 1,4-dioxane or pyridine at elevated temperature. Compounds of formula XXII can be prepared by reacting compounds of formula XXI with a compound of formula IV in the presence of a coupling agent, such as N-[3-(dimethylaminopropyl)-N'-ethylcarbodiimide. Compounds of formula XXIII can be prepared by reacting compounds of formula XXII with a dehydrating agent, such as phosphorus oxychloride at elevated temperature, or a phosphonium salt (e.g., triethylphosphine/carbon tetrachloride) in the presence of a base, such as diisopropylethylamine. Compounds of formula XXIV can be prepared by reacting compounds of formula XXIII with carbon monoxide and methanol in a pressured vessel at elevated temperature in the presence of a palladium catalyst and a ligand, such as palladium acetate and (R)-(+)-1,2-bis(diphenylphosphino)propane. Compounds of formula XXIV where Z is an N-protecting group can be converted to compounds of formula XXV by the methods described in Greene, T. W. et al., *Protecting Groups in Organic Synthesis*, John Wiley & Sons, Inc, New York (1991). Compounds of formula XXVI where A is $R^6(CO)$— can be prepared by acylation of compounds of formula XXV with an acyl chloride or anhydride in the presence of a base, such as triethylamine. Compounds of formula XXVI where A is $R^6O(CO)$— can be prepared by reaction of compounds of formula XXV with a chloroformate in the presence of a base, such as triethylamine. Compounds of formula XXVI where A is $R^6N(CO)$— can be prepared by reaction of compounds of formula XXV with an isocyanate in the presence of a base, such as triethylamine. Compounds of formula XXVII can be prepared by saponification of compounds of formula XXVI in aqueous THF in the presence of a base, such as lithium hydroxide. Compounds of formula I can be prepared by reaction of compounds of formula XXVII with an amino acid ester or an aminoalcohol IX in the presence of a coupling agent, such as N-[3-(dimethylaminopropyl)-N'-ethylcarbodiimide. Compounds of formula Ic' (where B is a carboxylic acid) can be prepared by saponification of compounds of formula Ic (where B is —$COOR^5$ and $R^5$ is an alkyl group) in aqueous THF in the presence of a base, such as lithium hydroxide, followed by acidification.

Scheme 4

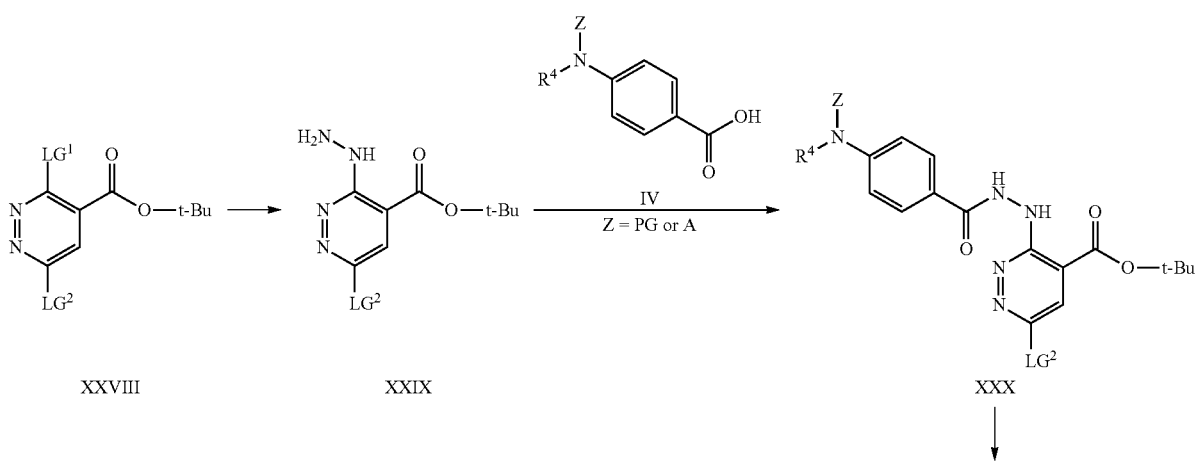

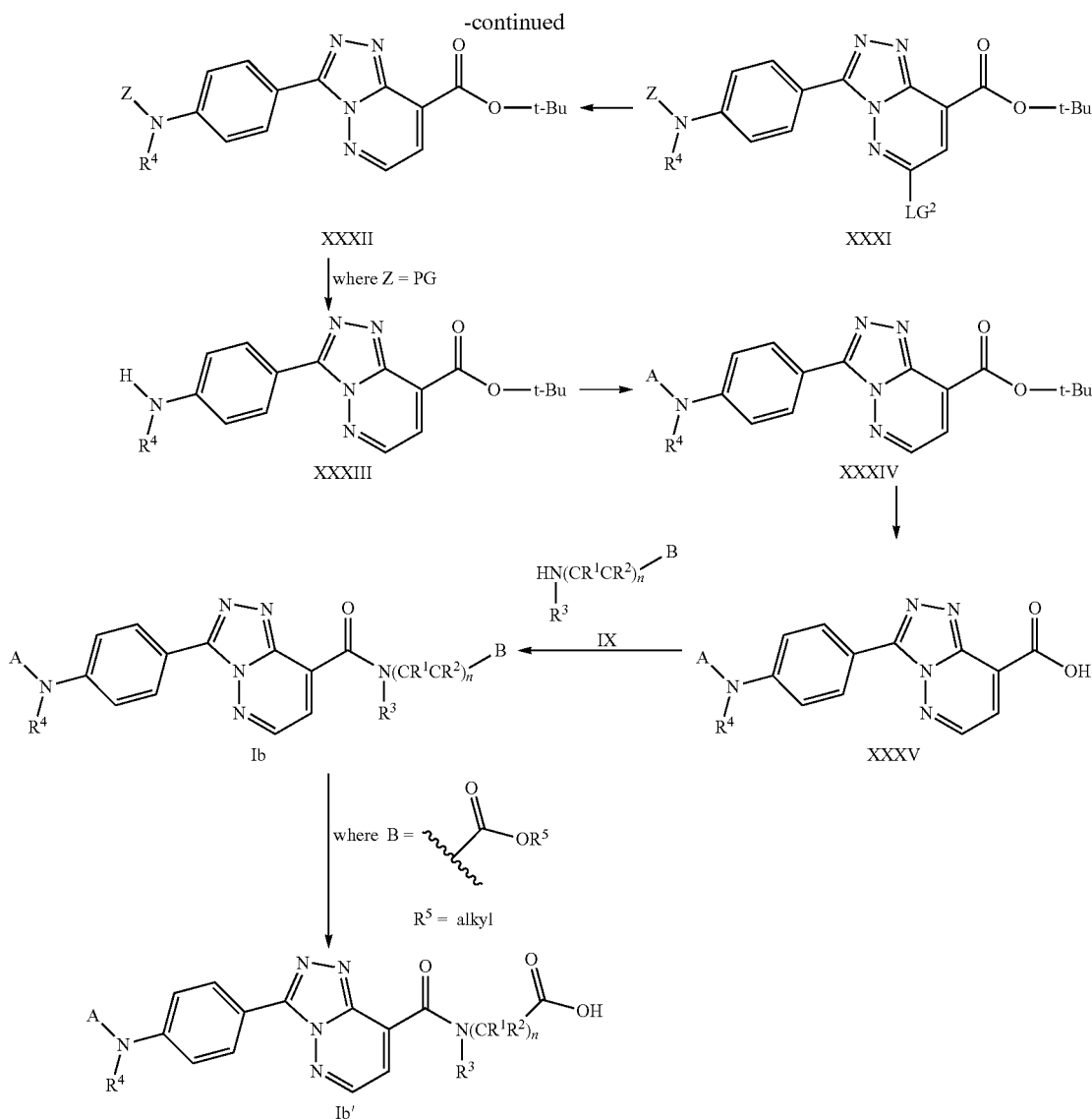

Compounds of formula Ib and Ib' (with triazolopyridazine core) can be prepared as described in Scheme 4.

Compounds of formula XXVIII are either commercially available or available by means known to one skilled in the art. Compounds of formula XXIX can be prepared by reacting compounds of formula XXVIII with anhydrous hydrazine in a polar solvent, such as ethanol at room temperature. Compounds of formula XXX can be prepared by reacting compounds of formula XXIX with a compound of formula IV in the presence of a coupling agent, such as N-[3-(dimethylaminopropyl)-N'-ethylcarbodiimide. Compounds of formula XXXI can be prepared by reacting compounds of formula XXX with a dehydrating agent, such as triethylphosphine/carbon tetrachloride in the presence of a base (e.g., diisopropylethylamine). Compounds of formula XXXI (where $LG^2$ is chlorine) can be converted to compounds of formula XXXII by dechlorination under hydrogenolysis conditions in the presence of a palladium catalyst. Compounds of formula XXXI where Z is an N-protecting group can be converted to compounds of formula XXXIII by the methods described in Greene, T. W. et al., *Protecting Groups in Organic Synthesis*, John Wiley & Sons, Inc, New York (1991). Compounds of formula XXXIV where A is $R^6(CO)$— can be prepared by acylation of compounds of formula XXXIII with an acyl chloride or anhydride in the presence of a base, such as triethylamine. Compounds of formula XXXIV where A is $R^6O(CO)$— can be prepared by reaction of compounds of formula XXXIII with a chloroformate in the presence of a base, such as triethylamine. Compounds of formula XXXIV where A is $R^6N(CO)$— can be prepared by reaction of compounds of formula XXXIII with an isocyanate in the presence of a base, such as triethylamine. Compounds of formula XXXV can be prepared by treating compounds of formula XXXIV with trifluoroacetic acid. Compounds of formula I can be prepared by reaction of compounds of formula XXXV with an amino acid ester or an aminoalcohol IX in the presence of a coupling agent, such as N-[3-(dimethylaminopropyl)-N'-ethylcarbodiimide. Compounds of formula Ib' (where B is a carboxylic acid) can be prepared by saponification of compounds of formula Ib (where B is —$COOR^5$ and $R^5$ is an alkyl group) in aqueous THF in the presence of a base, such as lithium hydroxide, followed by acidification.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited to the illustrative examples set forth herein below, but rather defined by the claims appended thereto.

General

The following methods were used in the working Examples, except where noted otherwise.

Analytical HPLC and HPLC/MS Methods Employed in Characterization of Examples Reverse phase analytical HPLC was performed on Shimadzu LC10AS systems and reverse phase analytical HPLC/MS on Shimadzu LC10AS systems coupled with Waters ZMD Mass Spectrometers using the following methods:
Method A. Linear gradient of 10 to 100% solvent B over 2 min, with 1 min hold at 100% B;
UV visualization at 220 nm
Column: XTERRA® MS-C18, 2.1×50 mm
Flow rate: 1.0 ml/min
Solvent A: 0.1% trifluoroacetic acid, 10% water, 90 methanol.
Solvent B: 0.1% trifluoroacetic acid, 90% methanol, 10% water.
Method B. Linear gradient of 0 to 100% solvent B over 4 min, with 1 min hold at 100% B;
UV visualization at 220 nm
Column: PHENOMENEX® Luna C18 4.6×50 mm
Flow rate: 4 ml/min
Solvent A: 0.1% trifluoroacetic acid, 90% water, 10% methanol.
Solvent B: 0.1% trifluoroacetic acid, 90% methanol, 10% water.
Method C. Linear gradient of 0 to 100% solvent B over 4 min, with 1 min hold at 100% B;
UV visualization at 220 mm
Column: PHENOMENEX® Luna C18 4.6×50 mm
Flow rate: 4 ml/min
Solvent A: 0.1% trifluoroacetic acid, 90% water, 10% acetonitrile.
Solvent B: 0.1% trifluoroacetic acid, 90% acetonitrile, 10% water.
Method D. Linear gradient of 0 to 100% solvent B over 4 min, with 1 min hold at 100% B;
UV visualization at 220 nm
Column: PHENOMENEX® Luna C18 4.6×50 mm
Flow rate: 4 ml/min
Solvent A: 10 mM ammonium acetate, 90% water, 10% acetonitrile.
Solvent B: 10 mM ammonium acetate, 90% acetonitrile, 10% water.
Method E. Linear gradient of 0 to 100% solvent B over 4 min, with 1 min hold at 100% B;
UV visualization at 220 nm
Column: Xbridge C18 4.6×50 mm
Flow rate: 4 ml/min
Solvent A: 10 mM ammonium acetate, 90% water, 10% acetonitrile.
Solvent B: 10 mM ammonium acetate, 90% acetonitrile, 10% water.
Method F. Linear gradient of 0 to 100% solvent B over 4 min, with 1 min hold at 100% B;
UV visualization at 220 nm
Column: PHENOMENEX® Luna C18 4.6×50 mm
Flow rate: 4 ml/min
Solvent A: 10 mM ammonium acetate, 90% water, 10% methanol.
Solvent B: 10 mM ammonium acetate, 90% methanol, 10% water.

NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Preparative Example 1

3-(4-(tert-Butoxycarbonylamino)phenyl)-[1,2,4]triazolo[4,3-a]pyridine-8-carboxylic acid

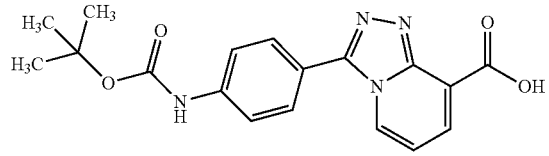

(1)

Preparation 1A: 3-Bromo-2-hydrazinylpyridine

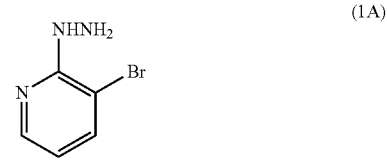

(1A)

To a stirring solution of 3-bromo-2-chloropyridine (8.56 g, 45 mmol) in pyridine (40 mL) was added anhydrous hydrazine (4.0 g, 125 mmol). The resulting mixture was stirred at 60° C. for 24 h. Analysis by HPLC indicated that about 50% of starting material was consumed. Additional hydrazine (4.0 g, 125 mmol) was added and the reaction mixture was stirred at 80° C. for another 16 h (total 40 h). After cooling to room temperature, the resulting white suspension was filtered. The collected solid was washed with water (2×50 mL), and dried in a 50° C. vacuum oven for 16 h to afford 5.13 g (61%) of the title compound as a white solid. HPLC/MS (Method C): retention time=0.38 min, [M+H]$^+$=188.0.

Preparation 1B: tert-Butyl 4-(2-(3-bromopyridin-2-yl)hydrazinecarbonyl)phenylcarbamate

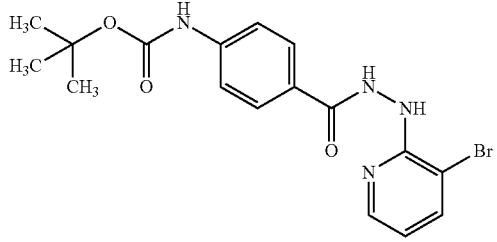

(1B)

A mixture of 4-(tert-butoxycarbonylamino)benzoic acid (5.05 g, 21.3 mmol), HOBt (2.9 g, 21.3 mmol) and EDC (4.07 g, 21.3 mmol) in CH$_2$Cl$_2$ (100 mL) was stirred at room temperature until becoming a clear solution, 1A (4.0 g, 21.3 mmol) was then added. The reaction mixture was stirred at room temperature for 2 h, and then concentrated under reduced pressure. The obtained residue was stirred with EtOAc (15 mL) and water (150 mL) for 1 h. The resulting suspension was filtered. The collected solid was rinsed with water (100 mL) and EtOAc (5 mL), dried in a 50° C. vacuum oven to afford 8.75 g (100%) of the title compound as a white solid. HPLC/MS (Method B): retention time=2.32 min, [M+H]$^+$=407.1.

Preparation 1C: 4-(8-Bromo-[1,2,4]triazolo[4,3-a]pyridin-3-yl)aniline

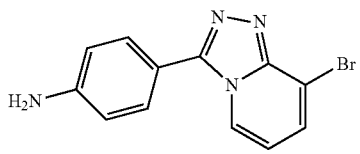

(1C)

A solution of 1B (8.7 g, 21.3 mmol) in a mixed solvent of AcOH (15 mL) and EtOH (30 mL) was heated in a microwave reactor at 160° C. for 1.5 h (The reaction was carried out in three individual microwave vials). The precipitate in the reaction vials was collected by filtration. The collected solid was rinsed with EtOH, dried in a 50° C. vacuum oven to yield 1.56 g of the title compound as a light brown solid. The mother liquor was heated in a microwave reactor at 185° C. for 0.5 h, and then concentrated under reduced pressure. The obtained residue was dissolved in EtOAc, washed carefully with saturated aqueous NaHCO$_3$, water, saturated aqueous NaCl, dried (Na$_2$SO$_4$) and concentrated under reduced pressure to give a crude product, which was purified by silica gel chromatography eluting with a gradient of EtOAc (50-100%) in hexanes to afford additional 1.18 g (total 2.74 g, 44%) of the title compound. HPLC/MS (Method A): retention time=1.23 min, [M+H]$^+$=289.1.

Preparation 1D: tert-Butyl 4-(8-bromo-[1,2,4]triazolo[4,3-a]pyridin-3-yl)phenylcarbamate

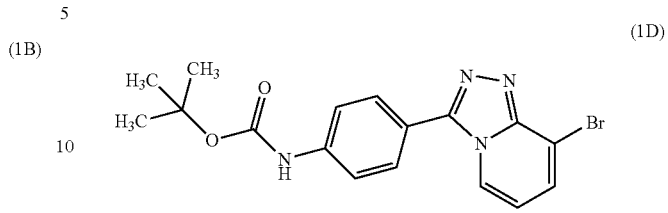

(1D)

To a stirred solution of 1C (0.7 g, 2.42 mmol) in THF (10 mL) at room temperature was added di-tert-butyl dicarbonate (0.555 g, 2.54 mmol). The resulting mixture was stirred at 80° C. for 16 h. Analysis by HPLC indicated that the starting amine was not consumed. Additional di-tert-butyl dicarbonate (0.278 g, 1.27 mmol) and THF (5 mL) were added. The reaction mixture was stirred at 80° C. for another 24 h. After cooling to room temperature, the reaction mixture was diluted with EtOAc (200 mL), washed with water, saturated aqueous NaCl, dried (Na$_2$SO$_4$) and concentrated under reduced pressure. The crude product was purified using a silica gel cartridge (40 g) eluting with a gradient of EtOAc (30-100%) in hexanes to afford 0.307 g (54%) of the title compound as an off-white solid. HPLC/MS (Method A): retention time=1.66 min, [M+H]$^+$=389.3.

Preparation 1E: Methyl 3-(4-(tert-butoxycarbonylamino)phenyl)-[1,2,4]triazolo[4,3-a]pyridine-8-carboxylate

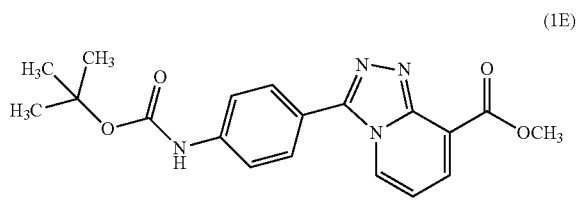

(1E)

Carbon monoxide gas was charged into a pressure bottle containing a mixture of 1D (300 mg, 0.77 mmol), Pd(OAc)$_2$ (69.2 mg, 0.31 mmol), dppp (127 mg, 0.31 mmol), Et$_3$N (0.43 mL, 3.1 mmol), DMSO (5 mL) and MeOH (2.5 mL) until the pressure reached 30 psi. The bottle was then sealed and heated at 80° C. for 16 h. After cooling to room temperature, the reaction was diluted with EtOAc, washed with water, saturated aqueous NaCl, dried (Na$_2$SO$_4$) and concentrated under reduced pressure. The crude product was purified using a silica gel cartridge (40 g) eluting with a gradient of EtOAc (50-100%) in hexanes to afford 205 mg (72%) of the title compound as an off-white solid. HPLC/MS (Method A): retention time=1.46 min, [M+H]$^+$=369.4.

Example 1

To a solution of 1E (150 mg, 0.44 mmol) in THF (2 mL) was added 2 M aqueous LiOH solution (2 mL). The resulting mixture was stirred at room temperature for 16 h. The reaction mixture was acidified to pH 3-4 by dropwise addition of 1 N aqueous HCl. The resulting precipitate was collected by filtration, washed with water, and dried in a 50° C. vacuum oven to afford 108 mg (75%) of the title compound as an off-white solid. HPLC/MS (Method B): retention time=1.38 min, [M+H]$^+$=355.3. $^1$H NMR (CD$_3$OD, 400 MHz): δ 8.68 (d, J=8.7 Hz, 1H), 8.26 (d, J=6.0 Hz, 1H), 7.80 (d, J=8.8 Hz, 2H), 7.72 (d, J=8.8 Hz, 2H), 7.23 (t, J=6.9 Hz, 1H), 1.55 (s, 9H).

Example 2

(S)-2-(3-(4-(tert-Butoxycarbonylamino)phenyl)-[1,2,4]triazolo[4,3-a]pyridine-8-carboxamido)-3-methylbutanoic acid

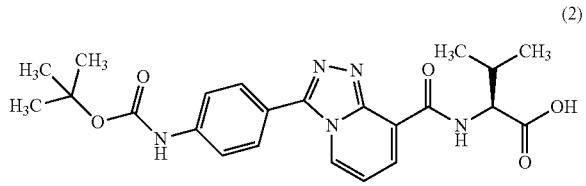
(2)

Preparation 2A: (S)-Ethyl 2-(3-(4-(tert-butoxycarbonylamino)phenyl)-[1,2,4]triazolo[4,3-a]pyridine-8-carboxamido)-3-methylbutanoate

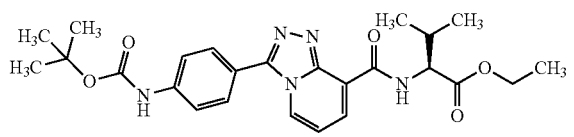
(2A)

To a solution of Example 1 (50 mg, 0.14 mmol) in DMF (1 mL) was added L-valine ethyl ester hydrochloride salt (33 mg, 0.18 mmol), HOBt (28.4 mg, 0.21 mmol), EDC (40 mg, 0.21 mmol) and (iPr)$_2$EtN (0.049 mL, 0.28 mmol). The resulting mixture was stirred at room temperature for 16 h, and then partitioned between water and EtOAc. The aqueous layer was extracted with EtOAc (2×20 mL), and the combined EtOAc extracts were washed with water, saturated aqueous NaCl, dried (Na$_2$SO$_4$) and concentrated under reduced pressure. The crude product was purified using a silica gel cartridge (12 g) eluting with a gradient of EtOAc (30-100%) in hexanes to afford 65 mg (97%) of the title compound as an off-white foam. HPLC/MS (Method A): retention time=1.93 min, [M+H]$^+$=482.5.

Example 2

To a solution of 2A (15 mg, 0.03 mmol) in THF (1 mL) was added 1 N aqueous NaOH solution (1 mL). The resulting mixture was stirred at room temperature for 16 h, and then acidified to pH 3-4 by dropwise addition of 1 N aqueous HCl. The mixture was extracted with EtOAc (3×10 mL), and the combined EtOAc extracts concentrated under reduced pressure. The crude product was purified using preparative HPLC (PHENOMENEX® Luna Axia, 5µ 30×100 mm using MeOH—H$_2$O-TFA solvent system) to afford 8.2 mg (60%) of the title compound as a yellow solid. HPLC/MS (method A): retention time=1.79 min, [M+H]$^+$=454.5. $^1$H NMR (CD$_3$OD, 400 MHz): δ 8.68 (d, J=8.7 Hz, 1H), 8.26 (d, J=6.0 Hz, 1H), 7.80 (d, J=8.8 Hz, 2H), 7.72 (d, J=8.8 Hz, 2H), 7.23 (t, J=6.9 Hz, 1H), 4.70 (d, J=4.4 Hz, 1H), 2.37-2.47 (m, 1H), 1.55 (s, 9H), 1.15 (d, J=7.2 Hz, 3H), 1.12 (d, J=7.2 Hz, 3H).

Example 3

(S)-3-Methyl-2-(3-(4-(3-(2-(trifluoromethyl)phenyl)ureido)phenyl)-[1,2,4]triazolo[4,3-a]pyridine-8-carboxamido)butanoic acid

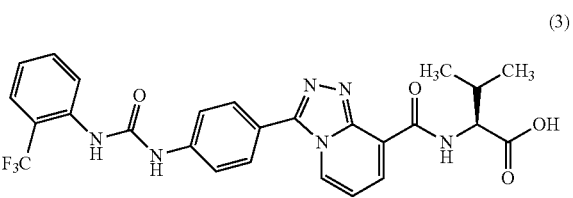
(3)

Preparation 3A: (S)-Ethyl 2-(3-(4-aminophenyl)-[1,2,4]triazolo[4,3-a]pyridine-8-carboxamido)-3-methylbutanoate

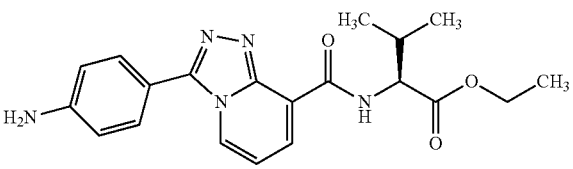
(3A)

To a solution of 2A (105 mg, 0.22 mmol) in CH$_2$Cl$_2$ (1.5 mL) was added trifluoroacetic acid (1.5 mL). After stirring at room temperature for 1 h, the reaction mixture was concentrated under reduced pressure. The crude product was taken into EtOAc, then washed with saturated aqueous NaHCO$_3$, saturated aqueous NaCl, dried (Na$_2$SO$_4$) and concentrated under reduced pressure to afford 81 mg (96%) of the title compound as a yellow foam. HPLC/MS (Method B): retention time=2.57 min, [M+H]$^+$=381.5.

Preparation 3B: (S)-Ethyl 3-methyl-2-(3-(4-(3-(2-(trifluoromethyl)phenyl)ureido)phenyl)-[1,2,4]triazolo[4,3-a]pyridine-8-carboxamido)butanoate

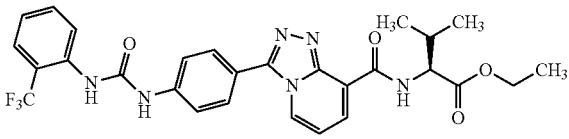
(3B)

A solution of 3A (81 mg, 0.20 mmol) and 2-trifluoromethylphenyl isocyanate (59 mg, 0.32 mmol) in THF (2 mL) was stirred at 60° C. for 1 h. Analysis by HPLC indicated that the starting amine was not consumed. Additional 2-trifluoromethyl phenyl isocyanate (20 mg, 0.107 mmol) was added and the reaction stirred at 60° C. for another 0.5 h. After cooling to room temperature, the reaction was concentrated under reduced pressure. The crude product was purified using a silica gel cartridge (12 g) eluting with a gradient of EtOAc (0-100%) in hexanes to afford 103 mg (87%) of the title compound as a white solid. HPLC/MS (Method A): retention time=1.94 min, [M+H]$^+$=569.6.

Example 3

To a solution of 3B (105 mg, 0.185 mmol) in THF (2 mL) was added 2 N aqueous LiOH solution (2 mL). The resulting mixture was stirred at room temperature for 3 h. Analysis by HPLC indicated that the starting ester was consumed. The reaction mixture was cooled at 0° C., and acidified to pH 3 by dropwise addition of 1 N aqueous HCl. The mixture was extracted with EtOAc (2×20 mL) and the combined EtOAc extracts were concentrated under reduced pressure. The crude product was purified using preparative HPLC (PHENOMENEX® Luna Axia, 5μ 30×100 mm, using MeOH—H$_2$O-TFA solvent system) to afford 71 mg (71%) of the title compound as a white solid. HPLC/MS (Method A): retention time=1.85 min, [M+H]$^+$=541.4. $^1$H NMR (CD$_3$OD, 400 MHz): 8.73 (d, J=7.2 Hz, 1H), 8.31 (d, J=6.6 Hz, 1H), 7.97 (d, J=7.2 Hz, 1H), 7.86 (d, 8.8 Hz, 2H), 7.79 (d, J=8.8 Hz, 2H), 7.56-7.72 (m, 2H), 7.22-7.37 (m, 2H), 4.70 (d, J=4.8 Hz, 1H), 2.37-2.48 (m, 1H), 1.15 (d, J=7.2 Hz, 3H), 1.12 (d, J=7.2 Hz, 3H).

Example 4

(S)-3-Methyl-2-(3-(4-(3-(2-(trifluoromethoxy)phenyl)ureido)phenyl)-[1,2,4]triazolo[4,3-a]pyridine-8-carboxamido)butanoic acid (4)

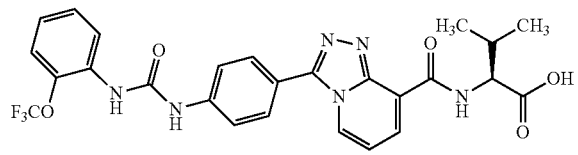

Preparation 4A: Ethyl-2-hydrazinylnicotinate (4A)

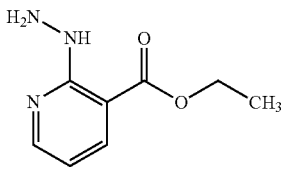

A solution of ethyl 2-chloronicotinate (10.0 g, 53.9 mmol) and anhydrous hydrazine (2.04 g, 63.8 mmol) in anhydrous 1,4-dioxane (200 mL) was stirred at 60° C. for 2 h. Analysis by LC/MS indicated the starting material was not consumed. Additional amount hydrazine (2.04 g, 63.8 mmol) was added and the reaction mixture was stirred at 60° C. overnight. After cooling to room temperature, the reaction mixture was concentrated in vacuo. The obtained residue was triturated with MeOH (35 mL), the insoluble white solid was removed by filtration and discarded. The methanol solution was concentrated in vacuo to yield a fluffy yellow solid which was triturated in diethylether to yield the title compound as an orange solid (5.4 g, 55%). HPLC/MS (Method D): retention time=1.46 min, [M+H]$^+$=182.3.

Preparation 4B: Ethyl 2-(2-(4-(tert-butoxycarbonylamino)benzoyl)hydrazinyl)nicotinate (4B)

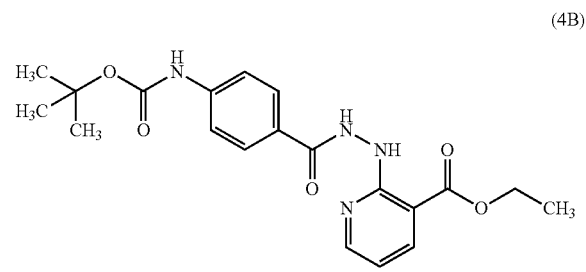

A suspension of 4-(tert-butoxycarbonylamino)benzoic acid (10.9 g, 45.8 mmol), HOBt (6.25 g, 46 mmol) and EDC (8.74 g, 46 mmol) in anhydrous DCM (200 mL) was stirred at room temperature for 10 min, and then a solution of 4A (9.5 g, 52.4 mmol) in anhydrous DCM (120 mL) was added. The reaction mixture was stirred at room temperature for 2.5 h, and then concentrated in vacuo. The obtained residue was suspended in EtOAc (300 mL) and water (200 mL) and stirred at room temperature for 0.5 h. The insoluble material was isolated by filtration, rinsed with water and a small amount of EtOAc, and then air dried to yield the title compound as a white solid (15.3 g, 73%). HPLC/MS (Method F): retention time=3.22 min, [M+H]$^+$=401.2.

Preparation 4C: Ethyl 3-(4-aminophenyl)-[1,2,4]triazolo[4,3-a]pyridine-8-carboxylate (4C)

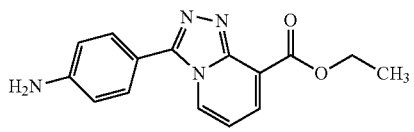

A suspension of 4B (13.4 g, 33.3 mmol) in POCl$_3$ (105 mL) was refluxed for 2.5 h. After cooling to room temperature, the reaction mixture was concentrated in vacuo to remove most of the POCl$_3$. The residue was then dissolved in ethanol (100 mL), and slowly poured into water (350 mL) with stirring. After stirring for 30 min, the resulting mixture was concentrated in vacuo. To the residue was added 6N aqueous HCl (92 mL), and the mixture was heated at 60° C. for 3 h. After cooling to room temperature, the reaction mixture was neutralized with a NaOH aqueous solution to pH=5. The precipitate was isolated by filtration, rinsed with water, and air-dried to yield the title compound as a golden-brown solid (7.27 g, 77%). HPLC/MS (Method F): retention time=2.01 min, [M+H]$^+$=283.1.

Preparation 4D: Ethyl 3-(4-(3-(2-(trifluoromethoxy)phenyl)ureido)phenyl)-[1,2,4]triazolo[4,3-a]pyridine-8-carboxylate (4D)

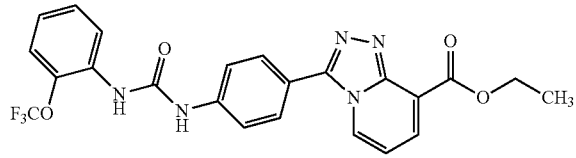

A solution of 4C (845 mg, 3 mmol) and o-trifluoromethoxyphenylisocyanate (650 mg, 3.2 mmol) in anhydrous THF (9 mL) was stirred at 70° C. for 2 h. LC/MS analysis indicated the starting amine was not consumed. Additional o-trifluoromethoxyphenyl-isocyanate (300 mg, 1.48 mmol) was added, and the mixture stirred at 70° C. for another 3.5 h. The mixture was allowed to cool to room temperature. The resulting precipitate was collected by filtration and rinsed with THF several times to yield the title compound as a yellow solid (1.12 g, 77%). HPLC/MS (Method D): retention time=2.35 min, [M+H]$^+$=486.2.

Preparation 4E: 3-(4-(3-(2-(Trifluoromethoxy)phenyl)ureido)phenyl)-[1,2,4]-triazolo[4,3-a]pyridine-8-carboxylic acid (4E)

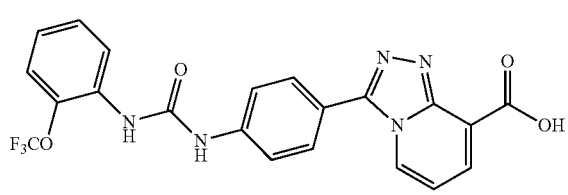

To a solution of 4D (1.1 g, 2.25 mmol) in THF (30 mL) was added 1N aqueous LiOH solution (4.5 mL, 4.5 mmol). The reaction mixture was stirred at room temperature for 2 h, and then neutralized with 1 N aqueous HCl. The mixture was concentrated in vacuo. The obtained residue was suspended in ethyl acetate (10 mL) and water (15 mL) and stirred for 5 min. The insoluble material was isolated by filtration and air-dried to yield the title compound (893 mg, 87%) as a brown solid. HPLC/MS (Method D): retention time=1.64 min, [M+H]$^+$=458.2.

Example 4

A suspension of 4E (46 mg, 0.1 mmol), EDC (19.2 μg, 0.1 mmol) and HOBt (13.6 mg, 0.1 mmol) in anhydrous DCM (1 mL) was stirred at room temperature for 5 min, and then L-Valine methyl ester (12.5 mg, 0.095 mmol) was added. The mixture was stirred at room temperature overnight, and then concentrated in vacuo. The residue was suspended in ethyl acetate (3 mL) and washed with saturated aqueous NaHCO$_3$ (1×0.8 mL), 1 N aqueous HCl (1×1 mL) and water (1×1 mL). The solvent was removed in vacuo to yield the product as an ester intermediate. The ester was dissolved in THF (1.5 mL) and 1 N aqueous LiOH solution (0.35 mL, 0.35 mmol) was added. The mixture was stirred at room temperature for 4 h, neutralized with 1 N aqueous HCl and concentrated in vacuo. The product was purified by preparative HPLC using CH$_3$CN/H$_2$O/TFA solvent system to yield the title compound. HPLC/MS (Method E): retention time=1.73 min, [M+H]$^+$=557.1.

Examples 5 to 21

Examples 5 to 21 were prepared by coupling 3-(4-(3-(2-(trifluoromethoxy)phenyl)ureido)phenyl)-[1,2,4]-triazolo[4,3-a]pyridine-8-carboxylic acid (4E) with various amino acid esters according to the general procedures described for Example 4 and listed in Table 1. Analytical data for the compounds in Table 1 are reported as follows: compound retention times were recorded using LC-MS conditions (Method E), and the molecular masses of the compounds were determined by MS (ES) by the formula m/z.

TABLE 1

| Example No. | Structure | Retention time (min) | [M + H]$^+$ |
| --- | --- | --- | --- |
| 5 | 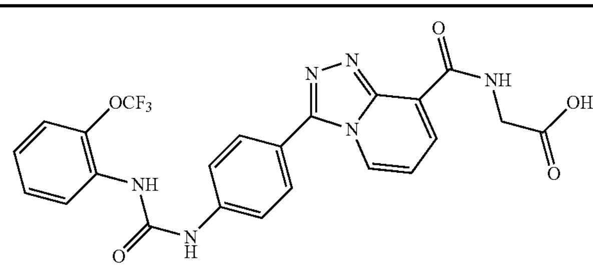 | 1.54 | 515.03 |
| 6 | 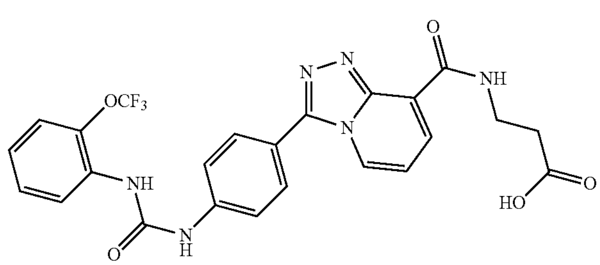 | 1.58 | 529.05 |

TABLE 1-continued

| Example No. | Structure | Retention time (min) | [M + H]⁺ |
|---|---|---|---|
| 7 | 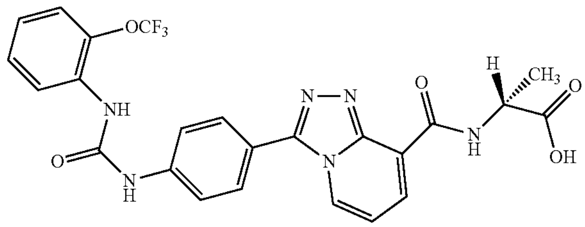 | 1.59 | 529.04 |
| 8 | 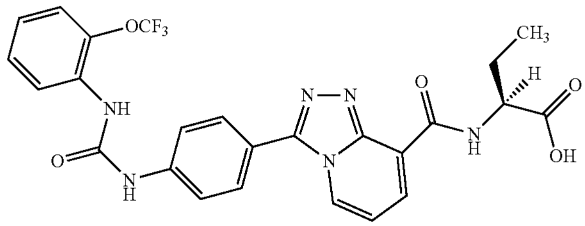 | 1.70 | 543.06 |
| 9 | 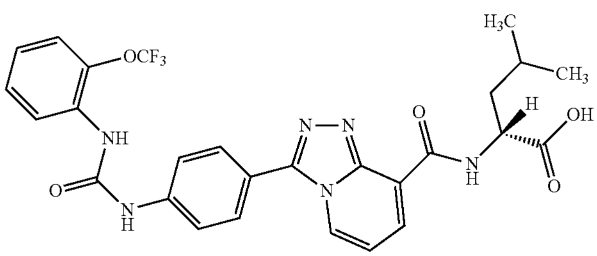 | 1.80 | 571.09 |
| 10 | 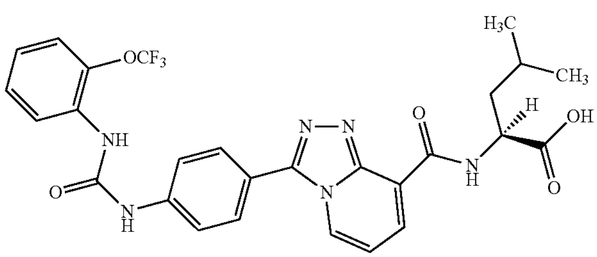 | 1.82 | 571.11 |
| 11 | 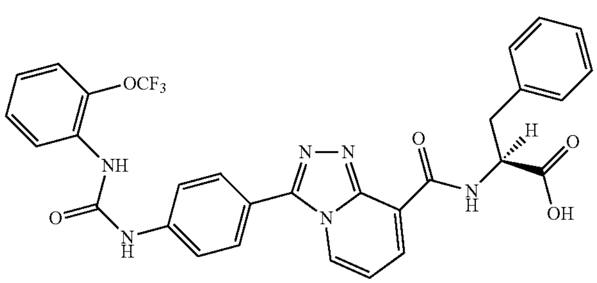 | 1.86 | 605.08 |
| 12 | 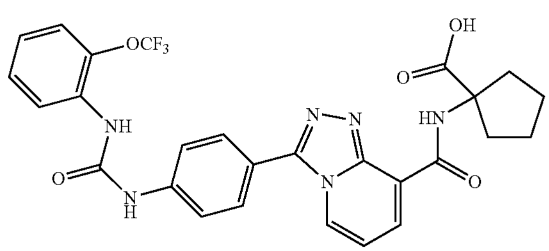 | 1.74 | 569.09 |

TABLE 1-continued

| Example No. | Structure | Retention time (min) | [M + H]+ |
|---|---|---|---|
| 13 | 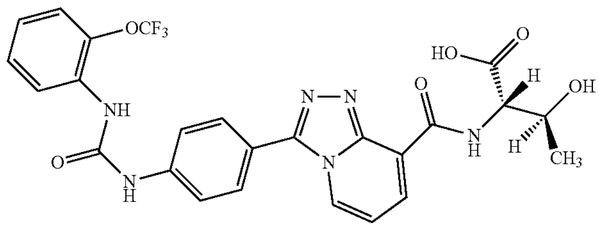 | 1.61 | 559.07 |
| 14 | 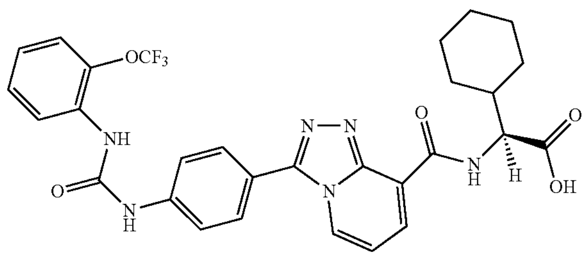 | 1.88 | 597.13 |
| 15 | 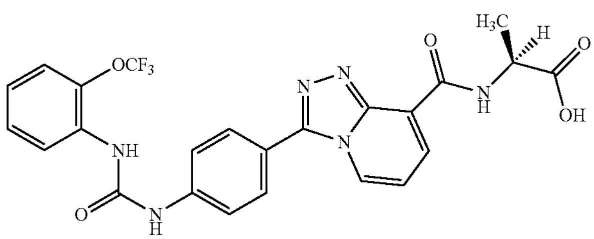 | 1.61 | 529.05 |
| 16 | 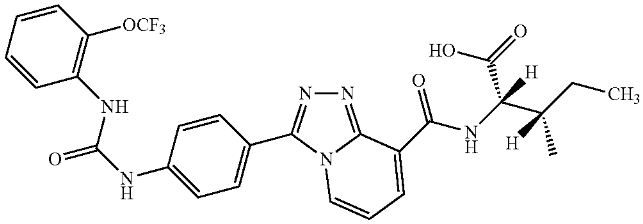 | 1.80 | 571.11 |
| 17 | 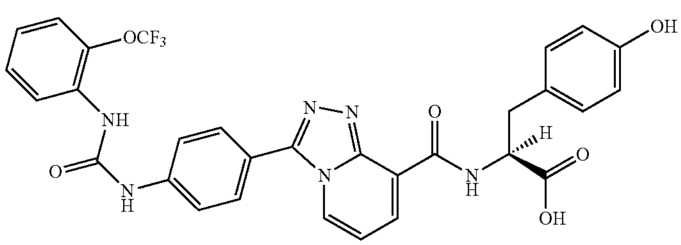 | 1.69 | 621.11 |
| 18 | 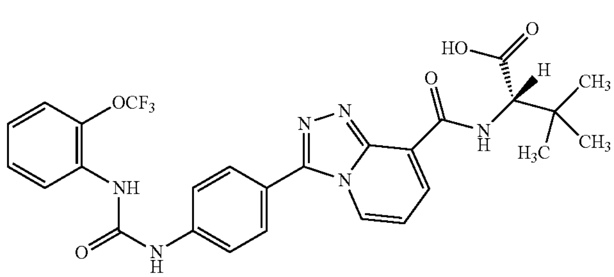 | 1.80 | 571.09 |

TABLE 1-continued

| Example No. | Structure | Retention time (min) | [M + H]+ |
|---|---|---|---|
| 19 | 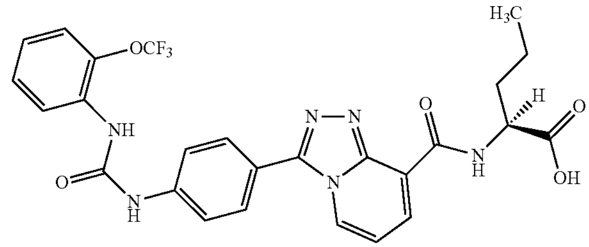 | 1.75 | 557.08 |
| 20 | 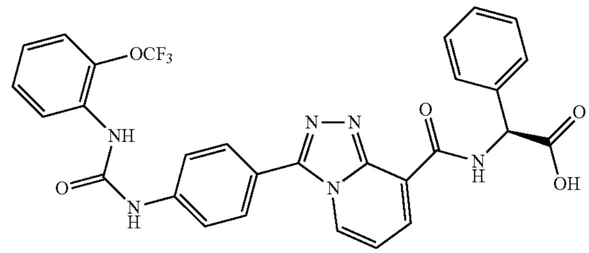 | 1.77 | 591.06 |
| 21 | 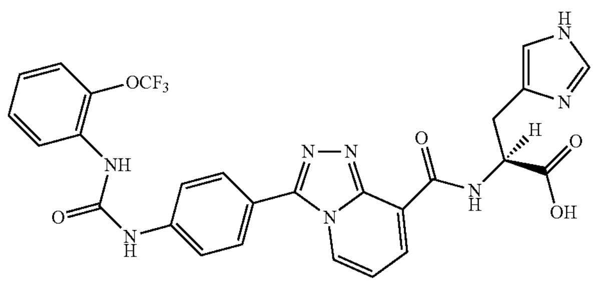 | 1.50 | 595.07 |

Example 22

(S)-1-(3-(4-(Methoxycarbonylamino)phenyl)-[1,2,4]triazolo[4,3-a]pyridine-8-carbonyl)pyrrolidine-2-carboxylic acid (22)

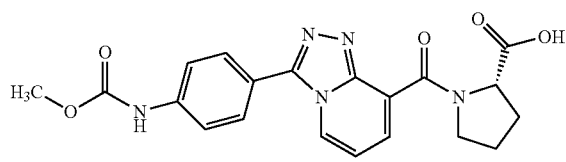

Preparation 22A: Ethyl 3-(4-methoxycarbonylamino)phenyl)-[1,2,4]triazolo[4,3-a]pyridine-8-carboxylate (22A)

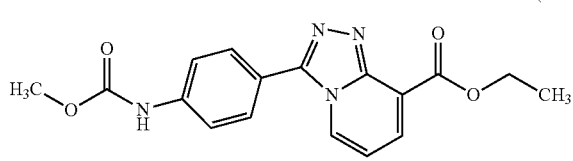

To a solution of 4C (0.845 g, 3 mmol) in a mixed solvent of pyridine (10 mL) and dichloromethane (10 mL) at 0° C. was added dropwise methylchloroformate (0.57 g, 6 mmol). The resulting mixture was stirred at 0° C. for 10 min, then at room temperature for 50 min. The reaction mixture was concentrated in vacuo. The solid residue was triturated in EtOAc (15 mL) and water (15 mL) to yield a yellow solid as the first crop of the product. The solution phase was separated into layers. The organic layer was washed with water (1×5 mL), dried over anhydrous Na₂SO₄, and concentrated in vacuo to yield the second crop of product. The combined product was further triturated in MeOH to afford the title compound as a yellow solid (0.55 g, 54%). HPLC/MS (Method D): retention time=1.54 min, [M+H]⁺=341.2

Preparation 22B: 3-(4-(Methoxycarbonylamino)phenyl)-[1,2,4]-triazolo[4,3-a]pyridine-8-carboxylic acid (22B)

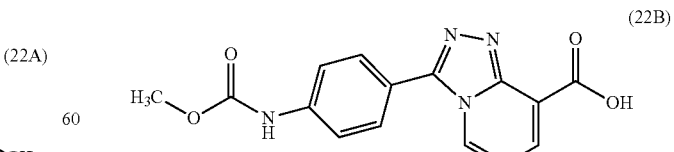

To a suspension of 22A (0.55 g, 1.61 mmol) in methanol (20 mL) was added 1 N aqueous NaOH solution (3 mL, 3 mmol). The mixture was stirred at room temperature for 2.5 h, and then concentrated in vacuo. The residue was suspended in water (20 mL) and acidified with 1 N aqueous HCl to pH 5. The resulting precipitate was isolated by filtration, rinsed with water several times, and air dried to yield the title compound as a brown solid (0.42 g, 84%). HPLC/MS (Method F): retention time=1.34 min, [M+H]$^+$=313.1.

Example 22

A suspension of 22B (31 mg, 0.1 mmol), EDC (19 mg, 0.1 mmol) and HOBt (13.6 mg, 0.1 mmol) in anhydrous dichloromethane (1 mL) was stirred at room temperature for 5 min, and then L-proline methyl ester (12.3 mg, 0.095 mmol) was added. The resulting mixture was stirred at room temperature overnight, and then concentrated in vacuo. The obtained residue was suspended in ethyl acetate (3 mL) and washed with saturated aqueous NaHCO$_3$ (1×0.8 mL), 1 N aqueous HCl (1×1 mL) and water (1×1 mL). The solvent was removed in vacuo to yield the product as an ester intermediate. The ester was dissolved in THF (1.5 mL) and then 1 N aqueous LiOH solution (0.35 mL, 0.35 mmol) was added. The mixture was stirred at room temperature for 4 h, acidified with 1 N aqueous HCl and dried in vacuo. The product was purified by preparative HPLC using CH$_3$CN/H$_2$O/TFA solvent system to yield the title compound (8.5 mg, 20%). HPLC/MS (Method. E): retention time=1.13 min, [M+H]$^+$=412.06. $^1$H NMR (500 MHz, DMSO-d$_6$): δ ppm 10.02 (s, 1H), 8.56-8.68 (m, 1H), 7.83 (d, J=8.80 Hz, 2H), 7.72 (d, J=8.80 Hz, 2H), 7.36-7.51 (m, 1H), 7.03-7.12 (m, 1H), 4.40-4.50 (m, 1H), 3.71 (s, 3H), 3.48-3.55 (m, 1H), 3.40-3.45 (m, 1H), 2.28-2.35 (m, 1H), 1.92-2.02 (m, 1H), 1.82-1.92 (m, 2H).

Example 23

(S)-3-Methyl-2-(3-(4-propionamidophenyl)-[1,2,4]triazolo[4,3-a]pyridine-8-carboxamido)butanoic acid

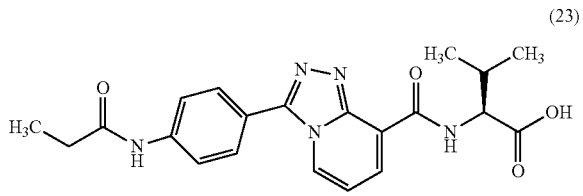

(23)

Preparation 23A: Ethyl 3-(4-propionamidophenyl)-[1,2,4]triazolo[4,3-a]pyridine-8-carboxylate

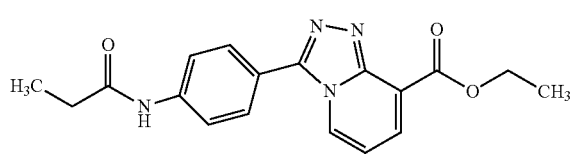

(23A)

To a suspension of 4C (0.85 g, 3.01 mmol) in anhydrous dichloromethane (25 mL) was added triethylamine (0.4 g, 4 mmol), followed by dropwise addition of propionylchloride (0.285 g, 3.1 mmol). The resulting mixture was stirred at room temperature for 40 min. Analytical HPLC showed the starting amine was not consumed. Additional propionylchloride (0.15 g, 1.63 mmol) was added and the reaction was stirred at room temperature for 30 min. The mixture was diluted with dichloromethane (10 mL), washed with water (1×), saturated aqueous NaHCO$_3$ (3×) and saturated aqueous NaCl (1×), dried over anhydrous Na$_2$SO$_4$, and concentrated in vacuo to yield a yellow solid. The product was triturated in MeOH to afford the title compound as a light brown solid (0.76 g, 75%). HPLC/MS (Method C): retention time=1.36, [M+H]$^+$=339.5.

Preparation 23B: 3-(4-Propionamidophenyl)-[1,2,4]triazolo[4,3-d]pyridine-8-carboxylic acid

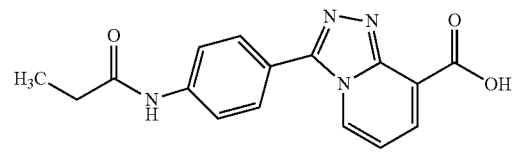

(23B)

To a suspension of 23A (0.76 g, 2.25 mmol) in methanol (38 mL) was added 1 N aqueous NaOH solution (5 mL, 5 mmol). The mixture was stirred at room temperature for 2 h, and then concentrated in vacuo. The crude product was dissolved in water (40 mL) and acidified with 1 N aqueous HCl solution. The resulting precipitate was isolated by filtration, rinsed with water, and air dried to afford the title compound as a brown solid (0.50 g, 72%). HPLC/MS (Method F): retention time=1.29 min, [M+H]$^+$=311.1.

Example 23

A suspension of 23B (25.4 mg, 0.081 mmol), EDC (15.6 mg, 0.081 mmol) and HOBt (11 mg, 0.081 mmol)) in anhydrous dichloromethane (1 mL) was stirred at room temperature for 5 min, and then L-valine methyl ester (11.8 mg, 0.09 mmol) was added. The resulting mixture was stirred at room temperature overnight and then concentrated in vacuo. The crude product was suspended in EtOAc (3 mL) and washed with saturated aqueous NaHCO$_3$ (1×0.8 mL), 1 N aqueous HCl (1×1 mL) and water (1×1 mL). The solvent was removed in vacuo to yield the product as an ester intermediate. The ester was dissolved in THF (1.5 mL) and then 1 N aqueous LiOH solution (0.35 mL, 0.35 mmol) was added. The mixture was stirred at room temperature for 4 h, acidified with 1 N aqueous HCl and dried in vacuo. The product was purified by preparative HPLC using CH$_3$CN/H$_2$O/TFA solvent system to afford the title compound (12 mg, 29%). HPLC/MS (Method E): retention time=1.10 min, [M+H]$^+$=410.09. $^1$H NMR (500 MHz, DMSO-d6): δ ppm 10.20 (s, 1H), 10.03 (d, J 8.25 Hz, 1H), 8.75 (d, J=7.15 Hz, 1H), 8.15 (d, J=7.15 Hz, 1H), 7.80-7.91 (m, 4H), 7.20 (t, J=6.87 Hz, 1H), 4.57 (dd, J=8.25, 4.40 Hz, 1H), 2.38 (q, J=7.33 Hz, 2H), 2.31 (dd, J=11.55, 7.15 Hz, 1H), 1.11 (t, J=7.42 Hz, 3H), 1.04 (d, J=6.60 Hz, 3H), 1.01 (d, J=6.60 Hz, 3H).

Example 24

(S)-3-(4-Hydroxyphenyl)-2-(3-(4-propionamidophenyl)-[1,2,4]triazolo[4,3-a]pyridine-8-carboxamido)propanoic acid

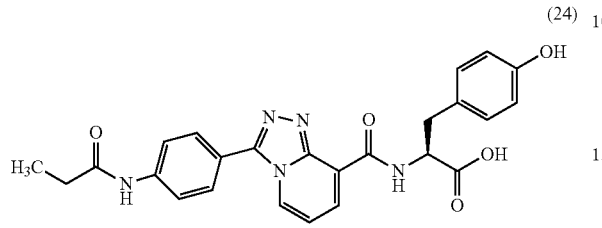
(24)

The title compound was prepared from 23B and L-tyrosine methyl ester as described for Example 23C. HPLC/MS (Method E): retention time=1.01 min, [M+H]$^+$=474.06.

Example 25

(S)-2-(3-(4-(6-Chlorobenzo[d]thiazol-2-ylamino)phenyl)-[1,2,4-]triazolo[4,3-a]pyridine-8-carboxamido)-3-methylbutanoic acid

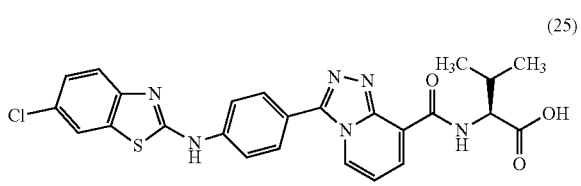
(25)

Preparation 25A: 4-(6-Chlorobenzo[d]thiazol-2-ylamino)benzoic acid

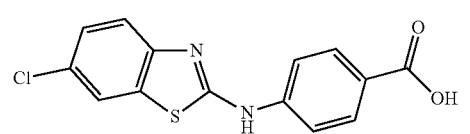
(25A)

To a suspension of tert-butyl 4-aminobenzoate (6.36 g, 32.9 mmol) and 2,6-dichlorobenzothiazole (5 g, 24.5 mmol) in isopropanol (150 mL) was added 4 N HCl solution in 1,4-dioxane (1.5 mL, 6 mmol). The mixture was refluxed at 100° C. for 7 h, and then allowed to cool to room temperature. The resulting precipitate was isolated by filtration to yield the first crop of the title compound as a white solid (3.13 g). The mother liquor was concentrated in vacuo and then stirred in a mixed solvent of TFA (20 mL) and dichloromethane (20 mL) overnight. The solvent was removed in vacuo, the obtained residue triturated with isopropanol/ethyl acetate. The isolated white solid was further stirred in a mixed solvent of isopropanol (12 mL) and ethyl acetate (8 mL) for 0.5 h, then isolated by filtration to yield a second crop of the title compound (3.5 g) (total 6.63 g, 85%). HPLC/MS (Method C): retention time=2.51 min, [M+H]$^+$=305.3.

Preparation 25B: Ethyl 2-(2-(4-(6-chlorobenzo[d]thiazol-2-ylamino)benzoyl)hydrazinyl)nicotinate

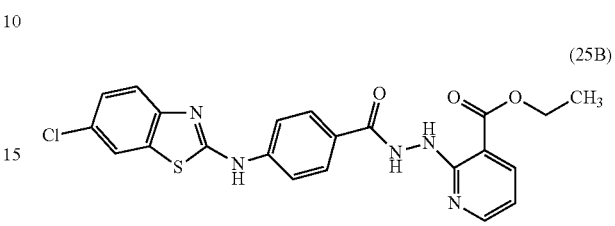
(25B)

A suspension of 4-(6-chlorobenzo[d]thiazol-2-ylamino)benzoic acid (117 mg, 0.38 mmol), EDC (88 mg, 0.46 mmol) and HOBt (63 mg, 0.46 mmol) in a mixed solvent of DMF (1 mL) and CH$_2$Cl$_2$ (1 mL) was stirred for 5 min, and then ethyl 2-hydrazinylnicotinate (4A) (70 mg, 0.38 mmol) was added, followed by triethylamine (78 mg, 0.77 mmol). The mixture was stirred at room temperature for 2 h. Analysis by LC/MS indicated the starting material was not consumed. Additional EDC (20 mg, 0.1 mmol) and HOBt (15 mg, 0.11 mmol) were added, and the mixture stirred for another 2 h before quenching with water (3 mL). The resulting precipitate was isolated by filtration and triturated with MeOH to yield the title compound as a fluffy white solid (94 mg). The methanol solution was concentrated in vacuo to collect additional product (50 mg) (total 144 mg, 87% yield). HPLC/MS (Method C): retention time=2.23 min, [M+H]$^+$=468.4.

Preparation 25C: Ethyl 3-(4-(6-chlorobenzo[d]thiazol-2-ylamino)phenyl)-[1,2,4]triazolo[4,3-a]pyridine-8-carboxylate

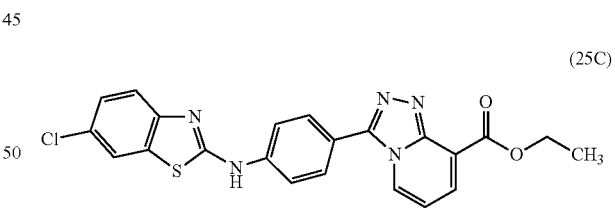
(25C)

To a solution of ethyl 2-(2-(4-(6-chlorobenzo[d]thiazol-2-ylamino)benzoyl)hydrazinyl)benzoate (142 mg, 0.3 mmol) in a mixed solvent of CCl$_4$ (0.6 mL), THF (0.8 mL) and CH$_2$Cl$_2$ (1.2 mL) cooled to 0° C. was added diisopropylethylamine (392 mg, 3 mmol) under argon atmosphere and then triethylphosphine (179 mg, 1.52 mmol). The mixture was stirred at 0° C. for 45 min, and then quenched with water (2.5 mL). The resulting precipitate was isolated by filtration and air dried to yield the title compound as a brown solid (108 mg). The filtrate was concentrated in vacuo to yield additional product (15 mg) (total 123 mg, 90% yield). HPLC/MS (Method C): retention time=2.21 min, [M+H]$^+$=450.3.

Preparation 25D: 3-(4-(6-Chlorobenzo[d]thiazol-2-ylamino)phenyl)-[1,2,4]triazolo[4,3-a]pyridine-8-carboxylic acid

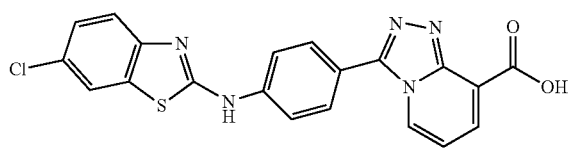

(25D)

To a suspension of ethyl 3-(4-(6-chlorobenzo[d]thiazol-2-ylamino)phenyl)-[1,2,4]triazolo[4,3-a]pyridine-8-carboxylate (935 mg, 2.08 mmol) in THF (20 mL) was added 1 N aqueous LiOH solution (4 mL, 4 mmol). The mixture was stirred at room temperature overnight, concentrated to one third of the initial volume, and then acidified with 1 N aqueous HCl. To the resulting precipitate was added water (15 mL) and $CH_2Cl_2$ (5 mL). After stirring for 15 min, the precipitate was isolated by filtration, rinsed with water and $CH_2Cl_2$, and then air dried to yield the title compound as a brown solid (790 mg, 90%). HPLC/MS (Method C): retention time=1.92 min, $[M+H]^+$=422.3.

Example 25

A suspension of 3-(4-(6-chlorobenzo[d]thiazol-2-ylamino)phenyl)-[1,2,4]triazolo[4,3-a]pyridine-8-carboxylic acid (33.7 mg, 0.08 mmol), EDC (15.5 mg, 0.081 mmol) and HOBt (11 mg, 0.081 mmol) in a mixed solvent of DMF (0.5 mL) and $CH_2Cl_2$ (0.5 mL) was stirred for 5 min. Then to this mixture was added in L-Valine methyl ester hydrochloride salt (13.4 mg, 0.08 mmol) in $CH_2Cl_2$ (0.5 mL) and diisopropylethylamine (20.7 mg, 0.16 mmol). The resulting mixture was stirred at room temperature overnight. The solvent was removed in vacuo. The mixture was suspended in 2:1 EtOAc/THF and washed with water (2×1 mL). The solvent was removed in vacuo. The obtained ester intermediate was suspended in THF (1 mL) and then 1 N aqueous LiOH solution (0.3 mL, 0.3 mmol) was added. The mixture was stirred at room temperature overnight, acidified with 1 N aqueous HCl. The solvent was removed in vacuo. The crude product was purified by preparative HPLC using $CH_3CN/H_2O/TFA$ solvent system to afford the title compound (18.3 mg, 36%). HPLC/MS (Method D): retention time=1.91 min, $[M+H]^+$=521.13. $^1$H NMR (DMSO-D6, 500 MHz): δ 10.96 (s, 1H), 10.04 (d, J=8.25 Hz, 1H), 8.80 (d, J=6.05 Hz, 1H), 8.17 (d, J=6.05 Hz, 1H), 8.06 (d, J=8.80 Hz, 2H), 8.00 (d, J=2.20 Hz, 1H), 7.94 (d, J=8.80 Hz, 2H), 7.65 (d, J=8.80 Hz, 1H), 7.38 (dd, J=8.80, 2.20 Hz, 1H), 7.21 (t, J=6.87 Hz, 1H), 4.58 (dd, J=8.25, 4.40 Hz, 1H), 2.24-2.39 (m, 1H). 1.03 (dd, J=16.50, 6.60 Hz, 6H).

Examples 26 to 43

Examples 26 to 43 were prepared by coupling 3-(4-(6-chlorobenzo[d]thiazol-2-ylamino)phenyl)-[1,2,4]triazolo[4,3-a]pyridine-8-carboxylic acid (25D) with various amino acid esters according to the general procedure described in Example 25E and listed in Table 2. Analytical data for the compounds in Table 2 was reported as follows: compound retention times were recorded using LC-MS conditions (Method D), and the molecular mass of the compounds were determined by MS (ES) by the formula m/z.

TABLE 2

| Example No. | Structure | Retention time (min) | [M + H]$^+$ |
|---|---|---|---|
| 26 | 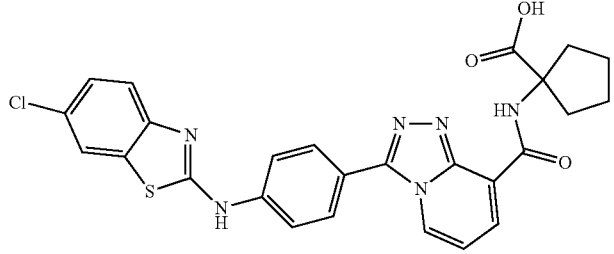 | 1.97 | 533.13 |
| 27 | 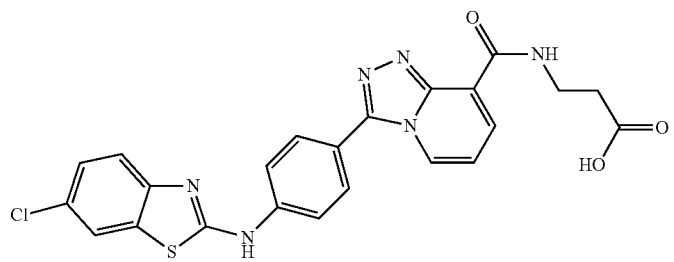 | 1.79 | 493.12 |

TABLE 2-continued
| Example No. | Structure | Retention time (min) | [M + H]+ |
|---|---|---|---|
| 28 | 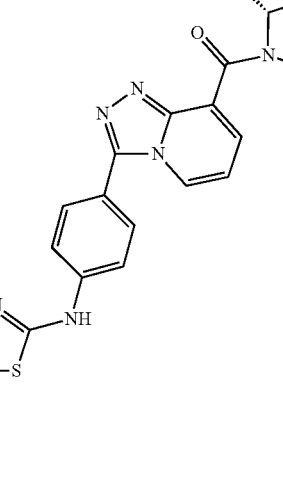 | 1.71 | 519.1 |
| 29 | 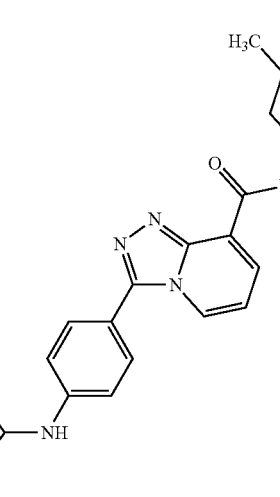 | 2.00 | 535.15 |
| 30 | 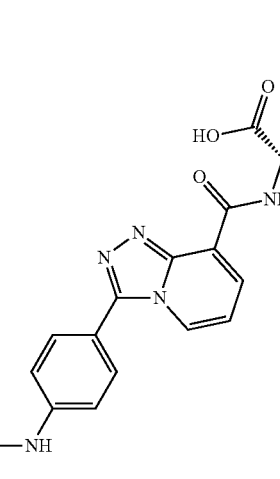 | 2.00 | 535.13 |

TABLE 2-continued

| Example No. | Structure | Retention time (min) | [M + H]+ |
|---|---|---|---|
| 31 | 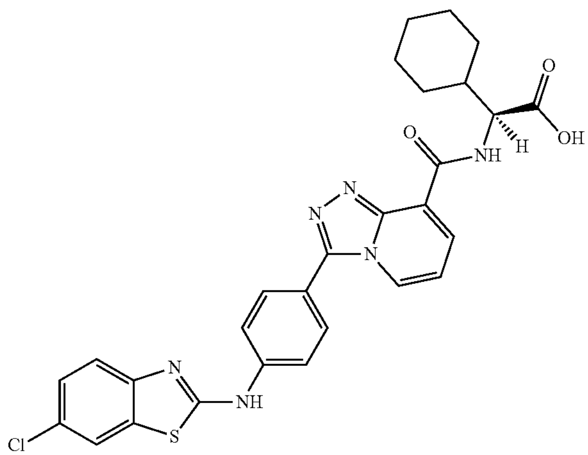 | 2.09 | 561.16 |
| 32 | 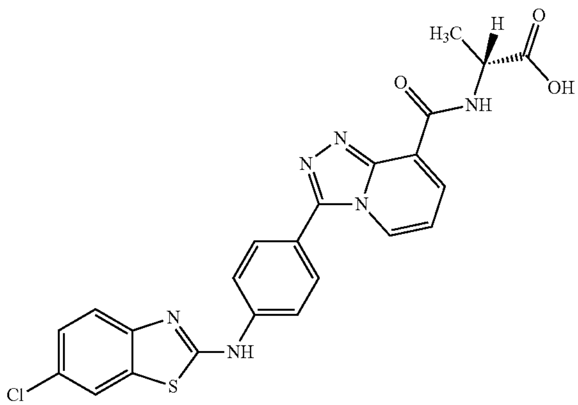 | 1.80 | 493.11 |
| 33 | 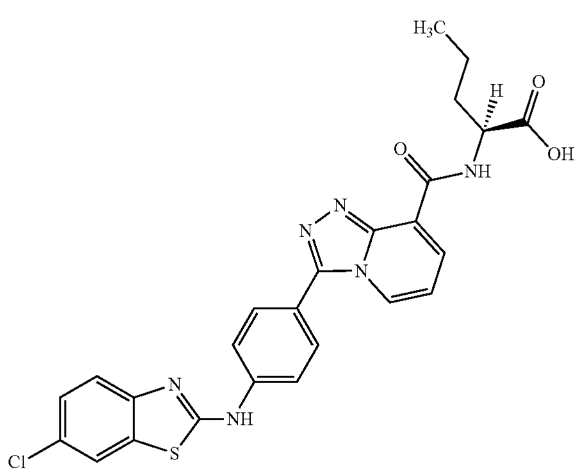 | 1.93 | 521.13 |

TABLE 2-continued

| Example No. | Structure | Retention time (min) | [M + H]+ |
|---|---|---|---|
| 34 | 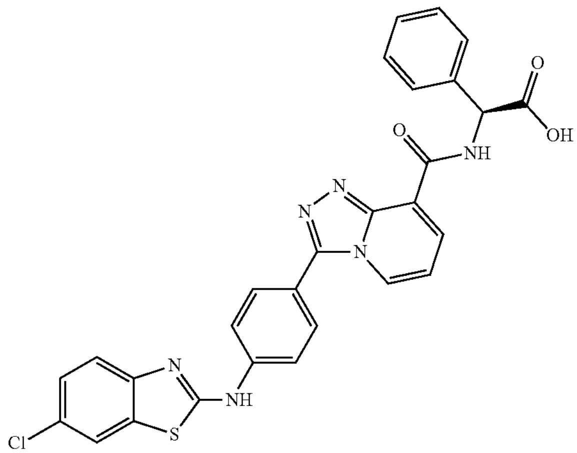 | 1.99 | 555.11 |
| 35 | 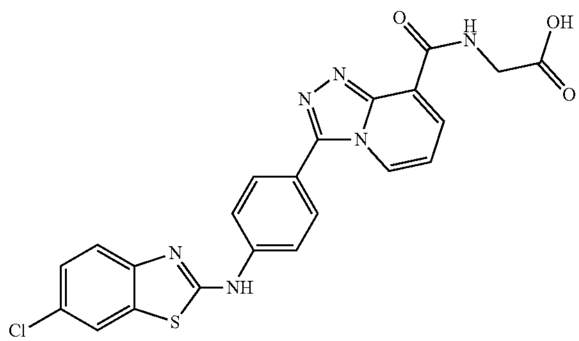 | 1.78 | 479.12 |
| 36 | 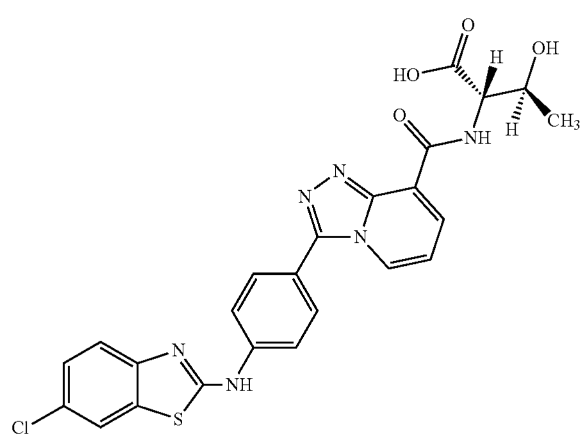 | 1.77 | 523.11 |

TABLE 2-continued

| Example No. | Structure | Retention time (min) | [M + H]+ |
|---|---|---|---|
| 37 | 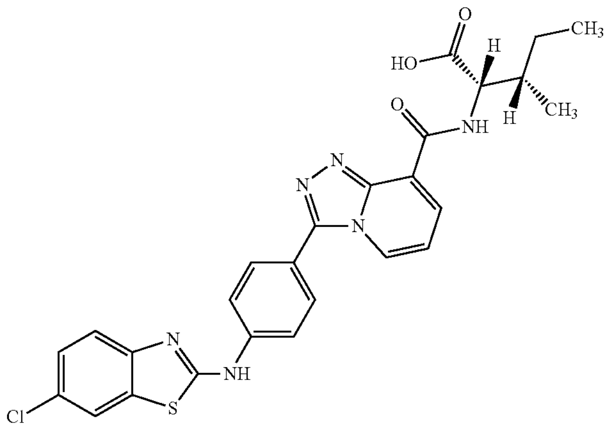 | 2.00 | 535.13 |
| 38 | 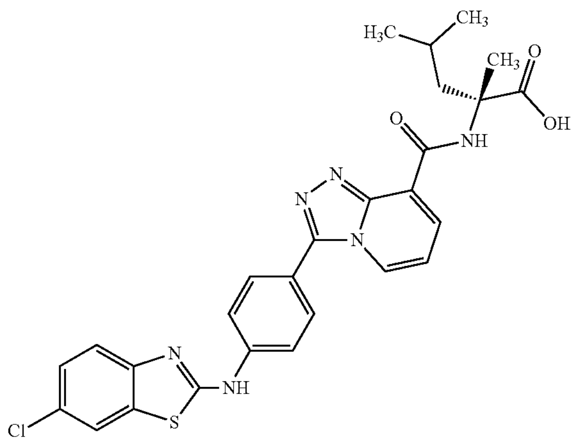 | 2.00 | 535.14 |
| 39 | 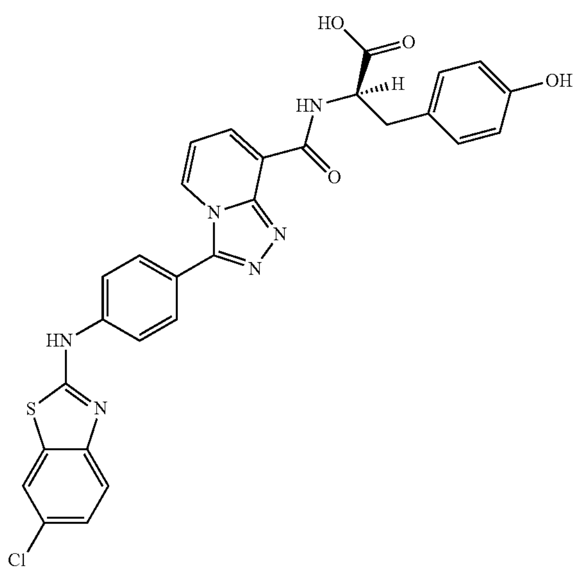 | 1.87 | 585.13 |

TABLE 2-continued
| Example No. | Structure | Retention time (min) | [M + H]+ |
|---|---|---|---|
| 40 | 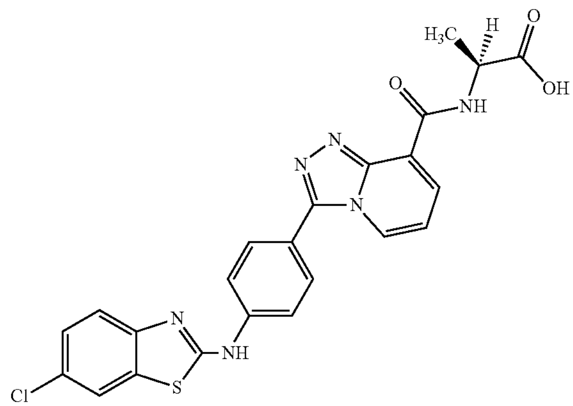 | 1.80 | 493.11 |
| 41 | 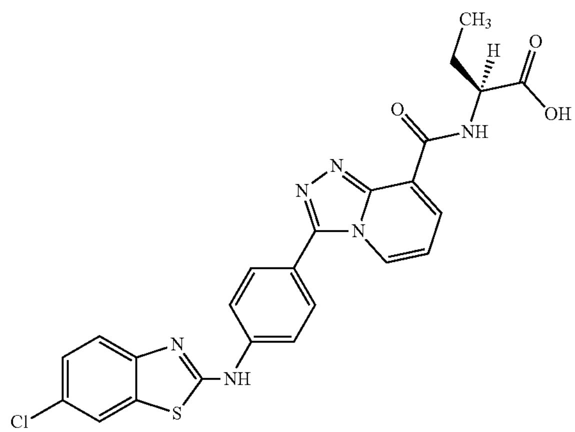 | 1.84 | 507.11 |
| 42 | 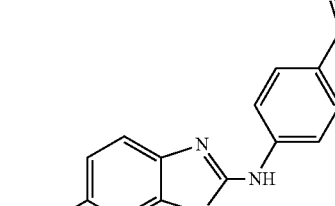 | 2.02 | 569.13 |

TABLE 2-continued

| Example No. | Structure | Retention time (min) | [M + H]+ |
|---|---|---|---|
| 43 | 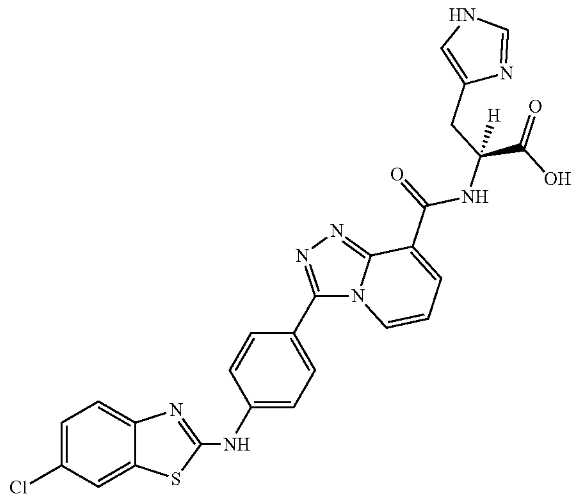 | 1.82 | 559.1 |

Example 44

(S)-3-Methyl-2-(3-(4-(thiazol-2-ylamino)phenyl)-[1,2,4]triazolo[4,3-a]pyridine-8-carboxamido)butanoic acid (44)

Preparation 44A: 4-(Thiazol-2-ylamino)benzoic acid

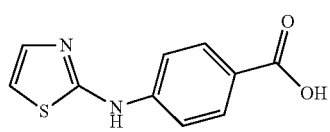

(44A)

To a suspension of tert-butyl 4-aminobenzoate (1.93 g, 10 mmol) and 2-bromothiazole (1.2 g, 7.3 mmol) in isopropanol (60 mL) was added 4 N HCl solution in 1,4-dioxane (0.5 mL, 2 mmol). The mixture was refluxed at 100° C. for 50 h, and then allowed to cool to room temperature. The mixture was concentrated to one third of the initial volume. The resulting precipitate was isolated by filtration to yield the first crop of the title compound as a brown solid (915 mg). The mother liquor was dried in vacuo. The obtained residue was dissolved in ethyl acetate (50 mL), washed with water (2×15 mL), dried over anhydrous $Na_2SO_4$, and concentrated in vacuo. The residue was triturated with isopropanol (8 mL) to yield the second crop of the title compound (341 mg) (total 1.25 g, 78% yield). HPLC/MS (Method D): retention time=0.57 min, [M+H]+=221.3.

Preparation 44B: Ethyl 2-(2-(4-(thiazol-2-ylamino)benzoyl)hydrazinyl)benzoate (44B)

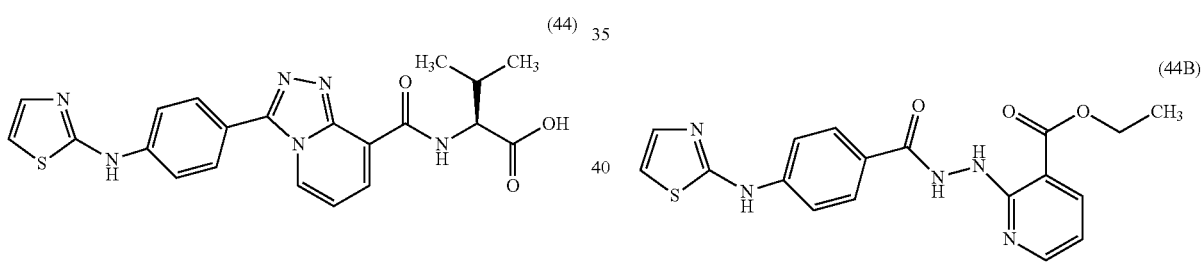

A suspension of 4-(thiazol-2-ylamino)benzoic acid (44A) (3.27 g, 14.7 mmol), EDC (2.85 g, 14.9 mmol) and HOBt (2.02 g, 14.9 mmol) in a mixed solvent of DMF (40 mL) and $CH_2Cl_2$ (80 mL) was stirred for 5 min, and then to this mixture was added in ethyl 2-hydrazinylnicotinate (4A) (2.7 g, 14.9 mmol) and triethylamine (2.25 g, 22.35 mmol). The mixture was stirred at room temperature for 3.5 h. Analysis by LC/MS indicated the starting material was not consumed. Additional amount of EDC (250 mg, 1.3 mmol) and ethyl 2-hydrazinylnicotinate (4A) (200 mg, 1.1 mmol) were added and the reaction mixture stirred overnight. The reaction mixture was concentrated in vacuo to one third of the initial volume, and then diluted with water (200 mL) and ethyl acetate (100 mL). The insoluble material was isolated by filtration to yield the title compound as a light brown solid (1.14 g). The filtrate was separated into organic and aqueous layers. The organic layer was washed with water, and then concentrated in vacuo. The obtained residue was triturated with methanol to yield the second crop of the title compound (1.35 g). (total 2.49 g, 44% yield). HPLC/MS (Method C): retention time=1.11 min, [M+H]+=384.2.

Preparation 44C: Ethyl 3-(4-(thiazol-2-ylamino)phenyl)-[1,2,4]triazolo[4,3-a]pyridine-8-carboxylate

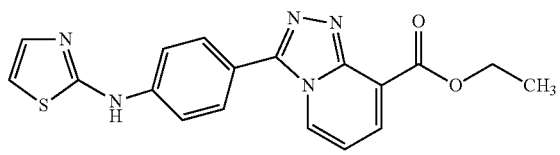

(44C)

A suspension of ethyl 2-(2-(4-(thiazol-2-ylamino)benzoyl)hydrazinyl)benzoate (44B) (1.22 g, 3.18 mmol) in POCl$_3$ (7.5 mL) was heated in a sealed tube at 110° C. for 3 h. After cooling to room temperature, the reaction mixture was concentrated in vacuo to remove most of the POCl$_3$. The residue was dissolved in MeOH (5 mL) and water (15 mL) and neutralized with 1N aqueous NaOH solution to pH ~5-6. The resulting precipitate was isolated by filtration, rinsed with water and methanol, and then air dried to yield the title compound as a brown solid (1.13 g, 97%). HPLC/MS (Method F): retention time=2.75 min, [M+H]$^+$=366.2.

Preparation 44D: 3-(4-(Thiazol-2-ylamino)phenyl)-[1,2,4]-triazolo[4,3-c]pyridine-8-carboxylic acid

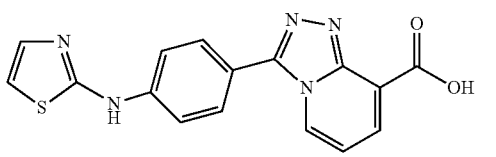

(44D)

To a solution of ethyl 3-(4-(thiazol-2-ylamino)phenyl)-[1,2,4]triazolo[4,3-a]pyridine-8-carboxylate (44C) (1.2 g, 3.3 mmol) in THF (25 mL) was added 1 N aqueous LiOH solution (6 mL, 6 mmol). The mixture was stirred at room temperature overnight, acidified with 1 N aqueous HCl and then concentrated in vacuo. The obtained residue was stirred in a mixed solvent of water (20 mL) and methanol (5 mL) for 5 min. The resulting precipitate was isolated by filtration, rinsed with water and methanol. The solid material was then triturated with a mixed solvent of isopropanol (20 mL), methanol (5 mL) and water (10 mL) to afford the title compound as a dark green solid (1.10 g, 100%). HPLC/MS (Method D): retention time=1.09 min, [M+H]$^+$=338.2.

Example 44

A suspension of 3-(4-(thiazol-2-ylamino)phenyl)-[1,2,4]triazolo[4,3-a]pyridine-8-carboxylic acid (44D) (27 mg, 0.08 mmol), EDC (15.5 mg, 0.081 mmol) and HOBt (11 mg, 0.081 mmol) in a mixed solvent of DMF (0.5 mL) and CH$_2$Cl$_2$ (0.5 mL) was stirred for 5 min. To this mixture was then added L-Valine methyl ester hydrochloride salt (13.4 mg, 0.08 mmol) in CH$_2$Cl$_2$ (0.5 mL) and diisopropylethylamine (20.7 mg, 0.16 mmol). The mixture was stirred at room temperature overnight, and then concentrated in vacuo. The residue was suspended in 2:1 EtOAc/THF and washed with water (2×1 mL). The solvent was removed in vacuo. The obtained ester intermediate was suspended in THF (1 mL) and then 1 N aqueous LiOH solution (0.3 mL, 0.3 mmol) was added. The mixture was stirred at room temperature overnight, and then acidified with 1 N aqueous HCl. The solvent was removed in vacuo. The crude product was purified by preparative HPLC using CH$_3$CN/H$_2$O/TFA solvent system to afford the title compound (18.5 mg, 42%). HPLC/MS (Method D): retention time=1.39 min, [M+H]$^+$=437.2. $^1$H NMR (500 MHz, DMSO-d$_6$) δ10.53 (s, 1H), 9.99 (d, J=8.25 Hz, 1H), 8.70 (d, J=7.15 Hz, 1H), 8.09 (d, J=7.15 Hz, 1H), 7.83-7.86 (m, 2H), 7.79-7.82 (m, 2H), 7.27 (d, J=3.30 Hz, 1H), 7.14 (t, J=6.87 Hz, 1H), 6.95 (d, J=3.85 Hz, 1H), 4.51 (dd, J=8.25, 4.40 Hz, 1H), 2.18-2.32 (m, 1H), 0.97 (dd, J=16.22, 6.87 Hz, 6H).

Examples 45 to 58

Examples 45 to 58 were prepared by coupling 3-(4-(thiazol-2-ylamino)phenyl)-[1,2,4]-triazolo[4,3-a]pyridine-8-carboxylic acid (44D) with various amino acid esters according to the procedures described in Example 44E and listed in Table 3. Analytical data for the compounds in Table 3 was reported as follows: compound retention times were recorded using LC-MS conditions (Method D), and the molecular mass of the compounds were determined by MS (ES) by the formula m/z.

TABLE 3

| Example No. | Structure | Retention time (min) | [M + H]$^+$ |
|---|---|---|---|
| 45 | ![structure] | 1.52 | 485.18 |
| 46 | ![structure] | 1.20 | 439.18 |

TABLE 3-continued
| Example No. | Structure | Retention time (min) | [M + H]+ |
|---|---|---|---|
| 47 | 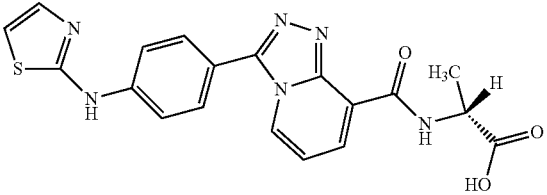 | 1.26 | 409.17 |
| 48 | 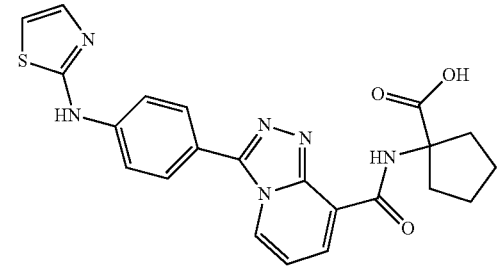 | 1.40 | 449.19 |
| 49 | 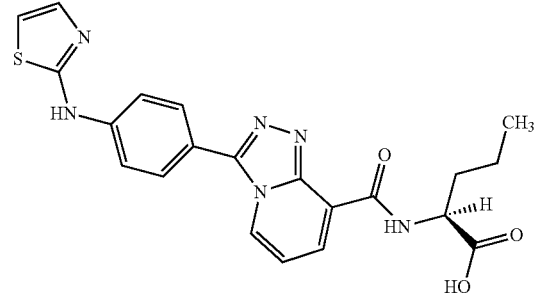 | 1.41 | 437.19 |
| 50 | 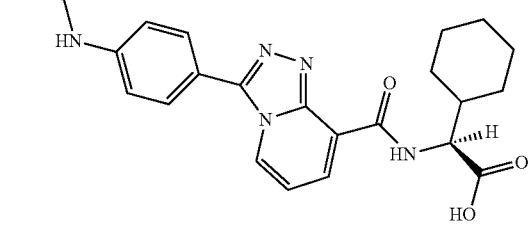 | 1.57 | 477.22 |
| 51 | 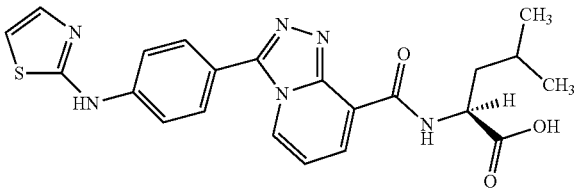 | 1.48 | 451.21 |
| 52 | 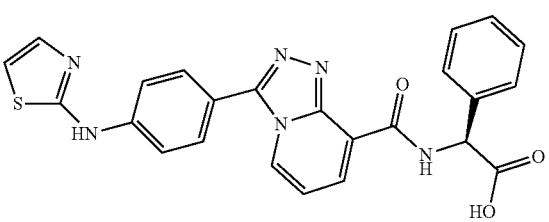 | 1.47 | 471.18 |

TABLE 3-continued

| Example No. | Structure | Retention time (min) | [M + H]+ |
|---|---|---|---|
| 53 | 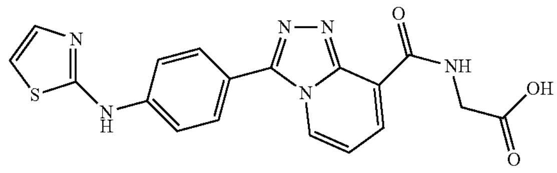 | 1.23 | 395.16 |
| 54 | 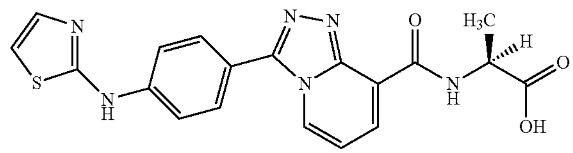 | 1.26 | 409.18 |
| 55 | 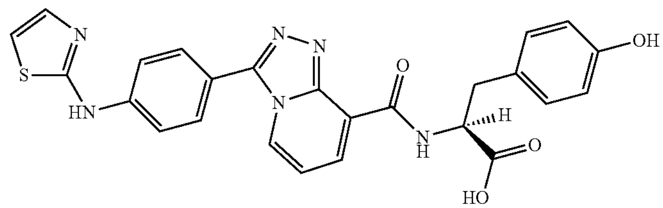 | 1.34 | 501.16 |
| 56 | 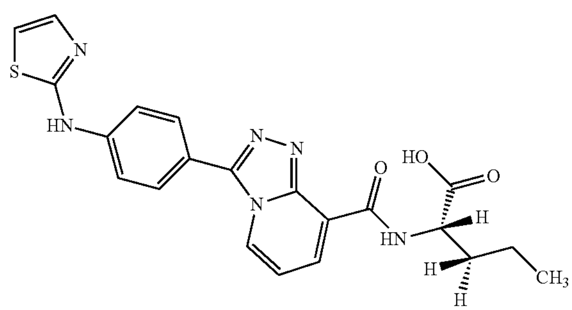 | 1.47 | 451.19 |
| 57 | 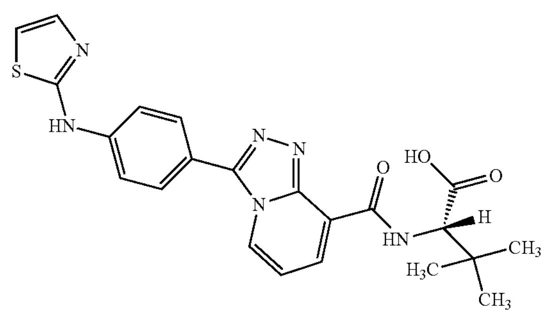 | 1.46 | 451.19 |
| 58 | 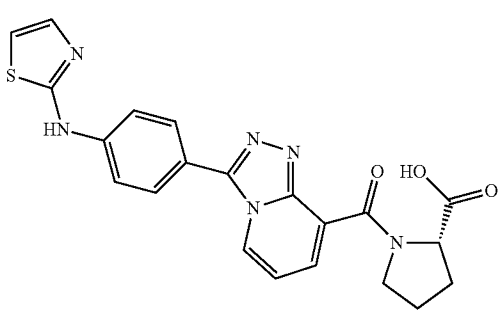 | 1.18 | 435.2 |

Example 59

(S)-3-Methyl-2-(3-(4-(2-phenylacetamido)phenyl)-[1,2,4]triazolo[4,3-a]pyridine-8-carboxamido)butanoic acid

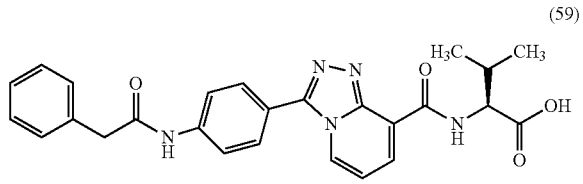
(59)

Preparation 59A: 3-(4-(2-Phenylacetamido)phenyl)-[1,2,4]triazolo[4,3-a]pyridine-8-carboxylic acid

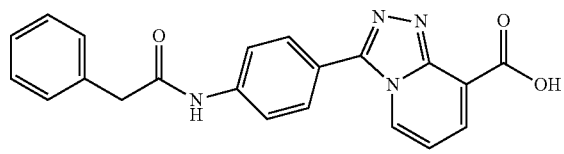
(59A)

To a solution of ethyl 3-(4-aminophenyl)-[1,2,4]-triazolo[4,3-a]pyridine-8-carboxylate (4C) (30 mg, 0.106 mmol) and 2-phenylacetyl chloride (16.34 mg, 0.106 mmol) in dichloromethane (1 mL) was added triethylamine (11.8 mg, 0.117 mmol). The reaction mixture was stirred at room temperature for 30 min, and then concentrated in vacuo. The obtained residue was stirred in mixed solvents of EtOAc (4 mL) and H₂O (2 mL) at room temperature. The resulting suspension was filtered to yield the first crop of the product as a brown solid. The filtrate was separated and the isolated organic layer concentrated in vacuo to yield the second crop of the product (total 40 mg, 94% yield as an ester intermediate).

To a solution of the ester intermediate in THF (2 mL) was added 2 N aqueous LiOH (0.2 mL, 0.4 mmol). The resulting mixture was stirred at room temperature for 3 h, and then acidified with 1 N aqueous HCl and concentrated in vacuo. The obtained residue was then triturated with H₂O and a small amount of CH₂Cl₂ to yield the title compound as a light brown solid (31 mg, 78%). HPLC/MS (Method C): retention time=1.38, [M+H]⁺=373.4. ¹H NMR (500 MHz, DMSO-d6): δ 10.59 (s, 1H), 8.85 (d, J=7.15 Hz, 1H), 8.24 (d, J=6.60 Hz, 1H), 7.87-7.95 (m, 2H), 7.81-7.86 (m, 2H), 7.31-7.39 (m, 4lT), 7.22-7.30 (m, 2H), 3.71 (s, 2H).

Example 59

A suspension of 3-(4-(2-phenylacetamido)phenyl)-[1,2,4]triazolo[4,3-a]pyridine-8-carboxylic acid (59A) (14 mg, 0.038 mmol), EDC (9 mg, 0.047 mmol) and HOBt (6.4 mg, 0.047 mmol) in a mixed solvent of DMF (0.5 mL) and DCM (0.5 mL) was stirred for 5 min, and then L-valine tert-butyl ester hydrochloride (8 mg, 0.038 mmol) and triethylamine (7.6 mg, 0.075 mmol) were added. The mixture was stirred at room temperature overnight, and then concentrated in vacuo. The crude product was purified by preparative HPLC using CH₃CN/H₂O/TFA solvent system to yield an ester intermediate, which was stirred in a mixed solvent of TEA (1 mL) and DCM (1 mL) at room temperature for 2.5 h. The solvent was removed by vacuo to yield the title compound as a brown solid (10.2 mg, 57%). HPLC/MS (Method C): retention time=1.99, [M+H]⁺=472.5. ¹H NMR (500 MHz, DMSO-d₆): δ 10.51 (s, 1H), 10.02 (d, J=8.25 Hz, 1H), 8.74 (d, J=7.15 Hz, 1H), 8.15 (d, J=6.05 Hz, 1H), 7.81-7.94 (m, 4H), 7.30-7.42 (m, 4H), 7.26 (t, J=6.60 Hz, 1H), 7.20 (t, J=7.15 Hz, 1H), 4.57 (dd, J=8.25, 4.40 Hz, 1H), 3.71 (s, 2H), 2.24-2.39 (m, 1H), 1.02 (dd, J=16.22, 6.87 Hz, 6H).

Example 60

(S)—N-(1-Hydroxybutan-2-yl)-3-(4-(2-phenylacetamido)phenyl)-[1,2,4]-triazolo[4,3-a]pyridine-8-carboxamide

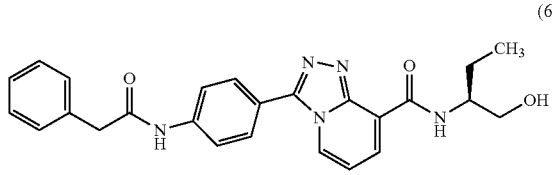
(60)

A suspension of 3-(4-(2-phenylacetamido)phenyl)-[1,2,4]triazolo[4,3-a]pyridine-8-carboxylic acid (59A) (14 mg, 0.038 mmol), EDC (9 mg, 0.047 mmol) and HOBt (6.4 mg, 0.047 mmol) in a mixed solvent of DMF (0.5 mL) and DCM (0.5 mL) was stirred for 5 min, and then (S)-2-aminobutan-1-ol hydrochloride salt (5.6 mg, 0.045 mmol) and triethylamine (7.6 mg, 0.075 mmol) were added. The mixture was stirred at room temperature overnight. The solvent was removed in vacuo. The crude product was purified by preparative HPLC using CH₃CN/H₂O/TFA solvent system to yield the title compound (8.3 mg, 50%). HPLC/MS (Method C): retention time 1.75, [M+H]⁺=444.5. ¹H NMR (500 MHz, DMSO-d₆): δ 10.50 (s, 1H), 9.58 (d, J=8.25 Hz, 1H), 8.71 (d, J=7.15 Hz, 1H), 8.14 (d, J=6.05 Hz, 1H), 7.80-7.92 (m, 4H), 7.30-7.43 (m, 4H), 7.26 (t, J=6.60 Hz, 1H), 7.19 (t, J=6.87 Hz, 1H), 3.93-4.07 (m, 1H), 3.71 (s, 2H), 3.54-3.63 (m, 1H), 3.50 (dd, J=11.0 Hz, 4.95 Hz, 1H), 1.68-1.78 (m, 1H), 1.54-1.65 (m, 1H), 0.87-1.06 (m, 3H).

Example 61

(S)-3-Methyl-2-(3-(4-(3-(2-(trifluoromethoxy)phenyl)ureido)phenyl)-[1,2,4]triazolo[4,3-a]pyrazine-8-carboxamido)butanoic acid

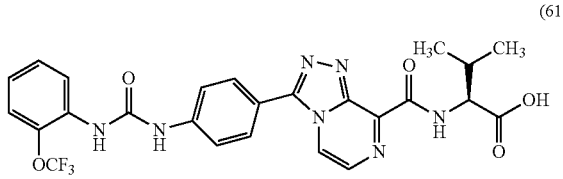
(61)

Preparation 61A: 2-Chloro-3-hydrazinylpyrazine

(61A)

A mixture of 2,3-dichloropyrazine (6.26 g, 42.0 mmol) and anhydrous hydrazine (5 mL, 159 mmol) in pyridine (22 mL, 272 mmol) was stirred at 60° C. for 2.5 h. After cooling to room temperature, the reaction mixture was concentrated in vacuo. The obtained residue was triturated with water. The resulting slurry was filtered, and the collected solid air dried to yield the first crop of the title compound (3.88 g) as a white solid. The filtrate was concentrated in vacuo, the obtained residue was treated by repeating above process to afford additional amount of the product (1.73 g). (total 5.61 g, 92% yield). HPLC/MS (Method C): retention time=0.30 min, [M+H]+=144.8. $^1$H NMR (500 MHz, DMSO-d$_6$): δ 8.27 (s, 1H), 8.05 (s, 1H), 7.56 (s, 1H), 4.32 (s, 2H); $^{13}$C NMR (500 MHz, DMSO-d$_6$) δ 152.62, 140.67, 132.60, 130.01.

Preparation 61B: tert-Butyl 4-(2-(3-chloropyrazin-2-yl)hydrazinecarbonyl)phenyl carbamate

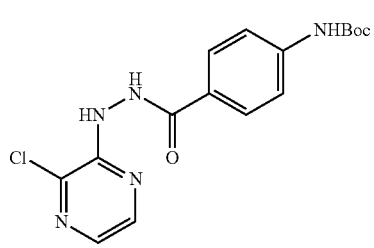

(61B)

A suspension of 4-(tert-butoxycarbonylamino)benzoic acid (1.642 g, 6.92 mmol), EDC (1.33 g, 6.92 mmol) and HOBt (935 mg, 6.92 mmol) in a mixed solvent of DMF (10 mL) and dichloromethane (10 mL) was stirred until it became a clear solution, and then 2-chloro-3-hydrazinylpyrazine (61A) (1.0 g, 6.92) was added followed by triethylamine (1.4 g, 13.82 mmol). The resulting mixture was stirred at room temperature overnight. The solvent was removed in vacuo. The obtained residue was stirred with water (25 mL) and ethyl acetate (40 mL). The resulting suspension was filtered, and the collected solid dried in a vacuum oven to yield the title compound as a brown solid (2.395 g, 95%). HPLC/MS (Method C): retention time=1.89 min, [M+H]+=364.0. $^1$H NMR (500 MHz, DMSO-d$_6$): δ 10.35 (s, 1H), 9.68 (s, 1H), 9.08 (s, 1H), 8.08 (d, J=2.20 Hz, 1H), 7.83 (d, J=8.80 Hz, 2H), 7.77 (d, J=2.75 Hz, 1H), 7.55 (d, J=8.80 Hz, 2H), 1.48 (s, 9H).

Preparation 61C: tert-Butyl 4-(8-chloro-[1,2,4]triazolo[4,3-a]pyrazin-3-yl)phenylcarbamate

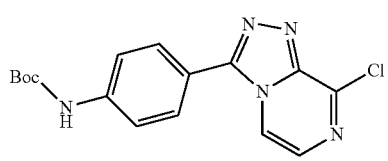

(61C)

To a solution of tert-butyl 4-(2-(3-chloropyrazin-2 yl)hydrazinecarbonyl)phenyl carbamate (61B) (1.96 g, 5.39 mmol) in a mixed solvent of CCl$_4$ (11 mL), THF (16 mL) and CH$_2$Cl$_2$ (22 mL) cooled to 0° C. under argon was added DIPEA (6.96 g, 53.9 mmol), followed by dropwise addition of triethylphosphine (3.18 g, 26.9 mmol). The reaction mixture was stirred at 0° C. for 1 h and then quenched with addition of water (55 mL). The product was extracted with ethyl acetate (3×). The combined organics were washed with brine, dried over anhydrous Na$_2$SO$_4$, and then concentrated in vacuo to yield a brown solid. This crude product was triturated with CH$_2$CH$_2$/EtOH (4 mL/8 mL). The resulting suspension was filtered to yield the first crop of the title compound as a white solid (790 mg). The filtrate was concentrated and the obtained residue purified using a silica gel cartridge, eluting with EtOAc/CH$_2$Cl$_2$ to yield additional amount of the product as an off-white solid (550 mg) (total amount: 1.34 g, 72% yield). HPLC/MS (Method C): retention time=2.06 min, [M+H]+=346.1. $^1$H NMR (500 MHz, DMSO-d$_6$): δ 9.75 (s, 1H), 8.62 (d, J=4.95 Hz, 1H), 7.84 (d, J=8.80 Hz, 2H), 7.68-7.77 (m, 3H), 1.47 (s, 9H). $^{13}$NMR (500 MHz, DMSO-d$_6$): 152.86, 148.80, 143.76, 142.16, 142.12, 129.06, 128.72, 118.87, 118.46, 117.84, 79.84, 28.28.

Preparation 61D: Methyl 3-(4-(tert-butoxycarbonylamino)phenyl)-[1,2,4]triazolo[4,3-a]pyrazine-8-carboxylate

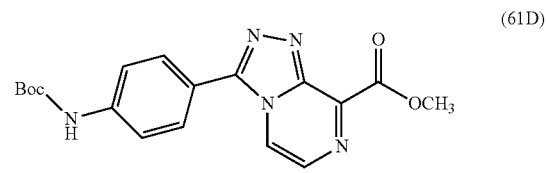

(61D)

Carbon monoxide gas was charged into a pressure bottle containing a mixture of tert-butyl 4-(8-chloro-[1,2,4]triazolo[4,3-a]pyrazin-3-yl)phenylcarbamate (61C) (714 mg, 2.065 mmol), Pd(OAc)$_2$ (185 mg, 0.826 mmol), dppp (341 mg, 0.826 mmol), Et$_3$N (1.15 mL, 8.26 mmol), DMSO (12 mL) and MeOH (6 mL) until the pressure reached to 30 psi. The bottle was then sealed and heated at 75° C. for 4 h. After cooling to room temperature, the reaction was diluted with EtOAc, washed with water (3×), saturated aqueous NaCl, dried (Na$_2$SO$_4$) and concentrated under reduced pressure. The crude product was purified using a silica gel cartridge eluting with a gradient of EtOAc in hexanes to afford 103 mg (17%) of the title compound. HPLC/MS (Method C): retention time=1.72 min, [M+H]+=370.4; $^1$H NMR (500 MHz, DMSO-d$_6$): δ 9.75 (s, 1H), 8.78 (d, J=4.95 Hz, 1H), 8.04 (d, J=4.95 Hz, 1H), 7.86 (d, J=8.80 Hz, 2H), 7.73 (d, J=8.80 Hz, 2H), 4.02 (s, 3H), 1.47 (s, 9H).

Preparation 61E: Methyl 3-(4-aminophenyl)-[1,2,4]triazolo[4,3-a]pyrazine-8-carboxylate

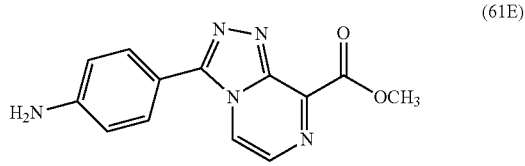

(61E)

To a solution of methyl 3-(4-(tert-butoxycarbonylamino) phenyl)-[1,2,4]triazolo[4,3-a]pyrazine-8-carboxylate (61D) (130 mg, 0.35 mmol) in CH$_2$Cl$_2$ (1 mL) was added TFA (1 L). The resulting mixture was stirred at room temperature for 2 h, and then concentrated in vacuo. The obtained residue was stripped with CH$_2$Cl$_2$ and dried in high vacuum to yield the title compound as brown oil (94 mg). HPLC/MS (Method D): retention time=0.39 min, [M+H]+=270.5.

Preparation 61F: Methyl 3-(4-(3-(2-(trifluoromethoxy)phenyl)ureido)phenyl)-[1,2,4]triazolo[4,3-c]pyrazine-8-carboxylate

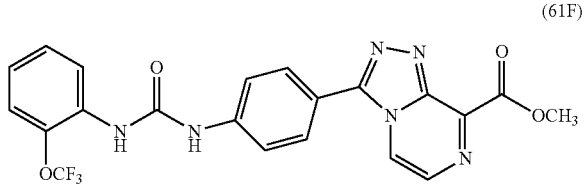

(61F)

To a solution of methyl 3-(4-aminophenyl)-[1,2,4]triazolo[4,3-a]pyrazine-8-carboxylate (61E) (94 mg, 0.35 mmol) in anhydrous THF (1.5 mL) was added 2-trifluoromethylphenyl isocyanate (71 mg, 0.35 mmol). The mixture was stirred at 70° C. overnight. After cooling to room temperature, the mixture was concentrated. The crude product was purified by preparative HPLC using $CH_3CN/H_2O/TFA$ solvent system to yield the title compound (32 mg, 19%). HPLC/MS (Method D): retention time=2.09 min, $[M+H]^+$=473.3; $^1H$ NMR (500 MHz, DMSO-$d_6$): δ 9.64 (s, 1H), 8.81 (d, J=4.95 Hz, 1H), 8.59 (s, 1H), 8.27 (d, J=7.15 Hz, 1H), 8.06 (d, J=4.95 Hz, 1H), 7.91 (d, J=8.80 Hz, 2H), 7.75 (d, J=8.80 Hz, 2H), 7.33-7.43 (m, 2H), 7.09-7.16 (m, 1H), 4.03 (s, 3H).

Preparation 61G: 3-(4-(3-(2-(Trifluoromethoxy)phenyl)ureido)phenyl)-[1,2,4]triazolo[4,3-a]pyrazine-8-carboxylic acid

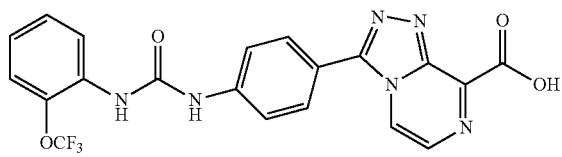

(61G)

To a solution of methyl 3-(4-(3-(2-(trifluoromethoxy)phenyl)ureido) phenyl)-[1,2,4]triazolo[4,3-a]pyrazine-8-carboxylate (61F) (72 mg, 0.152 mmol) in THF (3 mL), was added potassium trimethylsilanolate (78 mg, 0.61 mmol). The mixture was stirred at room temperature for 70 min, and then acidified with 1 N aqueous HCl (0.62 mL). The mixture was diluted with EtOAc, washed with water (3×), brine, and dried over $Na_2SO_4$. The solvent was removed in vacuo to yield the title compound as a brown solid (70 mg, 100%). HPLC/MS (Method C): retention time=1.83 min, $[M+H]^+$=459.4.

Example 61

A suspension of 3-(4-(3-(2-(trifluoromethoxy)phenyl)ureido)phenyl)-[1,2,4]triazolo[4,3-a]pyrazine-8-carboxylic acid (61G) (35 mg, 0.076 mmol), EDC (15.4 mg, 0.08 mmol) and HOBt (11 mg, 0.08 mmol) in a mixed solvent of DMF (0.5 mL) and $CH_2Cl_2$ (1 mL) was stirred until it became a clear solution, and then L-valine tert-butyl ester hydrochloride salt (16.8 mg, 0.08 mmol) and triethylamine (16 mg, 0.16 mmol) were added. The mixture was stirred at room temperature for 2 h, and then concentrated in vacuo. The crude product was purified by preparative HPLC using $CH_3CN/H_2O/$ TFA solvent system to yield a brown solid (31 mg, 66%) as a methyl ester intermediate. HPLC/MS (Method C): retention time=3.02 min, $[M+H]^+$=614.6.

A solution of the ester intermediate (31 mg, 0.05 mmol) in a mixed solvent of TEA (1 mL) and $CH_2Cl_2$ (1 mL) was stirred at room temperature for 4 h, and then concentrated in vacuo to yield the title compound as a brown solid. HPLC/MS (Method C): retention time=2.27 min, $[M+H]^+$=558.5. $^1H$ NMR (500 MHz, DMF-$d_7$): δ 9.78 (s, 1H), 9.75 (d, J=8.25 Hz, 1H), 8.91 (d, J=4.95 Hz, 1H), 8.72 (s, 1H), 8.43 (d, J=6.60 Hz, 1H), 8.18 (d, J=4.95 Hz, 1H), 8.00 (m, 2H), 7.87 (d, J=8.80 Hz, 2H), 7.43 (m, 2H), 7.09-7.24 (m, 1H), 4.74 (dd, J=8.52, 4.67 Hz, 1H), 2.42 (d, J=4.95 Hz, 1H), 1.11 (dd, J=7.15, 4.95 Hz, 6H).

Example 62

(S)-1-(3-(4-(3-(2-(Trifluoromethoxy)phenyl)ureido) phenyl)-[1,2,4]triazolo[4,3-a]pyrazine-8-carbonyl) pyrrolidine-2-carboxylic acid

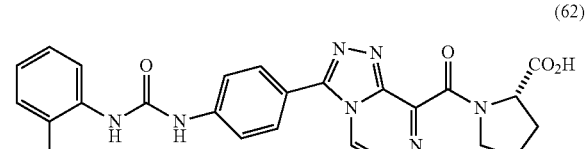

(62)

The title compound was prepared from 3-(4-(3-(2-(trifluoromethoxy)phenyl)ureido)phenyl)-[1,2,4]triazolo[4,3-a]pyrazine-8-carboxylic acid (61G) and L-proline tert-butyl ester by analogous procedure described in Example 61H. HPLC/MS (Method C): retention time=1.91-2.01 min (broad rotomer), $[M+H]^+$=556.4.

Example 63

(S)-2-(3-(4-(6-Chlorobenzo thiazol-2-ylamino)phenyl)-[1,2,4]triazolo[4,3-a]pyrazine-8-carboxamido)-3-methylbutanoic acid

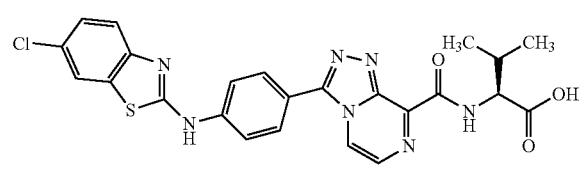

(63)

Preparation 63A: 4-(6-Chlorobenzo[d]thiazol-2-ylamino)benzoic acid

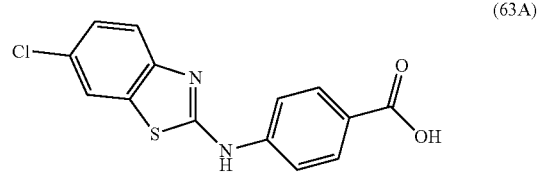

(63A)

To a suspension of tert-butyl 4-aminobenzoate (6.36 g, 32.9 mmol) and 2,6-dichlorobenzothiazole (5 g, 24.5 mmol) in isopropanol (150 mL) was added 4 N HCl in 1,4-dioxane (4 mL, 16 mmol). The mixture was refluxed at 100° C. for 7 h, and then allowed to cool to room temperature. White precipitates formed during cooling were isolated by filtration to yield the first crop of the title compound as a white solid (3.13 g). The filtrate was concentrated in vacuo and then stirred in a mixed solvent of TEA (20 mL) and CH$_2$Cl$_2$ (20 mL) overnight. The solvent was removed in vacuo, and the residue was triturated with isopropanol/ethyl acetate. The isolated white solid was stirred in a mixed solvent of isopropanol (12 mL) and ethyl acetate (8 mL) for 0.5 h and collected by filtration to yield the second crop of the title compound (3.5 g) (total 6.63 g, 85% yield). HPLC/MS (Method C): retention time=2.51 min, [M+H]$^+$=305.3. $^1$H NMR (500 MHz, DMSO-d$_6$) δ 11.08 (bs, 1H), 7.98 (d, J=2.20 Hz, 1H), 7.94 (m, 2H), 7.88 (m, 2H), 7.64 (d, J=8.25 Hz, 1H), 7.36 (dd, J=8.80, 2.20 Hz, 1H).

Preparation 63B: 4-(6-Chlorobenzo[d]thiazol-2-ylamino)-N'-(3-chloropyrazin-2-yl)benzohydrazide

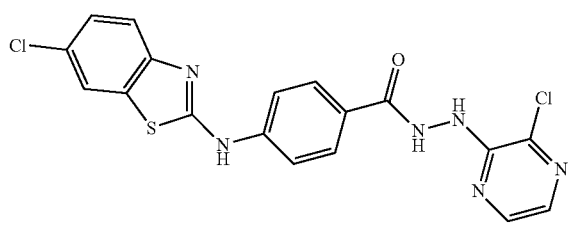

(63B)

A suspension of 4-(6-chlorobenzo[d]thiazol-2-ylamino) benzoic acid (63A) (6.62 g, 21.72 mmol), EDC (4.37 g, 22.81 mmol) and HOBt (3.08 mg, 22.81 mmol) in a mixed solvent of DMF (25 mL) and CH$_2$Cl$_2$ (50 mL) was stirred for 5 min, and then 2-chloro-3-hydrazinylpyrazine (61A) (3.14 g, 21.72 mmol) and triethylamine (4.4 g, 43.4 mmol) were added. The mixture was stirred at room temperature over the weekend. Additional EDC (1.5 g, 7.85 mmol) and HOBt (1.15 g, 8.45 mmol) were added in and the reaction mixture stirred for another 2 h before concentrated in vacuo. The obtained residue was partitioned between EtOAc (250 mL) and water (200 mL), and the separated EtOAc layer washed with water (2×200 mL), and concentrated in vacuo. The crude product was triturated with water (50 mL) and EtOAc (20 mL) and isolated by filtration, rinsed with water and then air dried to yield the title compound as a dark brown solid (6.17 g). The second crop of the product was isolated from the concentrated mother liquor using the same trituration process (0.76 g) (total 6.93 g, 74% yield). HPLC/MS (Method C): retention time=2.43 min, [M+H]$^+$=431.1. $^1$H NMR (500 MHz, DMSO-d$_6$) δ 10.90 (s, 1H), 10.41 (s, 1H), 9.12 (s, 1H), 8.09 (d, J=2.20 Hz, 1H), 7.99 (d, J=2.20 Hz, 1H), 7.91-7.97 (m, 2H), 7.85-7.90 (m, 2H), 7.78 (d, J=2.75 Hz, 1H), 7.65 (d, J=8.80 Hz, 1H), 7.37 (dd, J=8.80, 2.20 Hz, 1H).

Preparation 63C: 6-Chloro-N-(4-(8-chloro-[1,2,4]triazolo[4,3-a]pyrazin-3-yl)phenyl)benzo[d]thiazol-2-amine

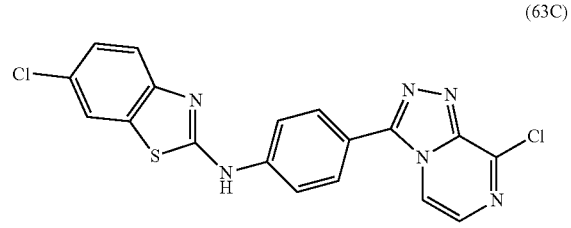

(63C)

To a solution of 4-(6-chlorobenzo[d]thiazol-2-ylamino)-N'-(3-chloropyrazin-2-yl)benzohydrazide (63B) (6.17 g, 14.31 mmol) in a mixed solvent of CCl$_4$ (60 mL), THF (80 mL) and CH$_2$Cl$_2$ (120 mL) cooled to 0° C. under argon was added DIPEA (18.49 g, 143 mmol), followed by dropwise addition of triethylphosphine (8.45 g, 71.5 mmol). After addition, the reaction mixture was stirred at 0° C. for 1 h, and then quenched by addition of water (100 mL). The precipitate was isolated by filtration and air dried to yield the first crop of the title compound as a dark brown solid (3.92 g). The filtrate was extracted with ethyl acetate (2×). The combined organics were washed with water (1×100 mL), dried over anhydrous Na$_2$SO$_4$ and concentrated in vacuo. The obtained residue was triturated with CH$_3$OH/CH$_2$Cl$_2$ (35 mL/5 mL) to yield the second crop of the title compound (0.95 g) (total 4.87 g, 82% yield). HPLC/MS (Method C): retention time=2.61 min, [M+H]$^+$=413.3. $^1$H NMR (500 MHz, DMSO-d$_6$): δ 10.98 (s, 1H), 8.68 (d, J=4.95 Hz, 1H), 8.05 (d, J=8.25 Hz, 2H), 7.98 (s, 1H), 7.96 (d, J=825 Hz, 2H), 7.77 (d, J=4.95 Hz, 1H), 7.63 (d, J=8.25 Hz, 1H), 7.37 (d, J=8.80 Hz, 1H).

Preparation 63D: Methyl 3-(4-(6-chlorobenzo[d]thiazol-2-ylamino)phenyl)-[1,2,4]triazolo[4,3-a]pyrazine-8-carboxylate

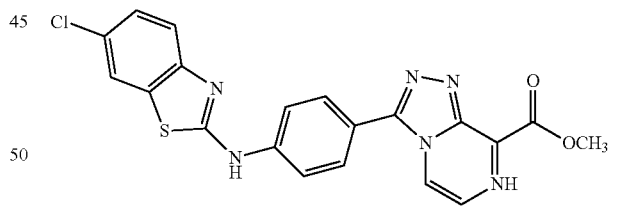

(63D)

Carbon monoxide gas was charged into a pressure bottle containing a mixture of 6-chloro-N-(4-(8-chloro-[1,2,4]triazolo[4,3-c]pyrazin-3-yl)phenyl)benzo[d]thiazol-2-amine (63C) (3.0 g, 7.26 mmol), Pd(OAc)$_2$ (650 mg, 2.90 mmol), dppp (1.20 g, 2.90 mmol), Et$_3$N (2.94 g, 29.0 mmol), DMSO (40 mL) and MeOH (20 mL) until the pressure reached to 30 psi. The bottle was then sealed and heated at 70° C. for 2 h. The reaction mixture was cooled to room temperature, and the precipitate was collected by filtration to yield the title compound as a greenish solid (1.25 g, 40%). HPLC/MS (Method C): retention time=2.22 min, [M+H]$^+$=437.4. $^1$H NMR (500 MHz, DMSO-d$_6$): δ 10.96 (s, 1H), 8.84 (d, J=4.95 Hz, 1H), 8.02-8.14 (m, 3H), 7.94-8.01 (m, 3H), 7.64 (d, J=8.25 Hz, 1H), 7.38 (dd, J=8.80, 2.20 Hz, 1H), 4.03 (s, 3H).

Preparation 63E: 3-(4-(6-Chlorobenzo[d]thiazol-2-ylamino)phenyl)-[1,2,4]triazolo[4,3-c]pyrazine-8-carboxylic acid

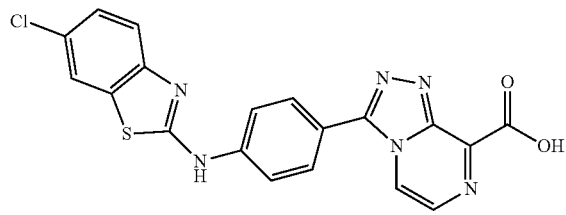

(63E)

To a solution of methyl 3-(4-(6-chlorobenzo[d]thiazol-2-ylamino)phenyl)-[1,2,4]triazolo[4,3-a]pyrazine-8-carboxylate (63D) (1.127 g, 2.58 mmol) in THF (150 mL) was added potassium trimethylsilanolate (881 mg, 6.87 mmol). The mixture was stirred at room temperature for 1 h. The insoluble material was collected by filtration and discarded. The filtrate was diluted with water (80 mL) and concentrated in vacuo to remove most of the THF. The remaining aqueous material was neutralized by addition of saturated aqueous $NH_4Cl$ solution. The resulting precipitate was filtered, rinsed with water and methanol, and air dried to yield the title compound as a brown solid (1.025 g, 94%). HPLC/MS (Method C): retention time=1.98 min, [M+H]$^+$=423.4. $^1$H NMR (500 MHz, DMSO-$d_6$): δ 8.40 (d, J=4.40 Hz, 1H), 8.03 (d, J=8.25 Hz, 2H), 7.99 (s, 1H), 7.94 (d, J=8.25 Hz, 2H), 7.71 (d, J=4.95 Hz, 1H), 7.64 (d, J=8.80 Hz, 1H), 7.37 (d, J=8.25 Hz, 1H).

Example 63

A suspension of 3-(4-(6-chlorobenzo[d]thiazol-2-ylamino)phenyl)-[1,2,4]triazolo[4,3-a]pyridine-8-carboxylic acid (63E) (60 mg, 0.14 mmol), EDC (27 mg, 0.14 mmol) and HOBt (19 mg, 0.14 mmol) in a mixed solvent of DMF (1 mL) and DCM (1 mL) was stirred until it became a clear solution, and then L-valine tert-butyl ester hydrochloride salt (30 mg, 0.12 mmol) and triethylamine (29 mg, 0.28 mmol) were added. The mixture was stirred at room temperature for 2 h. Analysis by HPLC indicated the starting acid was not consumed. Additional amount of EDC (15 mg), HOBt (10 mg) and L-valine tert-butyl ester hydrochloride salt (10 mg) were added and the reaction mixture stirred for another 1 h. The reaction was concentrated in vacuo. The crude product was purified by preparative HPLC using $CH_3CN/H_2O$/TFA solvent system to yield the product (a tert-butyl ester intermediate, 10 mg) as a brown solid. HPLC purity: 95%; LCMS: [M+H]$^+$=578.5.

A solution of the tert-butyl ester intermediate (10 mg) in a mixed solvent of TFA (0.5 mL) and DCM (0.5 mL) was stirred at room temperature for 4 h. The reaction mixture was concentrated in vacuo to yield the title compound as a brown solid (7.7 mg). HPLC/MS (Method C): retention time=2.42 min, [M+H]$^+$=522.4. $^1$H NMR (500 MHz, DMF-$d_7$): δ 9.78 (d, J=8.25 Hz, 1H), 8.97 (d, J=4.95 Hz, 1H), 8.20-8.24 (m, 2H), 8.11 (d, J=8.80 Hz, 2H), 8.06 (d, J=2.20 Hz, 1H), 7.70-7.85 (m, 1H), 7.47 (dd, J=8.80, 2.20 Hz, 1H), 4.77 (dd, J=8.52, 4.67 Hz, 1H), 2.36-2.49 (m, 1H), 1.06-1.31 (m, 6H).

Example 64

(S)-1-(3-(4-(6-Chlorobenzo[d]thiazol-2-ylamino)phenyl)-[1,2,4]-triazolo[4,3-a]pyrazine-8-carbonyl)pyrrolidine-2-carboxylic acid

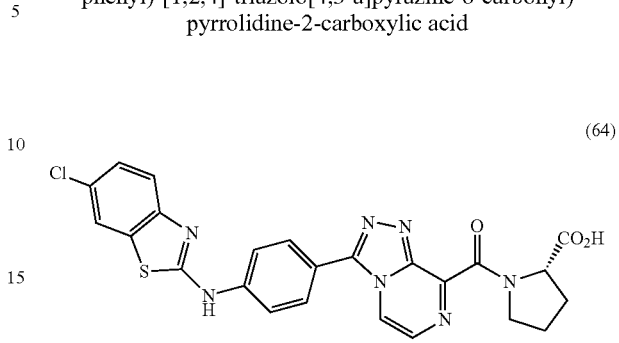

(64)

The title compound was prepared from 3-(4-(6-chlorobenzo[d]thiazol-2-ylamino)phenyl)-[1,2,4]triazolo[4,3-a]pyrazine-8-carboxylic acid (63E) and L-proline tert-butyl ester by analogous procedure described in Example 63F. HPLC/MS (Method C): retention time=2.03-2.16 min (broad rotomer), [M+H]$^+$=520.4. $^1$H NMR (500 MHz, DMSO-$d_6$): δ 10.97 (s, 1H), 8.66-8.80 (m, 1H), 8.03-8.10 (m, 2H), 7.94-8.02 (m, 4H), 7.65 (d, J=8.80 Hz, 1H), 7.38 (dd, J=8.25, 2.20 Hz, 1H), 4.50-4.66 (m, 1H), 3.42-3.78 (m, 2H), 2.19-2.39 (m, 1H), 1.81-2.05 (m, 3H).

Example 65

(S)-3-(4-(6-Chlorobenzo[d]thiazol-2-ylamino)phenyl)-N-(1-hydroxybutan-2-yl)-[1,2,4]triazolo[4,3-a]pyrazine-8-carboxamide

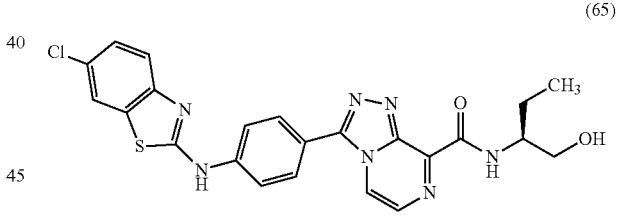

(65)

A suspension of 3-(4-(6-chlorobenzo[d]thiazol-2-ylamino)phenyl)-[1,2,4]triazolo[4,3-a]pyridine-8-carboxylic acid (63E) (43 mg, 0.1 mmol), EDC (24.4 mg, 0.127 mmol) and HOBt (17.2 mg, 0.127 mmol) in DMF (1 mL) was stirred for 5 min, and then (S)-2-aminobutan-1-ol, hydrochloride salt (13 mg, 0.104 mmol) and triethylamine (20.6 mg, 0.203 mmol) were added. The mixture was stirred at room temperature overnight. To the reaction mixture was added anhydrous DCM (1 mL), followed by additional EDC (25 mg) and HOBt (17 mg). The resulting mixture was then stirred for additional 2 h before concentrated in vacuo. The crude product was purified by preparative HPLC using MeOH/$H_2O$/TFA solvent system to yield the title compound (3 mg). HPLC/MS (Method C): retention time=2.14 min (broad rotomer), [M+H]$^+$=494.1. $^1$H NMR (500 MHz, DMSO-$d_6$): δ 10.97 (s, 1H), 8.98 (d, J=8.25 Hz, 1H), 8.77 (d, J=4.95 Hz, 1H), 8.02-8.09 (m, 3H), 7.93-8.01 (m, 3H), 7.64 (d, J=8.80 Hz, 1H), 7.38 (dd, J=8.80, 2.20 Hz, 1H), 3.94-4.03 (m, 1H), 3.57 (dd, J=10.72, 4.67 Hz, 1H), 3.48 (dd, J=11.00, 5.50 Hz, 1H), 1.48-1.61 (m, 1H), 0.89-1.02 (m, 3H).

Example 66

(S)-3-Methyl-2-(3-(4-(3-(2-(trifluoromethyl)phenyl)ureido)phenyl)-[1,2,4]triazolo[4,3-b]pyridazine-8-carboxamido)butanoic acid

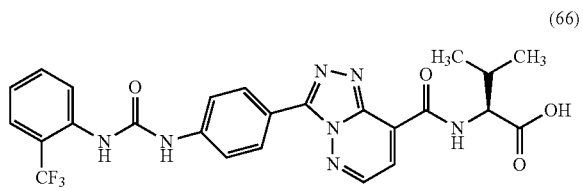
(66)

Preparation 66A: tert-Butyl 3,6-dichloropyridazine-4-carboxylate

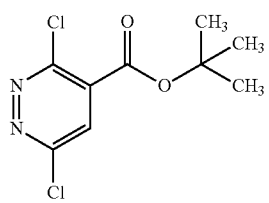
(66A)

A mixture of 3,6-dichloropyridazine-4-carboxylic acid (5.79 g, 30 mmol), tert-butanol (2.45 g, 33 mmol), 2-chloro-1-methylpyridinium iodide (6.12 g, 24 mmol), and tributylamine (8.9 g, 48 mmol) in dichloromethane (52 mL) was stirred at refluxing under $N_2$ for 3 h. After cooling to room temperature, the reaction mixture was concentrated under reduced pressure. The residue was purified using a silica gel cartridge (330 g) which was pretreated with 1% $Et_3N$ in hexanes for 10 min at 10 mL/min, eluting with a gradient of EtOAc (0-50%) in hexanes to afford 6.1 g (81%) of the title compound as a white solid. HPLC/MS (Method B): retention time=2.95 min, $[M+H]^+$=249.1.

Preparation 66B: tert-Butyl 6-chloro-3-hydrazinylpyridazine-4-carboxylate

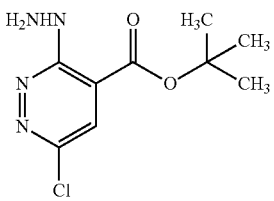
(66B)

To a solution of tert-butyl 3,6-dichloropyridazine-4-carboxylate (66A) (3.9 g, 15.6 mmol) in EtOH (20 mL) was added anhydrous hydrazine (2 mL). The reaction mixture was stirred at room temperature for 2 h, and then concentrated under reduced pressure. The crude product was triturated with 80% EtOH in $H_2O$ to afford 1.58 g (40%) of the title compound as a yellow solid. HPLC/MS (Method B): retention time=1.77 min, $[M+H]^+$=189.3.

Preparation 66C: tert-Butyl 3-(2-(4-(tert-butoxycarbonylamino)benzoyl)hydrazinyl)-6-chloropyridazine-4-carboxylate

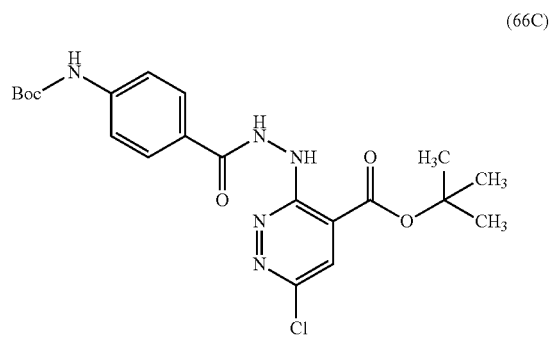
(66C)

To a solution of tert-butyl 6-chloro-3-hydrazinylpyridazine-4-carboxylate (66B) (800 mg, 3.27 mmol) in anhydrous DMF (5 mL) was added 4-(tert-butoxycarbonyl-amine)benzoic acid (1.0 g, 4.25 mmol), EDC (940 mg, 4.91 mmol), HOBt (663 mg, 4.91 mmol), followed by DIPEA (1.1 mL, 6.54 mmol). The reaction mixture was stirred at room temperature overnight. The reaction mixture was partitioned between EtOAc and water, the separated EtOAc layer washed with water, saturated aqueous $NaHCO_3$, saturated aqueous NaCl (2×), dried (anhydrous $Na_2SO_4$), and concentrated. The obtained residue was dried in high vacuum for 1.5 h to afford 1.49 g (98%) of the title compound. HPLC/MS (Method B): retention time=3.40 min, $[M+H]^+$=464.3.

Preparation 66D: tert-Butyl 3-(4-(tert-butoxycarbonylamino)phenyl)-6-chloro-[1,2,4]triazolo[4,3-b]pyridazine-8-carboxylate

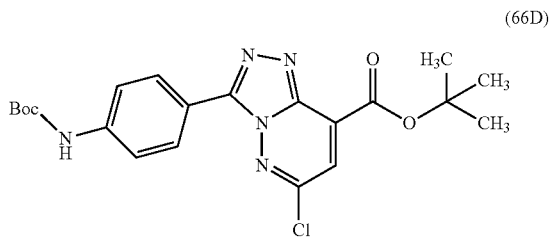
(66D)

To a solution of tert-butyl 3-(2-(4-(tert-butoxycarbonylamino)benzoyl)hydrazinyl)-6-chloropyridazine-4-carboxylate (66C) (1.49 g, 3.20 mmol) in a mixed solvent of THF (10 mL) and $CCl_4$ (5 mL) at 0° C. under argon was added $Et_3P$ (3.35 mL, 19.2 mmol), followed by DIPEA (3.35 mL, 19.2 mmol). The reaction mixture was stirred at 0° C. for 10 min. Analysis by LC/MS indicated the starting material was consumed. The reaction mixture was partitioned between EtOAc and water, the separated EtOAc layer washed with water, saturated aqueous $NaHCO_3$, saturated aqueous NaCl (2×), dried (anhydrous $Na_2SO_4$), and concentrated. The crude residue was purified using a silica gel cartridge (40 g) which was pretreated with 1% $Et_3N$ in hexanes for 10 min at 10 mL/min, eluting with a gradient of EtOAc (0-50%) in hexanes to afford 1.02 g (71%) of the title compound as a yellow solid. HPLC/MS (Method B): retention time=3.78 min, [M+H]⁺=446.3.

Preparation 66E: tert-Butyl 3-(4-(tert-butoxycarbonylamino)phenyl)-[1,2,4]triazolo[4,3-b]pyridazine-8-carboxylate

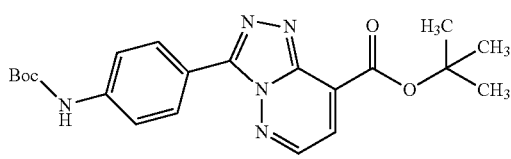

(66E)

A solution of tert-butyl 3-(4-(tert-butoxycarbonylamino) phenyl)-6-chloro-[1,2,4]triazolo[4,3-b]pyridazine-8-carboxylate (66D) (300 mg, 0.67 mmol) in a mixed solvent of EtOH (4 mL) and MeOH (1 mL) was bubbled through argon for 5 min, and then NaOAc (66.2 mg, 0.81 mmol) was added, followed by 5% Pd/C (50 mg). The vessel was evacuated and flashed with H₂ gas three times and stirred under H₂ (1 atm) for 1 h. Analysis by LC/MS indicated the starting material was consumed. The reaction mixture was filtered, and the filtrate concentrated under reduced pressure. The obtained crude residue was purified using a silica gel cartridge (40 g) eluting with a gradient of EtOAc (0-100%) in hexanes to afford 150 mg (54%) of the title compound as a yellow foam. HPLC/MS (Method B): retention time=3.02 min, [M+H]⁺=412.3.

Preparation 66F: tert-Butyl 3-(4-aminophenyl)-[1,2,4]-triazolo[4,3-b]pyridazine-8-carboxylate

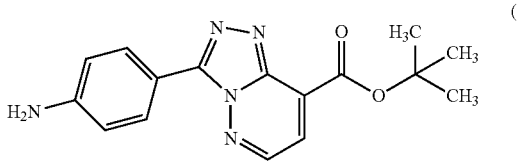

(66F)

To a solution of tert-butyl 3-(4-(tert-butoxycarbonylamino)phenyl)-[1,2,4]triazolo[4,3-b]pyridazine-8-carboxylate (66E) (100 mg, 0.24 mmol) in CH₂Cl₂ (4 mL) was added iodotrimethylsilane (86 µL, 0.6 mmol) dropwise. After addition, the reaction mixture was stirred at room temperature for 10 min. Analysis by LC/MS indicated the starting material was consumed. The reaction mixture was partitioned between CH₂Cl₂ and water, then the separated CH₂Cl₂ layer was washed with water, saturated aqueous NaHCO₃, saturated aqueous NaCl, dried (anhydrous Na₂SO₄), and concentrated. The obtained crude residue was purified using a silica gel cartridge (12 g) eluting with a gradient of EtOAc (50-100%) in hexanes to afford 60 mg (79%) of the title compound as a yellow solid. HPLC/MS (Method B): retention time=2.03 min, [M+H]⁺=312.3.

Preparation 66G: tert-Butyl 3-(4-(3-(2-(trifluoromethyl)phenyl)ureido)phenyl)-[1,2,4]triazolo[4,3-b]pyridazine-8-carboxylate

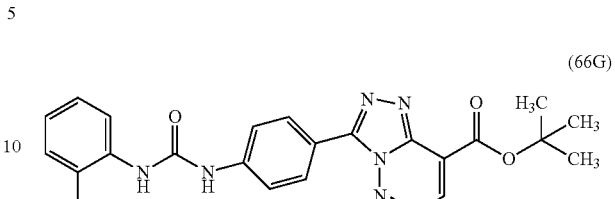

(66G)

To a suspension of tert-butyl 3-(4-aminophenyl)-[1,2,4] triazolo[4,3-b]pyridazine-8-carboxylate (66F) (60 mg, 0.19 mmol) in THF (3 mL) was added 4-(trifluoromethyl)-phenyl isocyanate (43.3 mg, 0.23 mmol). The reaction mixture was stirred at 60° C. for 2 h before allowed to cool to room temperature. The reaction mixture was partitioned between EtOAc and water, then the separated EtOAc layer was washed with saturated aqueous NaCl, dried (anhydrous Na₂SO₄), and concentrated. The obtained crude residue was purified using a silica gel cartridge (12 g) eluting with a gradient of EtOAc (50-100%) in hexanes to afford 62 mg (65%) of the title compound as a yellow solid. HPLC/MS (Method B): retention time=3.52 min, [M+H]⁺=499.4.

Preparation 66H: 3-(4-(3-(2-(Trifluoromethyl)phenyl)ureido)phenyl)-[1,2,4]triazolo[4,3-b]pyridazine-8-carboxylic acid

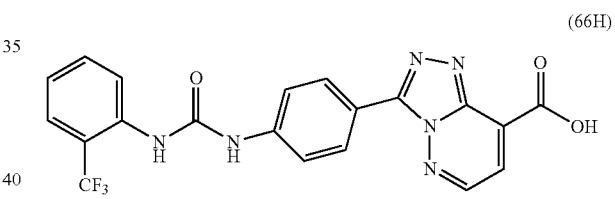

(66H)

A solution of tert-butyl 3-(4-(3-(2-(trifluoromethyl)phenyl)ureido)phenyl)-[1,2,4]triazolo[4,3-b]pyridazine-8-carboxylate (66G) (58 mg, 0.12 mmol) in a mixed solvent of TFA (0.5 mL) and CH₂Cl₂ (0.5 mL) was stirred at room temperature for 3 h. Analysis by LC/MS indicated the starting material was consumed. The reaction was concentrated under reduced pressure, chased with CH₂Cl₂ (2×) and dried in high vacuum for 2 h to afford 51 mg of the title compound as a yellow solid. HPLC/MS (Method B): retention time=2.81 min, [M+H]⁺=443.3.

Preparation 66I: (S)-tert-Butyl 3-methyl-2-(3-(4-(3-(2-(trifluoromethyl)phenyl)ureido)phenyl)-[1,2,4]triazolo[4,3-b]pyridazine-8-carboxamido)butanoate

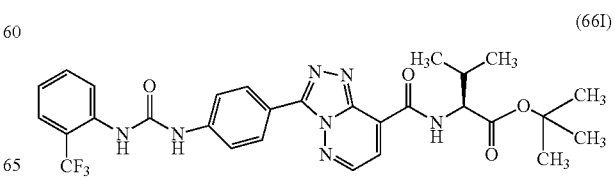

(66I)

To a solution of 3-(4-(3-(2-(trifluoromethyl)phenyl)ureido)phenyl)-[1,2,4]triazolo[4,3-b]pyridazine-8-carboxylic acid (66H) (38 mg, 0.086 mmol) in anhydrous DMF (1 mL) was added L-valine tert-butyl ester hydrochloride (23.4 mg, 0.11 mmol), EDC (24.7 mg, 0.13 mmol), HOBt (17 mg, 0.13 mmol), followed by DIPEA (45 μL, 0.26 mmol). The reaction mixture was stirred at room temperature for 3 h. Analysis by LC/MS indicated the starting material was consumed. The reaction mixture was partitioned between EtOAc and water, then the separated EtOAc layer was washed with water, saturated aqueous NaHCO$_3$, saturated aqueous NaCl, dried (anhydrous Na$_2$SO$_4$), and concentrated. The obtained crude residue was purified using a silica gel cartridge (12 g) eluting with a gradient of EtOAc (0-100%) in hexanes to afford 33 mg (63%) of the title compound as a yellow solid. HPLC/MS (Method B): retention time=4.04 min, [M+H]$^+$=598.4.

Example 66

A solution of (S)-tert-butyl 3-methyl-2-(3-(4-(3-(2-(trifluoromethyl)phenyl)ureido)phenyl) [1,2,4]triazolo[4,3-b]pyridazine-8-carboxamido)butanoate (66I) (32 mg, 0.053 mmol) in a mixed solvent of TFA (0.5 mL) and CH$_2$Cl$_2$ (0.5 mL) was stirred at room temperature for 2 h. Analysis by LC/MS indicated the starting eater was consumed. The reaction was concentrated under reduced pressure. Water (5 mL) was added to the residue, and the resulting yellow precipitate was collected by filtration, washed with water and dried in a 50° C. vacuum oven to afford 20 mg (70%) of the title compound as a yellow solid. HPLC/MS (Method B): retention time=3.34 min, [M+H]$^+$=542.4. $^1$H NMR (500 MHz, DMSO-d$_6$): δ 13.13 (s, 1H), 9.77 (d, J=7.72 Hz, 1H), 9.71 (s, 1H), 8.92 (d, J=3.84 Hz, 1H), 8.33 (d, J=7.68 Hz, 2H), 8.21 (s, 1H), 7.95 (d, J=7.68 Hz, 1H), 7.87 (d, J=3.32 Hz, 1H), 7.61-7.82 (m, 4H), 7.24-7.34 (m, 1H), 4.52-4.65 (m, 1H), 2.23-2.39 (m, 1H), 1.02 (q, J=7.12 Hz, 6H).

Biological Evaluation

DGAT1 Enzyme Assay

DGAT1 enzyme assays were conducted using membranes isolated from Sf9 insect cells expressing the recombinant human DGAT1 cDNA. The assays were conducted in 384-well plates with total volume of 25 μl at 25° C. In each assay, 300 ng of recombinant human DGAT1 membrane was incubated with 25 μM of 2-monooleoylglycerol and 25 μM of [$^3$H]-stearoyl-CoA in 100 mM potassium phosphate (pH 7.4) for 30 min with various concentrations of compounds delivered in DMSO. The assay was terminated by the addition of 30 μl of Stopping Solution [50 mM HEPES, 5 mg/mL Yttrium Oxide (YOX) Polylysine SPA beads, 3.33 mg/mL Fraction V BSA, 200 μM Mercuric chloride]. The signal was measured using LEADSEEKER$^{SM}$ for 5 minutes. To calculate the degree of inhibition, the zero level of enzyme activity (blank) was defined by the above assay using Sf9 cell membrane uninfected with baculovirus and the 100% level of DGAT1 enzyme activity was defined by human DGAT1 assay with the vehicle DMSO. The IC$_{50}$ values of inhibitors were determined by Excel-fit.

Compounds described herein were tested in the DGAT1 enzyme assay described immediately above. The following results were obtained.

TABLE 1

| Example | DGAT1 Enzyme Assay IC$_{50}$ (inhibition) (μM) |
|---------|-----------------------------------------------|
| 5       | 0.17                                          |
| 6       | 0.15                                          |
| 11      | 0.15                                          |
| 14      | 0.18                                          |
| 16      | 0.003                                         |
| 22      | 31                                            |
| 23      | 43                                            |
| 25      | 0.007                                         |
| 41      | 0.005                                         |
| 47      | 28                                            |
| 53      | 23                                            |
| 63      | 0.007                                         |

What is claimed is:

1. A compound according to Formula (I):

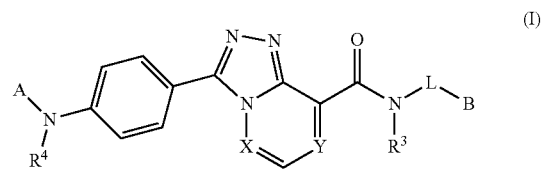

or a pharmaceutically acceptable salt thereof:
wherein:
A is hydrogen, alkyl, cycloalkyl, aryl, heterocyclyl, —C(O)R$^6$, —C(O)OR$^6$, or —C(O)NR$^6$R$^7$;
L is —(CR$^1$R$^2$)$_n$—;
n is 1, 2, or 3;
B is —OR$^5$, —C(O)OR$^5$, —OC(O)R$^5$, or —OC(O)OR$^5$;
X and Y are each CH;
R$^1$ and R$^2$ are, independently at each occurrence, hydrogen, hydroxyalkyl, alkyl, cycloalkyl, aryl, and/or heterocyclyl, or one R$^1$ and one R$^2$ form a C$_3$-C$_7$cycloalkyl or 4- to 7-membered heterocyclyl ring having one or two heteroatoms;
R$^3$ is hydrogen or alkyl, or R$^3$ and R$^1$ form a 4- to 7-membered heterocyclyl ring having one or two heteroatoms;
R$^4$ is hydrogen or alkyl;
R$^5$ is hydrogen or alkyl;
R$^6$ is alkyl, cycloalkyl, aryl, or heterocyclyl; and
R$^7$ is hydrogen or alkyl, or R$^7$ and R$^6$ together with the nitrogen atom to which they are attached form a 4- to 7-membered heterocyclyl ring having one or two heteroatoms;
wherein:
each of said alkyl is substituted with 0-3 R$^a$;
each of said cycloalkyl is substituted with 0-3 R$^a$;
each of said aryl is substituted with 0-4 R$^b$; and
each of said heterocyclyl is substituted with 0-4 R$^b$;
R$^a$ is, independently at each occurrence, F, Cl, Br, —CF$_3$, —OH, —OCH$_3$, —OCF$_3$, —CN, —NR$^c$R$^d$, phenyl, imidazolyl, and/or C$_1$-C$_3$alkoxy;
R$^b$ is, independently at each occurrence, C$_1$-C$_4$alkyl, F, Cl, Br, —CF$_3$, —OH, —OCH$_3$, —OCF$_3$, —CN, —NR$^c$R$^d$, and/or C$_1$-C$_3$alkoxy; and
R$^c$ and R$^d$ are, independently at each occurrence, H and/or C$_1$-C$_4$alkyl, or R$^c$ and R$^d$ together with the nitrogen atom to which they are attached, form a 4- to 7-membered heterocyclyl ring with one or two heteroatoms.

2. The compound according to claim 1 wherein:

A is hydrogen, $C_1$-$C_6$alkyl, $C_3$-$C_7$cycloalkyl, aryl, 1- or 2-ring heterocyclyl, —C(O)$R^6$, —C(O)O$R^6$, or —C(O)N$R^6R^7$;

$R^1$ and $R^2$ are, independently at each occurrence, hydrogen, $C_1$-$C_6$alkyl, $C_3$-$C_7$cycloalkyl, aryl, and/or 1- or 2-ring heterocyclyl, or one $R^1$ and one $R^2$ form a $C_3$-$C_7$cycloalkyl or 4- to 7-membered heterocyclyl ring having one or two heteroatoms;

$R^3$ is hydrogen or $C_1$-$C_6$alkyl, or $R^3$ and $R^1$ form a 4- to 7-membered heterocyclyl ring having one or two heteroatoms;

$R^4$ is hydrogen or $C_1$-$C_6$alkyl;

$R^5$ is hydrogen or $C_1$-$C_6$alkyl;

$R^6$ is $C_1$-$C_6$alkyl, $C_3$-$C_7$cycloalkyl, aryl, or 1- or 2-ring heterocyclyl;

$R^7$ is hydrogen or $C_1$-$C_6$alkyl, or $R^7$ and $R^6$ together with the nitrogen atom to which they are attached form a 4- to 7-membered heterocyclyl ring having one or two heteroatoms;

wherein:
each alkyl is substituted with 0-3 $R^a$;
each cycloalkyl is substituted with 0-3 $R^a$;
each aryl is substituted with 0-4 $R^b$; and
each heterocyclyl is substituted with 0-4 $R^b$.

3. The compound according to claim 2 wherein:

A is hydrogen, $C_1$-$C_4$alkyl, phenyl, 1- or 2-ring heterocyclyl having 1- or 2-heteroatoms selected from S and N, —C(O)$R^6$, —C(O)O$R^6$, or —C(O)N$R^6R^7$;

$R^1$ is hydrogen, $C_1$-$C_6$alkyl, $C_3$-$C_7$cycloalkyl, or phenyl;

$R^2$ is hydrogen or methyl;

or $R^1$ and $R^2$ form a $C_5$-$C_7$cycloalkyl ring or 5- to 6-membered heterocyclyl ring having one or two heteroatoms;

$R^3$ is hydrogen or $C_1$-$C_4$alkyl, or $R^3$ and $R^1$ form a 5- to 7-membered heterocyclyl ring having 1 or 2 heteroatoms;

$R^4$ is hydrogen or $C_1$-$C_4$alkyl;

$R^5$ is hydrogen or $C_1$-$C_4$alkyl;

$R^6$ is $C_1$-$C_4$alkyl, or phenyl; and $R^7$ is hydrogen or methyl;

wherein:
each alkyl is substituted with 0-3 $R^a$;
each cycloalkyl is substituted with 0-3 $R^a$;
each phenyl is substituted with 0-3 $R^b$; and
each heterocyclyl is substituted with 0-3 $R^b$.

4. The compound according to claim 3 wherein:

A is hydrogen, —C(O)$R^6$, —C(O)O$R^6$, —C(O)NH$R^6$, thiazolyl, or benzothiazolyl;

B is —OH or —C(O)O$R^5$;

$R^1$ is hydrogen, $C_1$-$C_4$alkyl, $C_5$-$C_7$cycloalkyl, or phenyl;

$R^2$ is hydrogen;

or $R^1$ and $R^2$ form a $C_5$-$C_7$cycloalkyl;

$R^3$ is hydrogen or $C_1$-$C_2$alkyl, or $R^3$ and $R^1$ form a 5- to 6-membered heterocyclyl ring having one heteroatom;

$R^4$ is hydrogen or $C_1$-$C_2$alkyl;

$R^5$ is hydrogen or $C_1$-$C_4$alkyl; and n is 1 or 2;

wherein:
each alkyl is substituted with 0-2 $R^a$;
each cycloalkyl is substituted with 0-2 $R^a$;
each heterocyclyl is substituted with 0-2 $R^b$;
each phenyl is substituted with 0-2 $R^b$;
each thiazolyl is substituted with 0-2 $R^b$; and
each benzothiazolyl is substituted with 0-2 $R^b$;

$R^a$ is, independently at each occurrence, F, Cl, Br, —$CF_3$, —OH, —$OCH_3$, —$OCF_3$, phenyl, and/or imidazolyl; and $R^b$ is, independently at each occurrence, $C_1$-$C_4$alkyl, F, Cl, Br, —$CF_3$, —OH, —$OCH_3$, —$OCF_3$, and/or —CN.

5. The compound according to claim 4 wherein:

A is hydrogen, —C(O)—$CH_2CH_3$, —C(O)-benzyl, —C(O)O—$CH_3$, —C(O)O-(butyl), —C(O)NH-(trifluoromethylphenyl), —C(O)NH-(trifluoromethoxyphenyl), thiazolyl, or chlorobenzothiazolyl;

B is —OH, —C(O)OH, or —C(O)O$CH_2CH_3$;

$R^1$ is hydrogen, $C_1$-$C_4$alkyl, hydroxyethyl, cyclohexyl, phenyl, or methyl substituted with phenyl, hydroxyphenyl, or imidazolyl;

$R^2$ is hydrogen;

or $R^1$ and $R^2$ form a cyclopentyl ring;

$R^3$ is hydrogen, or $R^3$ and $R^1$ form a pyrrolidinyl ring; and $R^4$ is hydrogen.

6. The compound wherein said compound is:

(2)

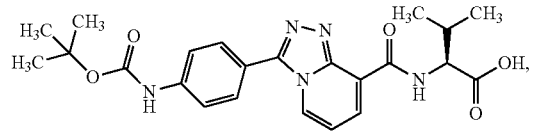

(2A)

(3)

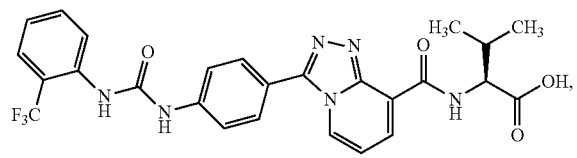

(3A)

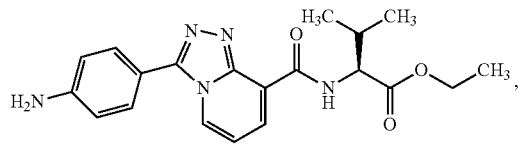

(3B)

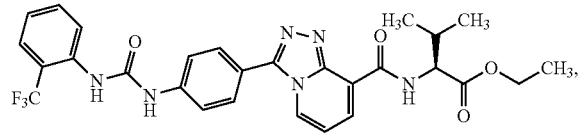

(4)

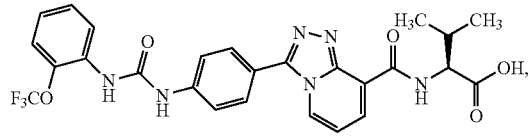

-continued
(5)
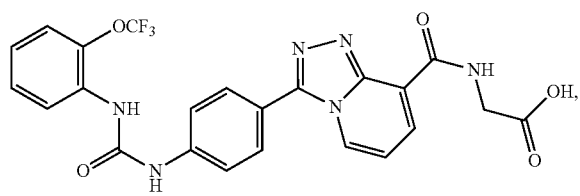
(6)
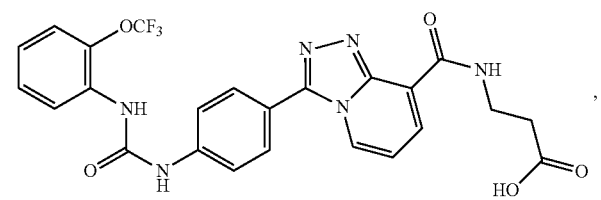
(7)
(8)
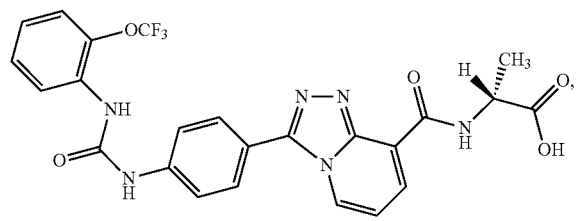
(9)
(10)
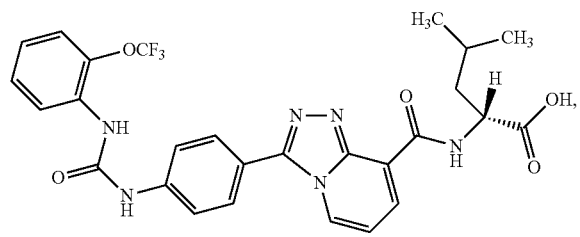
(11)
(12)
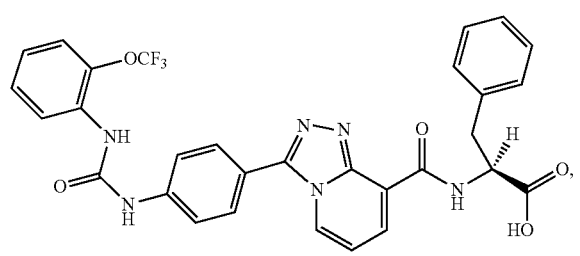
(13)
(14)
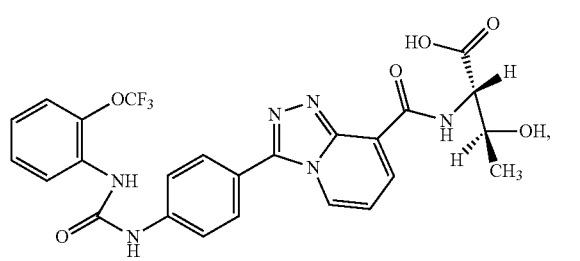
(15)
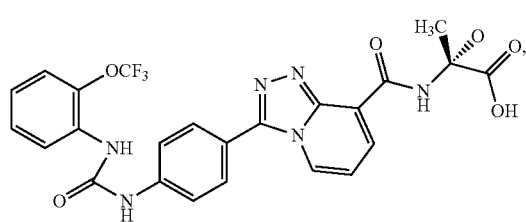
(16)
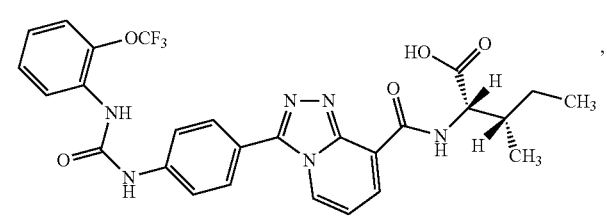

-continued
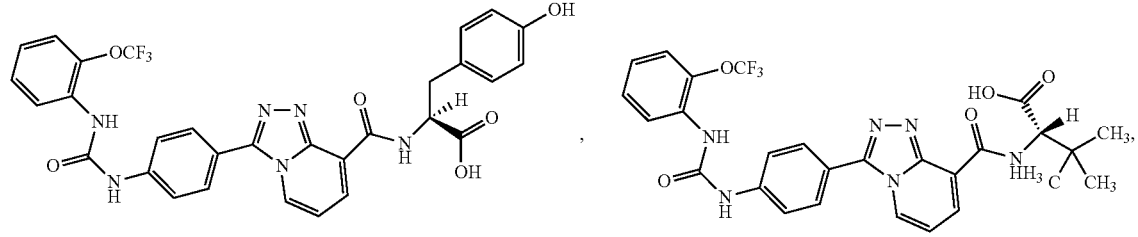
(17) (18)
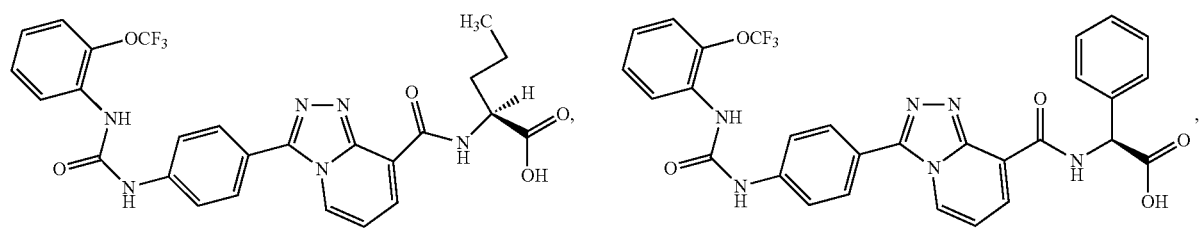
(19) (20)
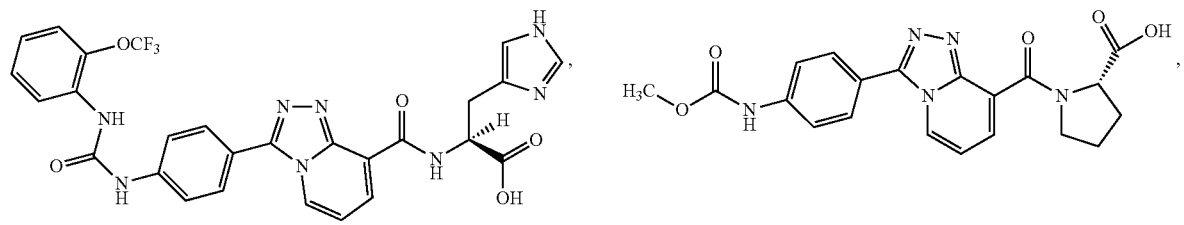
(21) (22)
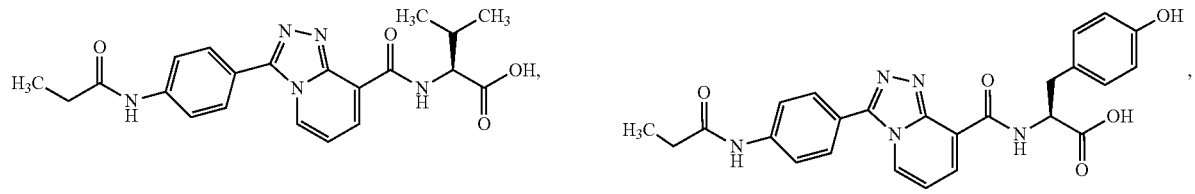
(23) (24)
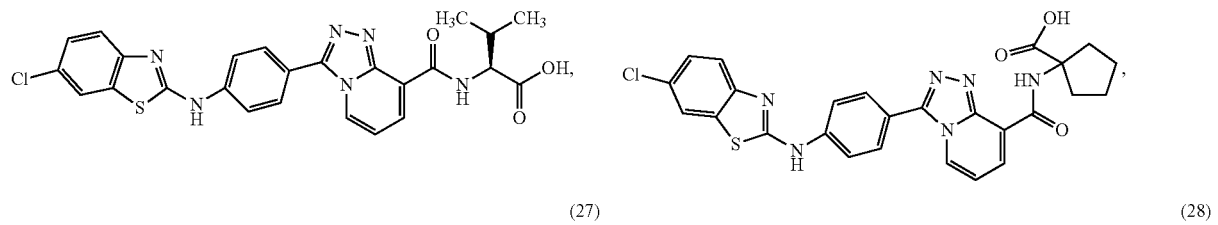
(25) (26)
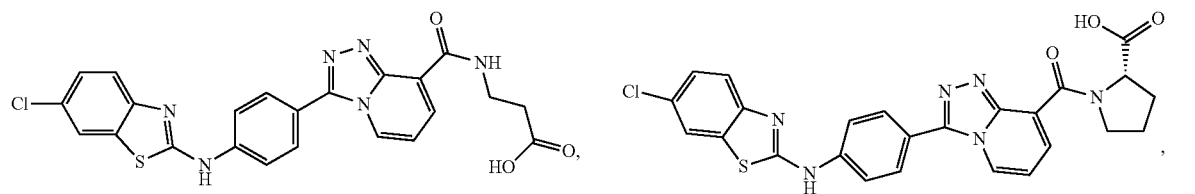
(27) (28)
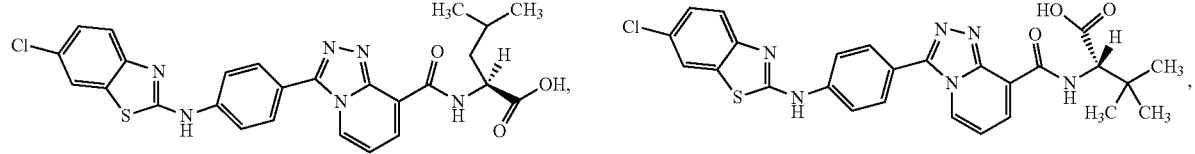
(29) (30)

-continued
(31)
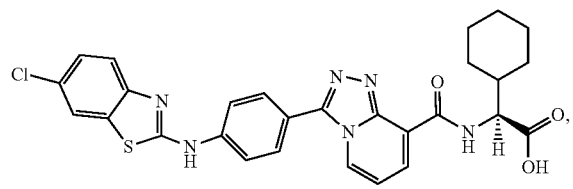
(32)
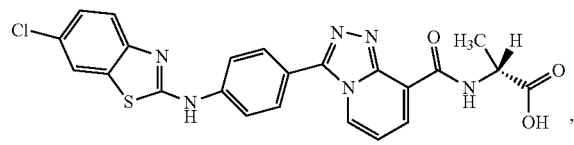
(33)
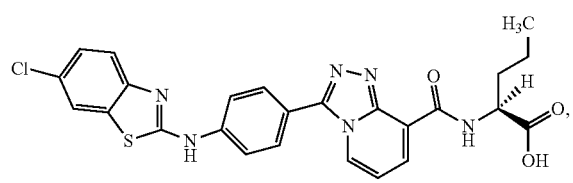
(34)
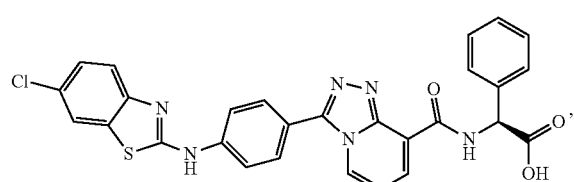
(35)
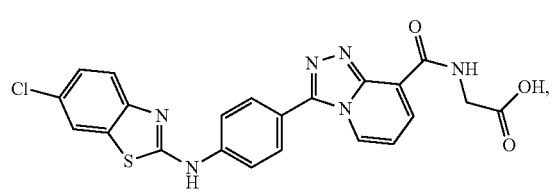
(36)
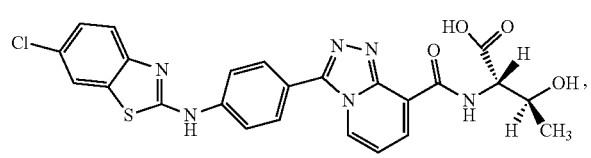
(37)
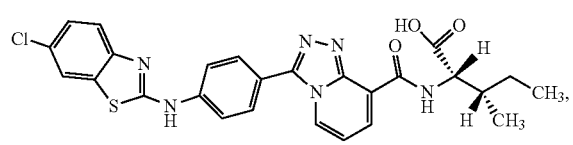
(38)
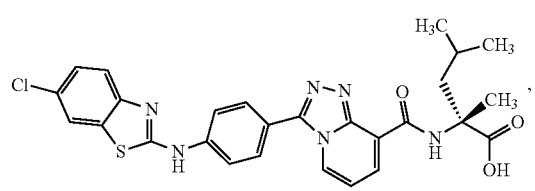
(39)
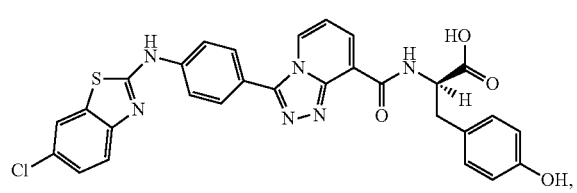
(40)
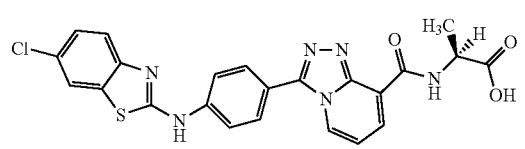
(41)
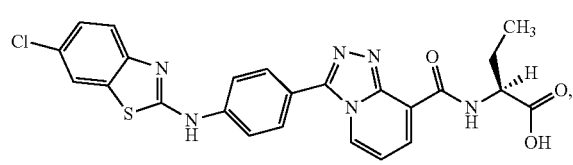
(42)
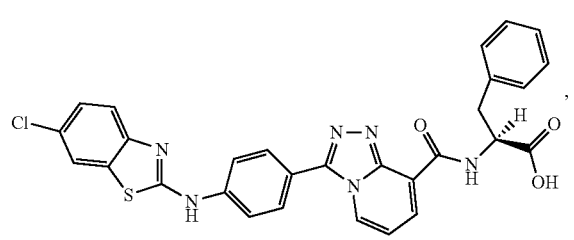
(43)
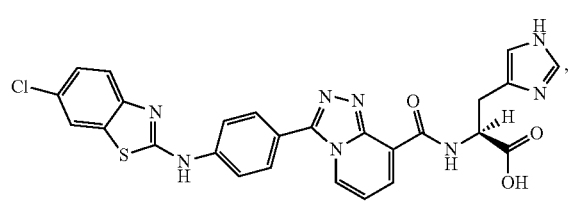
(44)
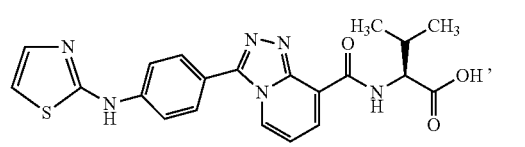

-continued
(45)
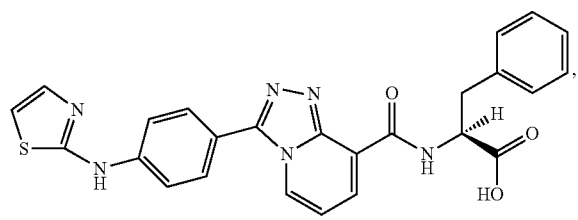
(46)
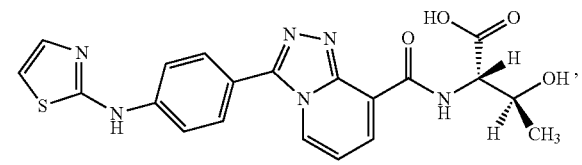
(47)
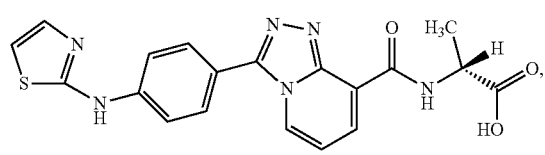
(48)
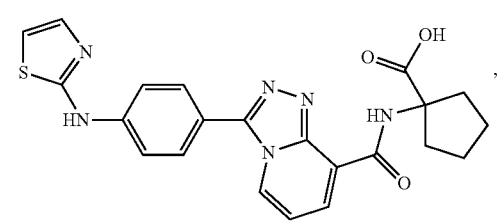
(49)
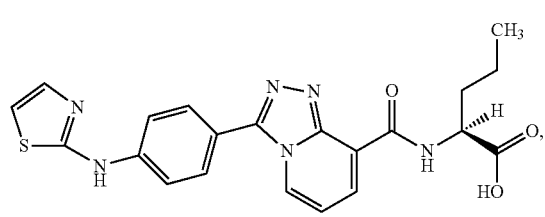
(50)
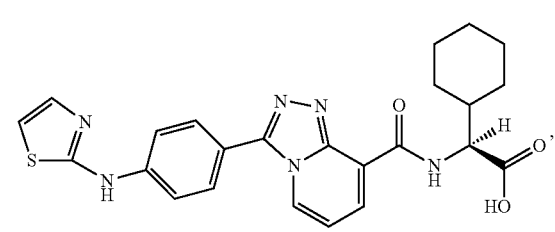
(51)
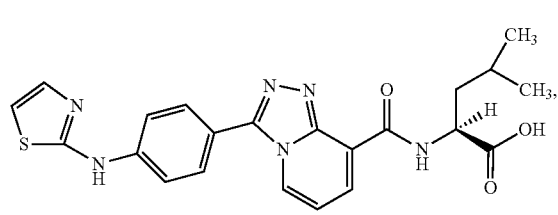
(52)
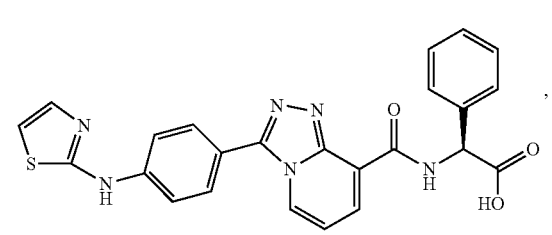
(53)
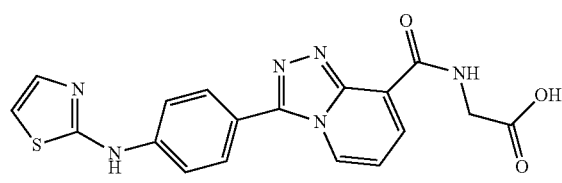
(54)
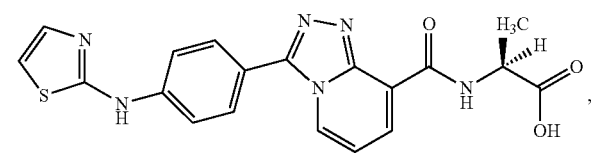
(55)
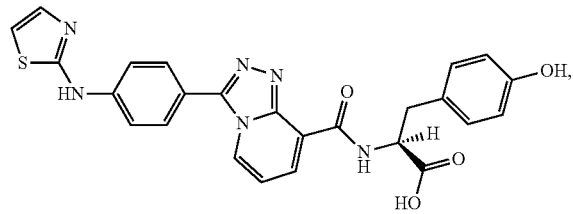
(56)
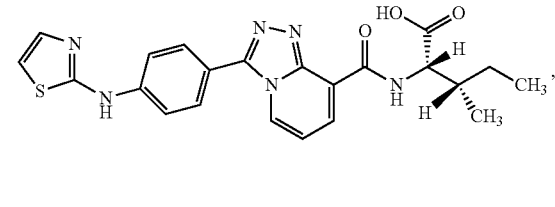
(57)
(58)

(59) 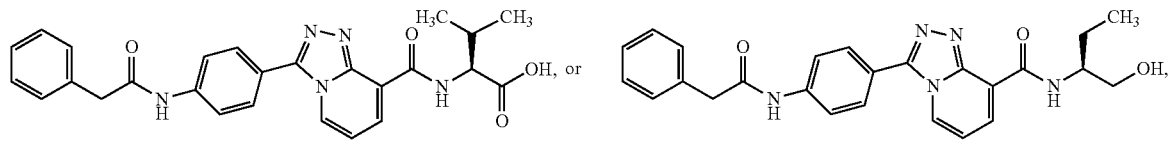
or a pharmaceutically acceptable salt of any of said compounds (1) through (60).
7. A pharmaceutical composition comprising a compound according claim 1 together with a pharmaceutically acceptable carrier.
8. The compound according to claim 1 wherein the compound is:
(60) 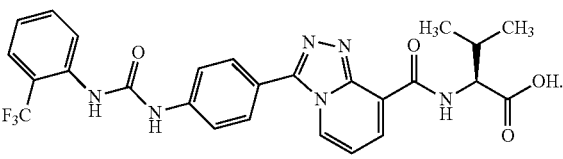
* * * * *

UNITED STATES PATENT AND TRADEMARK OFFICE
CERTIFICATE OF CORRECTION

PATENT NO. : 8,324,241 B2  
APPLICATION NO. : 12/936969  
DATED : December 4, 2012  
INVENTOR(S) : Yanting Huang et al.

Page 1 of 2

It is certified that error appears in the above-identified patent and that said Letters Patent is hereby corrected as shown below:

In the Specification:

Column 1, line 4, change "PCT/US00/39770," to -- PCT/US2009/039770, --.

In the Claims:

Claim 6:

Column 99, sixth structure, change

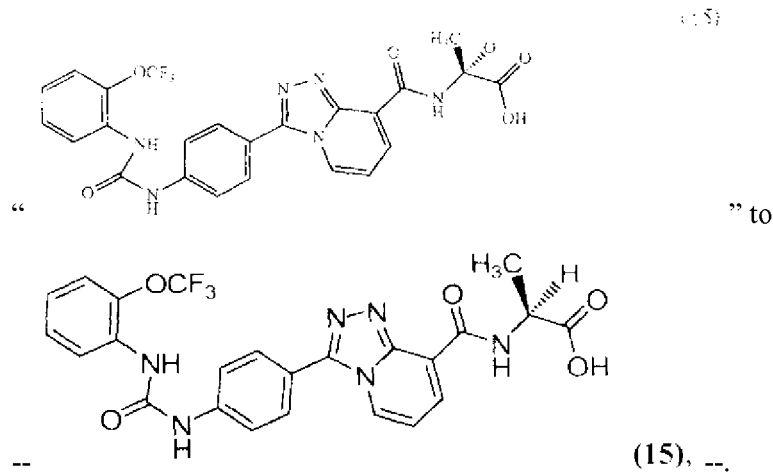

In the Claims:

Signed and Sealed this  
Fourteenth Day of May, 2013

Teresa Stanek Rea  
*Acting Director of the United States Patent and Trademark Office*

CERTIFICATE OF CORRECTION (continued)
U.S. Pat. No. 8,324,241 B2

Claim 6 (continued):

Column 101, first structure, change

"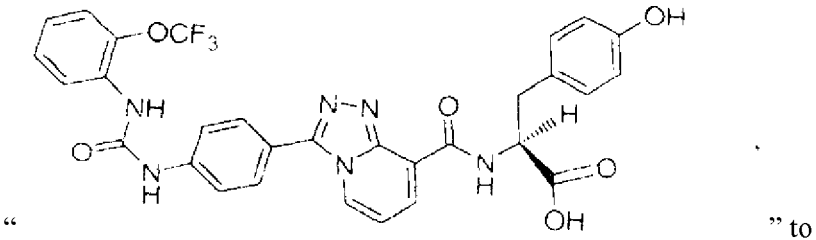" to

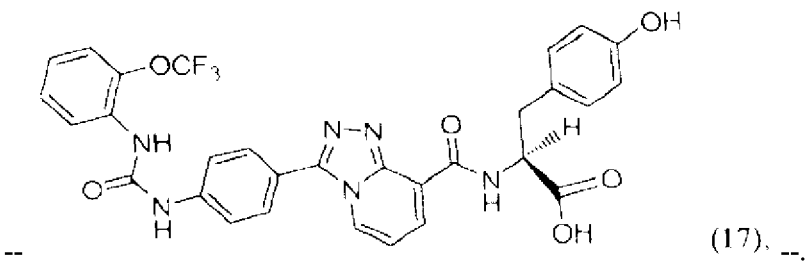 (17), --.

Claim 6 (continued):

Column 102, first structure, change

"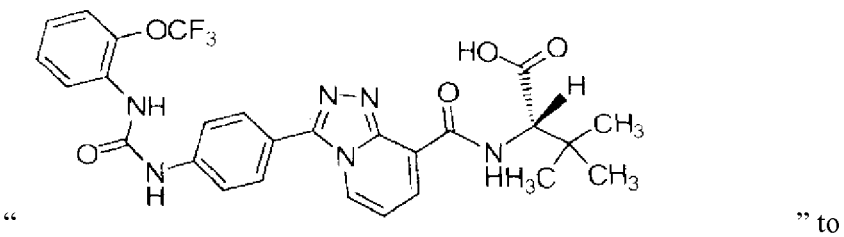" to

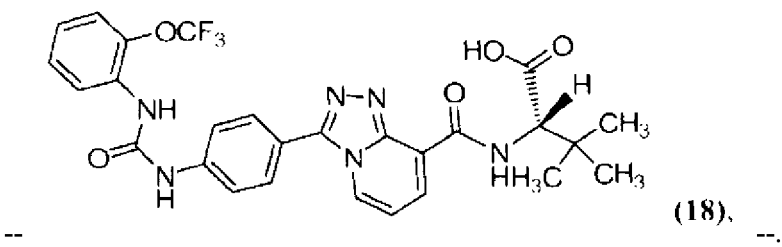 (18), --.